United States Patent [19]
Kato et al.

[11] Patent Number: 5,495,023
[45] Date of Patent: Feb. 27, 1996

[54] NITRO COMPOUNDS, PROCESS FOR PREPARATION THEREOF AND USE THEREOF

[75] Inventors: Masayuki Kato, Kyoto; Shigetaka Nishino; Mitsuko Hamano, both of Osaka; Hisashi Takasugi, Sakai, all of Japan

[73] Assignee: Fujisawa Pharmaceutical Co., Ltd., Osaka, Japan

[21] Appl. No.: 211,949

[22] PCT Filed: Nov. 2, 1992

[86] PCT No.: PCT/JP92/01414

§ 371 Date: May 3, 1994

§ 102(e) Date: May 3, 1994

[87] PCT Pub. No.: WO93/10097

PCT Pub. Date: May 27, 1993

[30] Foreign Application Priority Data

Nov. 15, 1991 [GB] United Kingdom ............ 9124324
Sep. 4, 1992 [GB] United Kingdom ............ 9218741

[51] Int. Cl.⁶ .................. C07D 213/81; C07D 213/71; C07D 213/82; A61K 31/44
[52] U.S. Cl. .................. 546/316; 544/224; 544/236; 544/242; 544/265; 544/315; 544/406; 546/22; 546/122; 546/169; 546/318; 546/323; 546/329; 546/335; 548/136; 548/169; 548/200; 548/248; 548/251; 548/266.8; 548/333.5; 548/375.1; 548/472; 548/477; 548/326.1; 548/473; 552/10; 558/170; 558/458; 560/165; 564/59; 564/79; 564/95; 564/191; 564/193; 564/197; 564/258; 564/268
[58] Field of Search ............ 558/458; 564/191, 564/193, 258, 268, 197, 79, 59, 95; 560/165; 514/478, 629, 600, 588, 601, 356, 417, 355, 381, 367, 354, 357, 365, 396; 546/318, 316, 323, 335; 548/477, 251, 169, 200, 333.5

[56] References Cited

U.S. PATENT DOCUMENTS 4,863,926  9/1989  Okamoto et al. .......... 514/255

FOREIGN PATENT DOCUMENTS 113106  7/1984  European Pat. Off. .
168921  1/1986  European Pat. Off. .

*Primary Examiner*—Emily Bernhardt
*Attorney, Agent, or Firm*—Oblon, Spivak, McClelland, Maier & Neustadt

[57] ABSTRACT

A new nitro compound of the formula:

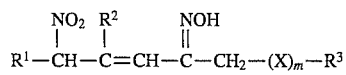

wherein
$R^1$ and $R^2$ are each lower alkyl or lower alkoxy(lower)alkyl, or

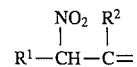

is cyclized to form

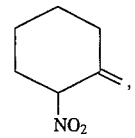

X is —O—, —S— or —NH—,
m is an integer 0 or 1, and
$R^3$ is carbamoyl, lower alkylcarbamoyl, lower alkanoyl, di-lower alkylaminosulfonyl, lower alkylsulfonyl, oxamoyl or a group of the formula: $-(Y)_n-R^4$
wherein
Y is —CO—, —SO$_2$—, —COCH$_2$— or

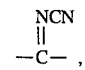

n is an integer of 0 or 1, and
$R^4$ is heterocyclic group which is optionally substituted with one or more substituents selected from lower alkyl, lower alkoxy, phenyl, carbamoyl, halogen, amino, lower alkylthio, hydroxy, lower alkylsulfonylamino and carbamoylmethyl, and pharmaceutically acceptable salt thereof, which are useful as vasodilators.

2 Claims, No Drawings

NITRO COMPOUNDS, PROCESS FOR PREPARATION THEREOF AND USE THEREOF

This application is a 371 of PCT/JP92/01414 filed Nov. 2, 1992.

TECHNICAL FIELD

This invention relates to new nitro compounds. More particularly, this invention relates to new nitro compounds and their pharmaceutically acceptable salts, which are useful for vasodilator, to processes for preparation thereof, to a pharmaceutical composition comprising the same and to a method of use thereof.

BACKGROUND ART

EP-A-0113106 discloses nitro compounds which are useful for vasodilator, but an increase of durability of pharmacological effect of these compounds is desired.

This invention is to provide new nitro compounds which are useful for vasodilator and have increased durability of pharmacological effect.

DISCLOSURE OF INVENTION

The objective new nitro compounds are represented by the following formula (I):

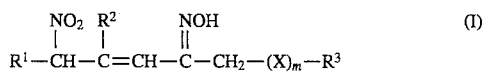

wherein $R^1$ and $R^2$ are each lower alkyl or lower alkoxy(lower)alkyl, or

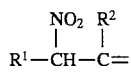

is cyclized to form

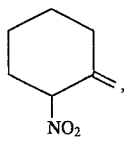

X is —O—, —S— or —NH—, m is an integer 0 or 1, and $R^3$ is carbamoyl, lower alkylcarbamoyl, lower alkanoyl, di-lower alkylaminosulfonyl, lower alkylsulfonyl, oxamoyl or a group of the formula: $-(Y)_n-R^4$ wherein Y is —CO—, —SO$_2$—, —COCH$_2$— or

n is an integer of 0 or 1, and $R^4$ is heterocyclic group which is optionally substituted with one or more substituents selected from lower alkyl, lower alkoxy, phenyl, carbamoyl, halogen, amino, lower alkylthio, hydroxy, lower alkylsulfonylamino and carbamoylmethyl.

Preferred examples and illustrations of various definitions in the description hereinabove and hereinbelow, which the present invention includes within the scope thereof are explained in detail as follows.

The term "lower" is intended to mean 1 to 6 carbon atoms, unless otherwise indicated.

Preferred example of "lower alkyl" may include a residue of straight and branched alkane having 1 to 6 carbon atom(s) such as methyl, ethyl, propyl, isopropyl, butyl, isobutyl, t-butyl, pentyl, isopentyl, neopentyl, hexyl, isohexyl and the like.

Preferred examples of "lower alkylcarbamoyl" may include methylcarbamoyl, N,N-dimethylcarbamoyl, ethylcarbamoyl, propylcarbamoyl, isopropylcarbamoyl, butylcarbamoyl, isobutylcarbamoyl, tert-butylcarbamoyl and the like.

Preferred examples of "lower alkanoyl" may include formyl, acetyl, propionyl, butyl, isobutyryl, valeryl, isovaleryl, pivaloyl, hexanoyl, 3,3-dimethylbutyryl and the like.

Preferred examples of "di-lower alkylaminosulfonyl" may include di-methylaminosulfonyl, di-ethylaminosulfonyl and the like.

Preferred examples of "halogen" is fluorine, chlorine, bromine and iodine.

Preferred examples of "lower alkoxy" may include a straight or branched one such as methoxy, ethoxy, propoxy, isopropoxy, butoxy, isobutoxy, tert-butoxy, pentyloxy, hexyloxy or the like, in which the preferable one is $C_1-C_4$ alkoxy and the most preferable one is methoxy or ethoxy.

Preferred examples of "lower alkylsulfonylamino" may include methylsulfonylamino, ethylsulfonylamino and the like.

Preferred examples of "lower alkoxy(lower)alkyl" may include methoxymethyl, methoxyethyl, ethoxymethyl, propoxymethyl and the like.

Preferred examples of "lower alkylthio" may include methylthio, ethylthio, propylthio, isopropylthio, butylthio and the like.

Preferred examples of "lower alkylsulfonyl" may include mesyl, ethylsulfonyl, propylsulfonyl, isopropylsulfonyl, butylsulfonyl and the like.

Preferred examples of "heterocyclic group" may include a unsaturated 3- to 8-membered monocyclic heterocyclic group containing 1 to 4 nitrogen atoms such as pyrrolyl, pyrrolinyl, imidazolyl, pyrazolyl, pyridyl and its N-oxide, dihydropyridyl, pyrimidinyl, pyrazinyl, 6-oxo-1,4,5,6-tetrahydropyridazinyl, pyridazinyl, triazolyl (e.g. 4H-1,2,4-triazolyl, 1H-1,2,3-triazolyl, 2H-1,2,3-triazolyl, 1H-1,2,4-triazolyl, etc.), tetrazolyl (e.g. 1H-tetrazolyl, 2H-tetrazolyl, etc.), and the like, a 3- to 8- membered monocyclic heterocyclic group containing at least one sulfur atom and at least one nitrogen atom such as thiazolyl, isothiazolyl, thiadiazolyl and the like, 3- to 8- membered monocyclic heterocyclic group containing at least one oxygen atom and at least one nitrogen atom such as isoxazolyl and the like, a polycyclic (e.g. bicyclic) heterocyclic group containing at least one nitrogen atom such as indolyl, 2-oxoindolyl, isoindolyl, indolizinyl, benzimidazolyl, quinolyl, isoquinolyl, quinazolinyl, phthalimido, purinyl, 8-oxo-7H-pyrido[2,3-d]pyridazinyl, 1,8-naphthyridinyl, imidazo[1,2-a]pyridyl and the like, a polycyclic (e.g. bicyclic) heterocyclic group containing at least one sulfur atom and at least one nitrogen atom such as benzothiazolyl, benzothiadiazolyl and the like, a polycyclic (e.g. bicyclic) heterocyclic group containing at least one oxygen atom such as benzofuranyl, isobenzofuranyl and the like, a polycyclic (e.g. bicyclic) heterocyclic group containing at least one oxygen atom and at least one nitrogen atom such as benzoxazolyl, benzoxadiazolyl and the like.

A pharmaceutically acceptable salt of the compound (I) may include a salt with an inorganic or organic base such as an alkali metal salt (e.g. sodium salt, potassium salt, etc.), an alkaline earth metal salt (e.g. calcium salt, etc.), ammonium salt, an organic amine salts such as ethanolamine salt, triethylamine salt, dicyclohexylamine salt and the like, and organic or inorganic acid addition salts such as acetate, trifluoroacetate, lactate, maleate, fumarate, tartrate, citrate, toluenesulfonate, methanesulfonate, hydrochloride, sulfate, nitrate, phosphate and so on.

Such pharmaceutically acceptable salts of the compound (I) can be prepared by a conventional method, i.e., by treating the compound (I) with the corresponding base or acid.

The compound (I) and the pharmaceutically acceptable salt of this invention can be prepared by the following methods.

Process 1:

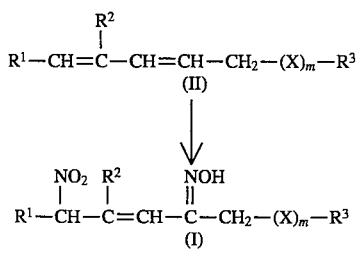

Process 2:

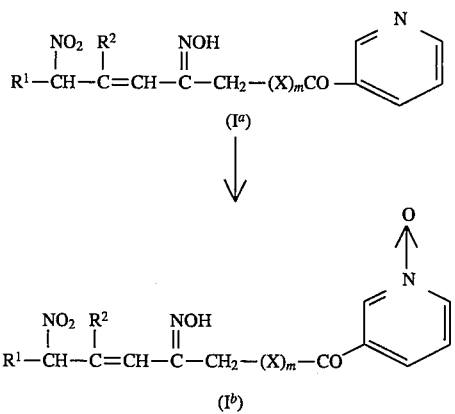

In the above formulas, $R^1$, $R^2$, X, m and $R^3$ are as defined above.

Process 1:

The compound (I) and its salt can be prepared by reacting the compound (II) or its salt with dinitrogen trioxide, or in the presence of an acid, a nitrite.

Preferred examples of salts of those compounds (II) and (I) may include the same ones as those of the compound (I).

This reaction is carried out by reacting directly the compound (II) or its salt with dinitrogen trioxide. The dinitrogen trioxide is usually prepared by a nitrite and an acid, and accordingly this reaction is usually carried out by reacting the compound (II) or its salt with a nitrite in the presence of an acid, instead that such dinitrogen trioxide is directly employed.

Preferred examples of a nitrite may include salts of nitrous acid such as an alkali metal salt (e.g. sodium salt, potassium salt, etc.), an alkaline earth metal salt (e.g. calcium salt, etc.) and the like.

Preferred examples of acids may include an inorganic or organic acid such as hydrochloric acid, sulfuric acid, formic acid, acetic acid and the like.

This reaction is preferably carried out in a solvent such as water, alcohol (e.g. methanol, ethanol, propanol, etc.), tetrahydrofuran, dioxane, dichloromethane or a mixture thereof.

This reaction is preferably carried out under somewhat milder conditions such as under cooling, at room temperature or under warming.

Process 2:

The compound ($I^b$) or its salt can be prepared by oxidizing the compound ($I^a$) or its salt.

Suitable salts of the compounds ($I^a$) and ($I^b$) may include the same as those exemplified as pharmaceutically acceptable salts of the compound (I) hereinbefore.

This oxidation reaction can be carried out by a conventional method which is applied for the transformation of —N— into

for example by using an oxidizing agent such as m-chloroperbenzoic acid, perbenzoic acid, peracetic acid, ozone, hydrogen peroxide, periodic acid or the like.

This reaction is usually carried out in a solvent such as water, acetone, dioxane, acetonitrile, chloroform, dichloromethane, tetrahydrofuran, ethyl acetate or any other solvent which does not adversely affect the reaction.

The reaction temperature is not critical and the reaction is preferably carried out under cooling or at ambient temperature.

The starting compound (II) or its salt are the new one and can be prepared by the following methods:

(1) Method 1

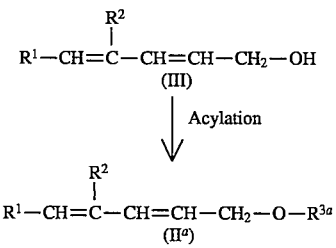

(2) Method 2

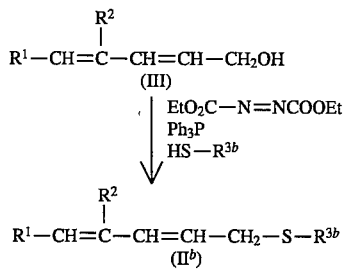

(3) Method 3

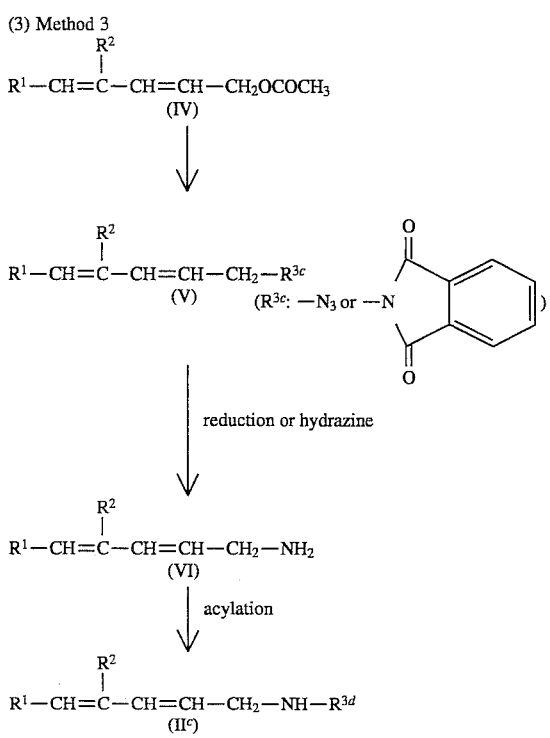

In the above formulae, $R^{3a}$ is carbamoyl, lower alkylcarbamoyl or CO—$R^4$ wherein $R^4$ is as defined above, $R^{3b}$ is heterocyclic group which is optionally substituted by lower alkyl or phenyl, $R^{3d}$ is lower alkanoyl, di-lower alkylaminosulfonyl or a group of the formula: Y—$R^4$ wherein Y and $R^4$ are each as defined above, and $R^1$ and $R^2$ are each as defined above.

Method 1:

The compound ($II^a$) or its salt can be prepared by reacting the compound (III) or its salt with an acylating agent.

This reaction is conducted in a conventional manner.

Method 2:

The compound ($II^b$) or its salt can be prepared by reacting the compound (III) or its salt with a compound of the formula: HS—$R^{3b}$ wherein $R^{3b}$ is as defined above, triphenylphosphine and diethyl azodicarboxylate.

Method 3:

The compound ($II^c$) or its salt can be prepared by reacting the compound (IV) or its salt with sodium azide or potassium phthalimide in the presence of palladium catalyst to give the compound (V) or its salt, and reducing the resulting compound (V) or its salt, or reacting the compound (V) or its salt with hydrazine to give the compound (VI) or its salt and then reacting the resulting compound (VI) or its salt with an acylating agent.

As to the nitro compounds (I) and starting compounds (II), ($II^a$), ($II^b$), ($II^c$) and (III) to (VI), it is to be noted that each of said compounds includes one or more stereo isomers and all of such isomers are included within the scope of this invention.

The new nitro compounds (I) and their pharmaceutically acceptable salts of this invention have been found to possess relaxation effect on smooth-muscles (e.g. cardiovascular dilating effect, etc.) and hypotensive effect, and further are capable of inhibiting platelet aggregation.

Accordingly, the new nitro compounds (I) and their pharmaceutically acceptable salts are useful for vasodilator which is used for the treatment of coronary insufficiency, angina pectoris and myocardial infarction, and also useful for anti-hypertensive agent which is used for the treatment of hypertension. Further, they are used as an anti-thrombotic agent for the treatment of cerebral apoplexy, thrombosis and pulmonary embolism, and as a preventing agent for restenosis after PTCA.

Furthermore, durability of such pharmacological effects of the new nitro compounds (I) and their pharmaceutically acceptable salts are increased as compared to those of the afore-mentioned prior art compounds.

For the purpose of showing such pharmaceutical activities of the new nitro compounds (I), pharmacological test data thereof are illustrated in the followings.

i) Anti-platelet aggregation activity:

Inhibitory activity of the nitro compounds of this invention against human platelet aggregation was measured according to the method described below.

Platelet aggregation:

Blood was collected from human volunteers. The blood was prevented from coagulation with 1 volume of 3.8% sodium citrate to 9 volumes of blood. Platelet rich plasma (PRP) was prepared by centrifugation of the blood at 1300 rpm for 10 min. at 10° C. The PRP was diluted with platelet poor plasma obtained by further centrifugation of the blood at 3000 rpm for 10 min. The platelet counts in the PRP used for aggregation studies were about $4.0 \times 10^5$ platelets/$mm^3$. Aggregation studies were performed turbidimetrically using NKK HEMATRACER 1. To 225 µl of PRP 25 µl of the test compounds was added and preincubated for 2 min. After preincubation 5 µl of aggregating agents were added to the mixture. Collagen and ADP were used as aggregating agents at the concentrations of 0.5 µg/ml and 2.5 µM, respectively. Activities of the test compounds were expressed as $ED_{50}$ values i.e. concentrations required to inhibit the platelet aggregation responses by 50%.

Results are shown in the following Table.

TABLE 1

| Test Compound (Example Number) | $ED_{50}$ (µM) Inducer: Collagen | ADP |
|---|---|---|
| Example 2 A | 4.6 | 8.6 |
| Example 2 B | 3.6 | 2.4 |
| Example 5 A | | 5.1 |
| Example 6 A | | 1.8 |
| Example 6 B | | 1.9 |
| Example 12 A | | 1.1 |
| Example 12 B | | 1.7 |

(A: Isomer A, B: Isomer B, the same meaning in the Tables hereinafter)

ii) Effect on mean arterial blood pressure in anesthetized rats:

Male Sprague-Dawley rats, aged 9–12 weeks, were anesthetized with urethane (1.4 g/kg i.p.). A polyethylene cannula filled with heparin solution was inserted into the femoral artery of the rats to measure mean blood pressure. Mean blood pressure was measured with a pressure transducer and recorded on a polygraph. The test compound dissolved in ethanol, polyethylene glycol and distilled water (1:1:2), were administered intravenously in a volume of 0.25 ml/kg. Intravenous hypotensive effects of each compound were expressed as the maximal decrease (R max) and the half time (T ½). Briefly, R max was expressed as maximal % change compared to mean blood pressure prior to the administration of compound. T ½ was expressed as a time during which the hypotensive effect recovered to half of the maximal decrease. The result are shown in Table 2.

TABLE 2

| Test Compound (Example No.) | Dose (mg/kg) | Hypotensive effect R max (%) | T ½ (min.) |
|---|---|---|---|
| Example 1 A | 0.1 | 21.7 | |
| | 0.32 | 37.0 | |
| Example 1 B | 0.032 | 11.8 | |
| | 0.1 | 41.6 | |
| Example 2 B | 0.032 | 30.9 | 5.3 |
| | 0.1 | 35.4 | 7.3 |
| Example 3 A | 0.032 | 12.6 | 4.8 |
| | 0.1 | 29.3 | 7.2 |
| Example 4 A | 0.1 | 24.6 | 6.7 |
| | 0.32 | 40.8 | 5.1 |
| Example 5 A | 0.1 | 36.5 | 7.6 |
| | 0.32 | 49.9 | 12.8 |
| Example 5 B | 0.1 | 34.3 | 6.2 |
| Example 6 A | 0.032 | 4.7 | |
| | 0.1 | 16.9 | 6.8 |
| | 0.32 | 36.3 | 11.2 |
| Example 6 B | 0.032 | 10.5 | 8.6 |
| | 0.1 | 29.3 | 9.0 |
| Example 7 A | 0.1 | 31.7 | 7.6 |
| | 0.32 | 42.1 | 5.1 |
| Example 7 B | 0.1 | 28.9 | 6.6 |
| Example 12 A | 0.032 | 16.7 | 7.4 |
| | 0.1 | 37.7 | 5.9 |
| Example 12 B | 0.1 | 41.5 | |
| Example 14 B | 0.032 | 4.7 | |
| | 0.1 | 33.9 | |
| Example 18 A | 0.32 | 10.2 | |
| | 1.0 | 33.6 | 31.5 |
| Example 18 B | 0.32 | 15.3 | |
| | 1.0 | 37.8 | 20.2 |
| Example 19 A | 0.32 | 40.3 | 12.6 |
| Example 19 B | 0.32 | 35.3 | 11.0 |
| Example 20 | 0.32 | 3.8 | |
| | 3.2 | 48.4 | 20.1 |
| Example 21 | 0.32 | 26.5 | 13.1 |
| Example 22 | 0.32 | 17.7 | |
| | 1.0 | 35.9 | 24.9 |
| Example 24 | 0.32 | 31.8 | 13.6 |
| Example 25 A | 0.32 | 24.1 | 13.1 |
| Example 25 B | 0.32 | 31.1 | |
| Example 28 | 0.32 | 22.2 | |
| | 1.0 | 31.4 | 11.9 |
| Example 29 | 0.32 | 35.0 | 12.3 |
| Example 30 A | 0.32 | 37.9 | 16.9 |
| Example 30 B | 0.32 | 39.8 | 13.0 |
| Example 31 A | 0.32 | 24.3 | |
| Example 32 | 0.32 | 42.5 | 13.6 |
| Example 33 A | 0.32 | 20.9 | 11.9 |
| Example 35 | 0.32 | 41.7 | 13.7 |
| Example 40 | 0.32 | 52.3 | 11.3 |
| Example 42 | 0.32 | 44.4 | 14.2 |
| Example 43 | 0.32 | 53.1 | |
| Example 45 A | 0.32 | 31.2 | 11.9 | iii) Effect on mean arterial blood pressure in conscious rats:

Male Sprague-Dawley rats, aged 9–11 weeks, were anesthetized with ether and a polyethylene cannula filled with heparin solution was inserted into the femoral artery of the rats to measure mean blood pressure. Mean blood pressure was measured with a pressure transducer and recorded on a polygraph. Two hours after operation, the drug suspended in 0.5% methyl cellulose was administered orally in a volume of 5 ml/kg. Oral hypotensive effects of each compound were expressed as the maximal decrease (R max), the half time (T ½ ) and the duration (Dur.). Briefly, R max was expressed as maximal % change compared to mean blood pressure prior to the administration of compound. T ½ was expressed as a time during which the hypotensive effect recovered to half of the maximal decrease. Duration was expressed as a time during which the hypotensive effect recovered to 5% of the maximal decrease.

The results are shown in Table 3.

TABLE 3

| Test Compound (Example No.) | Dose (mg/kg) | Hypotensive effect R max (%) | T ½ (min.) | Dur. (min.) |
|---|---|---|---|---|
| Example 5 A | 3.2 | 27.2 | 16 | 30.8 |
| | 10 | 54.4 | 25 | 83.9 |
| | 32 | 60.6 | 75.6 | 144.2 |
| Example 6 A | 3.2 | 22.3 | 20 | 29.3 |
| | 10 | 27.2 | 30 | 116.0 |
| | 32 | 29.6 | 117 | >300 |
| Example 18 A | 10 | 25.7 | 40.1 | 57.0 |
| | 32 | 46.9 | 88.7 | 156.4 |
| Example 18 B | 10 | 38.9 | 26.4 | 54.7 |
| | 32 | 47.0 | 56.1 | 97.2 |
| Example 20 | 10 | 20.1 | 28.5 | |
| Example 21 | 10 | 34.3 | 34.1 | 67.7 |
| | 32 | 34.3 | 88.1 | >300 |
| Example 22 | 10 | 19.2 | 29.9 | |
| | 32 | 25.7 | 63.2 | |
| Example 24 | 10 | 40.7 | 16.6 | |
| Example 25 A | 10 | 19.3 | 22.5 | |
| | 32 | 26.0 | 56.7 | |
| Example 25 B | 10 | 41.3 | 14.6 | |
| Example 29 | 10 | 31.4 | 23.5 | 72.5 |
| | 32 | 37.1 | 165 | >300 |
| Example 30 A | 10 | 40.6 | 36.0 | 108.0 |
| | 32 | 39.3 | 56.2 | 211.1 |
| Example 30 B | 10 | 40.3 | 20.9 | |
| Example 31 A | 10 | 14.9 | 10.4 | |
| Example 32 | 10 | 43.2 | 19.6 | 50.9 |
| Example 33 A | 10 | 23.1 | 18.3 | |
| Example 35 | 10 | 31.1 | 24.1 | |
| Example 40 A | 10 | 47.8 | 25.2 | 71.1 |
| Example 45 A | 10 | 35.4 | 26.6 | 52.3 | iv) Vasodilating activity in vitro:

The thoracic aorta from male Sprague-Dawley rats, aged 9–11 weeks, were removed and cut into helical strips after removal of excess fat and connective tissues. The strips were mounted vertically in organ baths containing 25 ml Tyrode solution and isometric tension was measured. The tissue bath solution was maintained at 37° C. and bubbled with a 95% $O_2$ and 5% $CO_2$ gas mixture. After the resting tension was adjusted to 0.5 g, the strips were contracted by $3.2 \times 10^{-8}$ g/ml of norepinephrine (NE). The test compound dissolved in ethanol, polyethylene glycol and distilled water (1:1:2) were added to the organ bath cumulatively.

Then, relaxative activity of test compound was expressed as $IC_{50}$ value i.e. concentration required to inhibit the contraction response by 50%.

The results are shown in Table 4.

TABLE 4

| Test Compound (Example No.) | $IC_{50}$ (µM) |
|---|---|
| Example 1 A | 16.0 |
| Example 1 B | 10.0 |
| Example 2 B | 11.1 |
| Example 4 A | 1.2 |
| Example 4 B | 1.8 |
| Example 3 A | 18.8 |
| Example 5 A | 46.9 |
| Example 5 B | 88.7 |
| Example 6 A | 25.1 |
| Example 6 B | 9.3 |
| Example 7 A | 10.7 |
| Example 7 B | 19.4 |
| Example 12 A | 4.9 |
| Example 12 B | 5.0 |
| Example 14 B | 0.11 |

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, injection, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferable to apply it by intravenous, intramuscular or oral administration. While the dosage or therapeutically effective amount of the object compound of this invention varies from and also depends upon the age and condition of each individual patient to be treated, a daily dose of about 0.1–100 mg of the active ingredient/kg of a human being or an animal is generally given for treating diseases, and an average single dose of about 10 mg, 50 mg, 100 mg, 250 mg and 500 mg is generally administered.

The following examples are given for purpose of illustrating this invention.

In the following Examples, isomers A and B mean the following:

Isomer A: Isomer with high Rf value on thin layer chromatography (5~20% methanol in chloroform)

Isomer B: Isomer with low Rf value on thin layer chromatography (5~20% methanol in chloroform)

PREPARATION 1

To a mixture of (E,E)-4-ethyl-2,4-hexadien-1-ol (2.0 g), triethylamine (8 ml), and dichloromethane (15 ml) at 0° C. was added nicotinic acid chloride hydrochloride (4.23 g). The solution was stirred at 0° C. for 1.5 hours and at room temperature for 14 hours. The reaction mixture was washed with water and brine, dried over anhydrous magnesium sulfate, and evaporated in vacuo. The residue was chromatographed on silica gel (chloroform) to give 4-ethyl-2,4-hexadien-1-yl 3-pyridinecarboxylate (3.3 g) as an oil.

IR (Neat): 1725, 1645, 1590 $cm^{-1}$

NMR ($CDCl_3$, $\delta$): 1.02 (3H, t, J=8 Hz), 1.76 (3H, d, J=7 Hz), 2.26 (2H, q, J=8 Hz), 4.95 (2H, d, J=7 Hz), 5.60 (1H, q, J=7 Hz), 5.78 (1H, m), 6.30 (1H, d, J=16 Hz), 7.40 (1H, dd, J=5, 8 Hz), 8.32 (1H, br d, J=8 Hz), 8.77 (1H, d, J=4 Hz), 9.25 (1H, s)

PREPARATION 2

To a mixture of (E,E)-4-ethyl-2,4-hexadien-1-ol (3.0 g), sodium cyanate (3.1 g), and benzene (15 ml) at room temperature was added dropwise trifluoroacetic acid (5.42 g) during 1 hour. After being stirred for 2 hours at the same temperature, the reaction mixture was partitioned between water and ethyl acetate. The organic layer separated was washed with aqueous sodium bicarbonate, water and brine, dried over anhydrous magnesium sulfate, and evaporated in vacuo. The residue was chromatographed on silica gel (1% methanol-dichloromethane) to give 2.0 g of 4-ethyl-2,4-hexadien-1-yl carbamate.

IR (Neat): 3350, 1710, 1645, 1600 $cm^{-1}$

NMR ($CDCl_3$, $\delta$): 1.03 (3H, t, J=8 Hz), 1.74 (3H, d, J=7 Hz), 2.22 (2H, q, J=8 Hz), 4.60 (2H, d, J=7 Hz), 4.86 (2H, br s), 5.50–5.80 (2H, m), 6.16 (1H, d, J=17 Hz)

PREPARATION 3

A solution of (E,E)-4-ethyl-2,4-hexadien-1-ol (2.0 g) and ethyl isocyanate (1.13 g) in 1,2-dichloroethane (12 ml) was stirred at 0° C. for 3 hours and at room temperature for 12 hours. The reaction mixture was washed with water and brine, dried over anhydrous magnesium sulfate, and evaporated in vacuo. The residue was chromatographed on silica gel (chloroform) to give (E,E)-4-ethyl-2,4-hexadien-1-yl ethylcarbamate (2.5 g) as an oil.

IR (Neat): 3330, 1700, 1645, 1530 $cm^{-1}$

NMR ($CDCl_3$, $\delta$): 0.99 (3H, t, J=8 Hz), 1.14 (3H, t, J=7 Hz), 1.72 (3H, d, J=7 Hz), 2.20 (2H, q J=8 Hz), 3.22 (2H, m), 4.60 (2H, d, J=6 Hz), 4.60 (1H, br s), 5.53 (1H, q, J=7 Hz), 5.66 (1H, m), 6.18 (1H, d, J=16 Hz)

PREPARATION 4

A mixture of (E,E)-1-acetoxy-4-ethyl-2,4-hexadiene (11.0 g), potassium phthalimide (12.1 g), tetrakis(triphenylphosphine)palladium(O) (1.33 g), and N,N-dimethylformamide (120 ml) was stirred at 70° C. for 2 hours and at 100° C. for 2 hours under nitrogen atmosphere. After cooling, the precipitate was filtered and washed with N,N-dimethylformamide. The filtrate was evaporated in vacuo. The residue was partitioned between water and dichloromethane. The organic layer was washed with water and brine, dried over anhydrous magnesium sulfate, and evaporated in vacuo. The oil was chromatographed on silica gel (dichloromethane) to give a mixture of N-[(2E,4E)- and (2Z,4E)-4-ethyl-2,4-hexadien-1-yl]phthalimide (12.68 g) which crystallized on standing. This product was used in the next reaction without further purification.

IR (Nujol): 1770, 1720, 1610 $cm^{-1}$

PREPARATION 5

To a mixture of (E,E)-4-ethyl-2,4-hexadien-1-ol (1.0 g), triphenylphosphine (2.29 g), phthalimide (1.17 g), and tetrahydrofuran (30 ml) at room temperature was added a solution of diethyl azodicarboxylate (1.52 g) in tetrahydrofuran (5 ml). The mixture was stirred at room temperature for 2 days. The reaction mixture was diluted with dichloromethane, washed with water and brine, dried over anhydrous magnesium sulfate, and evaporated in vacuo. The residue was chromatographed on silica gel (hexane-dichloromethane, 2:3) to give 0.42 g of N-(4-ethyl-2,4-hexadien-1-yl)phthalimide as crystals.

IR (Nujol): 1770, 1715, 1610 $cm^{-1}$

NMR ($CDCl_3$, $\delta$): 0.95 (3H, t, J=8 Hz), 1.69 (3H, d, J=7 Hz), 2.18 (2H, q, J=8 Hz), 4.32 (2H, d, J=7 Hz), 5.50 (1H, q, J=7 Hz), 5.50–5.68 (1H, m), 6.20 (1H, d, J=16 Hz), 7.71 (2H, m), 7.84 (2H, m)

PREPARATION 6

A mixture of N-(4-ethyl-2,4-hexadien-1-yl)phthalimide (500 mg), hydrazine monohydrate (147 mg), and ethanol (5 ml) was refluxed for 40 minutes under nitrogen atmosphere. After cooling, the precipitate was filtered and washed with ethanol. Evaporation of the filtrate gave a crystalline residue which was dissolved in 1N sodium hydroxide solution and extracted with dichloromethane. The organic extract was washed with water and brine, dried over anhydrous sodium sulfate, and evaporated to give 4-ethyl-2,4-hexadien-1-ylamine (205 mg) as an oil. This oil was used in the next reaction without further purification. To a solution of crude 4-ethyl-2,4-hexadien-1-ylamine (205 mg) in dichloromethane (2 ml) at 0° C. was added dropwise acetic anhydride (335 mg). After one hour, the reaction mixture was evaporated to dryness. The residue was chromatographed on silica gel (2% methanol in dichloromethane) to give 1-acetylamino-4-ethyl-2,4-hexadiene (122 mg) as an oil.

IR (Neat): 3250, 1650, 1545 cm$^{-1}$

PREPARATION 7

To a mixture of (E,E)-1-acetoxy-4-ethyl-2,4-hexadiene (5.0 g), sodium azide (1.93 g), water (10 ml), and tetrahydrofuran (30 ml) was added tetrakis(triphenylphosphine)palladium(0) (0.71 g) under nitrogen atmosphere. The mixture was stirred at 60° C. for 12 hours. After cooling, the reaction mixture was extracted three times with ethyl acetate. The organic layer was washed with water and brine, dried over anhydrous magnesium sulfate, and evaporated in vacuo. The residue was chromatographed on silica gel(hexane) to give 2.1 g of an oil, which was a mixture of 1-azido-4-ethyl-2,4-hexadiene and other regioisomers. This oil was used in the next reaction without further purification.

IR (Neat): 2200, 1640, 1450, 1240 cm$^{-1}$

PREPARATION 8

A mixture of crude 1-azido-4-ethyl-2,4-hexadiene (2.0 g), triphenylphosphine (3.82 g), water (8 ml), and tetrahydrofuran (24 ml) was stirred at 60° C. for 1 hour 20 minutes. After the addition of 2N sodium hydroxide solution (15 ml), the mixture was stirred at 50° C. for 1 hour. The organic layer was separated and the aqueous layer was extracted with a mixture of benzene and tetrahydrofuran (1:1). The extracts combined were dried over anhydrous sodium sulfate and evaporated in vacuo. The crude oil obtained was dissolved in dichloromethane (20 ml) containing triethylamine (2.5 ml). To this solution cooled to 0° C. was added nicotinic acid chloride hydrochloride (2.3 g) in small portions over a period of 1 hour. After being stirred for additional 1.5 hours, the reaction mixture was washed with water, dried over anhydrous magnesium sulfate, and evaporated in vacuo. The residue was chromatographed on silica gel (2% methanol-dichloromethane) to give 2.80 g of an oil, which was a mixture of desired N-(4-ethyl-2,4-hexadien-1-yl)-3-pyridinecarboxamide and other regioisomers. This oil was used in the next reaction without further purification.

IR (Neat): 3280, 1640, 1590, 1540 cm$^{-1}$

PREPARATION 9

A mixture of N-(4-ethyl-2,4-hexadien-1-yl)phthalimide (5.0 g), hydrazine monohydrate (2.45 g), and ethanol (150 ml) was refluxed for 1.5 hours under nitrogen atmosphere. After cooling, the precipitate was filtered and washed with ethanol. Evaporation of the filtrate gave a crystalline residue which was dissolved in 1N sodium hydroxide solution and extracted with dichloromethane. The organic extract was washed with water and brine, dried over anhydrous sodium sulfate, and evaporated to give crude 4-ethyl-2,4-hexadien-1-ylamine (2.59 g) as an oil. The crude oil was dissolved in dichloromethane (30 ml) containing triethylamine (6.28 g). To this solution cooled to 0° C. was added nicotinic acid chloride hydrochloride (3.41 g) in small portions during 10 minutes. After 30 minutes, triethylamine (4.19 g) and nicotinic acid chloride hydrochloride (0.79 g) were added and the mixture was stirred for 30 minutes at 0° C. The reaction mixture was diluted with dichloromethane, washed with water and brine, dried over anhydrous magnesium sulfate, and evaporated in vacuo. The residue was chromatographed on silica gel (2% methanol-dichloromethane) to give a mixture of N-[(2E,4E) and (2Z,4E)-4-ethyl-2,4-hexadien-1-yl]-3-pyridinecarboxamide (4.6 g) which crystallized on standing.

IR (Nujol) νmax: 3300, 1630, 1590, 1540 cm$^{-1}$

PREPARATION 10

A mixture of N-(4-ethyl-2,4-hexadien-1-yl)phthalimide (3.0 g), hydrazine monohydrate (0.88 g), and ethanol (30 ml) was refluxed for 40 minutes under nitrogen atmosphere. After cooling, the precipitate was filtered and washed with ethanol. Evaporation of the filtrate gave a crystalline residue which was dissolved in 1N sodium hydroxide solution and extracted with dichloromethane. The organic extract was washed with water and brine, dried over anhydrous sodium sulfate, and evaporated to give 4-ethyl-2,4-hexadien-1-ylamine as an oil. To a mixture of crude 4-ethyl-2,4-hexadien-1-ylamine, triethylamine (1.79 g), and dichloromethane (30 ml) at 0° C. was added dropwise dimethylsulfamoyl chloride (2.03 g) during 10 minutes. After 30 minutes, triethylamine (0.6 g) and dimethylsulfamoyl chloride (0.85 g) were added to the reaction mixture. After 1 hour at 0° C., the reaction mixture was washed with water and aqueous sodium hydrogen carbonate solution, dried over anhydrous magnesium sulfate, and evaporated in vacuo. The residue was chromatographed on silica gel (dichloromethane-hexane, 7:3) to give N,N-dimethyl-N'-(4-ethyl-2,4-hexadien-1-yl)sulfamide (924 mg) as an oil.

IR (Neat): 3300, 1645, 1450, 1325 cm$^{-1}$

PREPARATION 11

To a solution of crude 4-ethyl-2,4-hexadien-1-ylamine (1.38 g) and isopropyl N-cyano-3-pyridinecarboximidate (1.74 g) in methanol (35 ml) at room temperature was added 28% sodium methoxide in methanol (2.13 g). After 10 minutes, the mixture was diluted with water and extracted three times with dichloromethane. The organic layer was washed with brine, dried over anhydrous sodium sulfate, and evaporated in vacuo. The residue was chromatographed on silica gel (5% methanol in dichloromethane) to give N-cyano-N'-(4-ethyl-2,4-hexadien-1-yl)-3-pyridinecarboximidamide (1.89 g) as an oil.

IR (Neat): 3230, 3080, 2180, 1580 cm$^{-1}$

PREPARATION 12

6-(4-Ethyl-2,4-hexadien-1-yl)thiopurine was prepared in a similar manner to that of Preparation 5 as an oil.

IR (Neat): 3250, 1570, 1530 cm$^{-1}$

NMR (CDCl$_3$, δ): 0.96 (3H, t, J=8 Hz), 1.70 (3H, d, J=7 Hz), 2.21 (2H, q, J=8 Hz), 4.1–4.3 (2H, m), 5.49 (1H, q, J=7 Hz), 5.6–5.9 (1H, m), 6.26 (1H, d, J=16 Hz), 8.31 (1H, s), 8.78 (1H, s)

PREPARATION 13

1-Phenyl-5-(4-ethyl-2,4-hexadien-1-yl)thiotetrazole was prepared in a similar manner to that of Preparation 5 as an oil.

IR (Neat): 2960, 1640, 1595, 1495, 1410, 1385 cm$^{-1}$

NMR (CDCl$_3$, δ): 0.94 (3H, t, J=8 Hz), 1.70 (3H, d, J=7 Hz), 2.19 (2H, q, J=8 Hz), 4.11 (2H, d, J=8 Hz), 5.53 (1H, q, J=7 Hz), 5.6–5.9 (1H, m), 6.24 (1H, d, J=16 Hz), 7.5–7.7 (5H, m)

PREPARATION 14

1-Methyl-2-(4-ethyl-2,4-hexadien-1-yl)thioimidazole was prepared in a similar manner to that of Preparation 5 as an oil.

IR (Nujol): 2995, 1640, 1505, 1410 cm$^{-1}$

NMR (CDCl$_3$, δ): 0.9–1.1 (3H, m), 1.6–1.8 (3H, m), 2.1–2.3 (2H, m), 3.60 (3H, s), 3.6–3.8 (2H, m), 5.39 (1H, q, J=7 Hz), 5.5–5.8 (1H, m), 5.89 (⅔H, d, J=16 Hz), 6.34 (⅓H, d, J=16 Hz), 6.91 (1H, d, J=1 Hz), 7.07 (1H, d, J=1 Hz)

PREPARATION 15

1-Methyl-5-(4-ethyl-2,4-hexadien-1-yl)thiotetrazole was prepared in a similar manner to that of Preparation 5 as an oil.

IR (Nujol): 2950, 1640, 1450, 1390 cm$^{-1}$

NMR (DMSO-d$_6$, δ): 0.88 (3H, t, J=8 Hz), 1.66 (3H, d, J=7 Hz), 2.18 (2H, q, J=8 Hz), 3.94 (3H, s), 3.99 (2H, d, J=11 Hz), 5.4–5.8 (2H, m), 6.14 (1H, d, J=16 Hz)

PREPARATION 16

5-Methyl-2(4-ethyl-2,4-hexadien-1-yl)thio-1,3,4-thiadiazole was prepared in a similar manner to that of Preparation 5 as an oil.

IR (Nujol): 2950, 1640, 1600, 1500 cm$^{-1}$

PREPARATION 17

2-(4-Ethyl-2,4-hexadien-1-yl)thiobenzothiazole was prepared in a similar manner to that of Preparation 5 as an oil.

IR (Nujol): 2970, 2940, 1640, 1420, 1240 cm$^{-1}$

NMR (DMSO-d$_6$, δ): 0.8–1.1 (3H, m), 1.6–1.9 (3H, m), 2.16 (2H, q, J=7 Hz), 4.11 (1.4H, d, J=7 Hz), 4.17 (0.6H, d, J=7 Hz), 5.3–6.0 (2H, m), 6.29 (0.7H, d, J=16 Hz), 6.75 (0.3H, d, J=16 Hz), 7.3–7.5 (2H, m), 7.94 (1H, d, J=8 Hz), 8.02 (1H, d, J=8 Hz)

PREPARATION 18

2-(4-Ethyl-2,4-hexadien-1-yl)thiopyrimidine was prepared in a similar manner to that of Preparation 5 as an oil.

IR (Nujol): 1565, 1545, 1200 cm$^{-1}$

NMR (CDCl$_3$, δ): 0.97 (3H, t, J=8 Hz), 1.70 (3H, d, J=7 Hz), 2.25 (2H, q, J=8 Hz), 3.90 (2H, d, J=7 Hz), 5.48 (1H, q, J=7 Hz), 5.6–5.9 (1H, m), 6.20 (1H, d, J=16 Hz), 6.9–7.0 (1H, m), 8.57 (2H, d, J=5 Hz)

PREPARATION 19

To a solution of diisopropylamine (40.5 g) in tetrahydrofuran (160 ml) at −10° C. was added a solution of n-butyllithium (1.66M in hexane solution, 241 ml) under nitrogen atmosphere. The mixture was stirred for 20 minutes and then 1-(N-tert-butyl)butylimine (50.9 g) was added at the same temperature. Stirring was continued for 20 minutes and then cooled to −65° C. A solution of isobutanal (28.8 g) in tetrahydrofuran (120 ml) was added to the solution. The reaction mixture was kept at −65° C. for 90 minutes, then warmed slowly to room temperature and stirred overnight. The resultant mixture was poured into a saturated aqueous oxalic acid solution (1.5 l) and the mixture was stirred for one hour. The organic layer was separated and the aqueous layer was extracted with ethyl acetate (300 ml×2). The combined organic layers were washed with brine, dried over anhydrous magnesium sulfate and evaporated in vacuo. The residue was distilled to give (E)-2-ethyl-4-methyl-2-pentenal (35.7 g) : bP 30°~55° C. at 1.0~10 mmHg.

IR (Neat): 2970, 1690, 1640, 1460 cm$^{-1}$

NMR (CDCl$_3$, δ): 0.8–1.2 (9H, m), 2.26 (2H, q, J=8 Hz), 2.6–3.0 (1H, m), 6.22 (1H, d, J=10 Hz), 9.34 (1H, s)

PREPARATION 20

To a 28 wt % solution of sodium methoxide in methanol (59.4 g) at 20° C. were added dropwise diethyl phosphonoacetic acid ethyl ether (58.4 g) and (E)-2-ethyl-4-methyl-2-pentenal (29.9 g) subsequently under nitrogen atmosphere. The reaction mixture was stirred at room temperature for 3 hours and poured into ice-water and extracted with chloroform. The extract was washed with brine, dried over anhydrous magnesium sulfate, and evaporated in vacuo. The residue was chromatographed on silica gel (10% ethyl acetate-hexane) to give 35.7 g of methyl (E,E)-4-ethyl-6-methyl-2,4-heptadienoate as an oil.

IR (Neat) : 2950, 1720, 1625 cm$^{-1}$

NMR (CDCl$_3$, δ): 1.01 (6H, d, J=7 Hz), 1.02 (3H, t, J=8 Hz), 2.26 (2H, q, J=8 Hz), 2.5–2.8 (1H, m), 3.76 (3H, s), 5.65 (1H, d, J=10 Hz), 5.82 (1H, 16 Hz), 7.21 (1H, d, J=16 Hz)

PREPARATION 21

To a suspension of lithium aluminum hydride (5.41 g) in ethyl ether (550 ml) was added a solution of methyl (E,E)-4-ethyl-6-methyl-2,4-heptadienoate (35 g) in ethyl ether while keeping the temperature below 30° C. When addition was completed, the mixture was allowed to stir at room temperature for one hour. To this resultant mixture at 10° C. were added dropwise ethyl acetate (100 ml) and a saturated solution of potassium sodium tartrate (50 ml). The separated organic layer was washed with brine, dried over anhydrous magnesium sulfate, and evaporated to give 4-ethyl-6-methyl-2,4-heptadiene-1-ol (23.98 g) as an oil.

IR (Neat): 3300, 2950, 1640 cm$^{-1}$

NMR (CDCl$_3$, δ): 0.98 (6H, d, J=7 Hz), 1.03 (3H, t, J=8 Hz), 2.25 (2H, q, J=8 Hz), 2.5–2.7 (1H, m), 4.18 (2H, dd, J=1 Hz, 6 Hz), 5.25 (1H, d, J=10 Hz), 5.7–5.9 (1H, m), 6.11 (1H, dd, J=1 Hz, 16 Hz)

PREPARATION 22

To a solution of (E,E)-4-ethyl-6-methyl-2,4-heptadien-1-ol (23.8 g) in pyridine (61.4 g) at 0° C. was added dropwise acetic anhydride (50.9 g). After two hours, the reaction mixture was diluted with dichloromethane. The solution was washed with water and brine, dried over anhydrous magnesium sulfate, and evaporated in vacuo. The residue was chromatographed on silica gel (3% ethyl acetate-hexane) to give (E,E)-1-acetoxy-4-ethyl-6-methyl-2,4-heptadiene (24.11 g) as an oil.

IR (Neat): 2970, 1740, 1230 cm$^{-1}$

NMR (CDCl$_3$, δ): 0.9–1.2 (9H, m), 2.08 (3H, s), 2.23 (2H, q, J=8 Hz), 2.5–2.8 (1H, m), 4.64 (2H, d, J=6 Hz), 5.28 (1H, d, J=10 Hz), 5.6–5.8 (1H, m), 6.16 (1H, dd, J=1, 16 Hz)

PREPARATION 23

N-(4-Ethyl-6-methyl-2,4-heptadien-1-yl)phthalimide was prepared in a similar manner to that of Preparation 4 as an oil.

IR (Neat): 2970, 1770, 1715, 1610 cm$^{-1}$

NMR (DMSO-d$_6$, δ): 0.8–1.1 (9H, m), 2.0–2.3 (2H, m), 2.5–2.7 (1H, m), 4.2–4.3 (2H, m), 5.21 (1H, d, J=10 Hz), 5.5–5.7 (1H, m), 6.01 (1H, d, J=16 Hz), 7.0–8.0 (4H, m)

PREPARATION 24

A mixture of N-(4-ethyl-6-methyl-2,4-heptadiene-1-yl)phthalimide (17.62 g), hydrazine monohydrate (9.9 g), and ethanol (700 ml) was refluxed for 90 minutes under nitrogen atmosphere. The reaction mixture was evaporated in vacuo. The residue was dissolved in 10% aqueous potassium carbonate solution and extracted with ethyl acetate. The organic extract was washed with brine, dried over anhydrous magnesium sulfate, and evaporated to give 4-ethyl-6-methyl-2,4-heptadiene-1-ylamine as an oil.

IR (Neat): 1640, 1600,

NMR (DMSO-d$_6$, δ): 0.9–1.1 (9H, m), 2.18 (2H, q, J=8 Hz), 2.5–2.7 (1H, m), 3.2 (2H, br s), 5.15 (1H, d, J=10 Hz), 5.5–5.8 (1H, m), 5.95 (1H, d, J=16 Hz)

PREPARATION 25

To a solution of triethylamine (5.06 g) and 4-ethyl-6-methyl-2,4-heptadiene-1-ylamine (3.06 g) in dichloromethane (50 ml) at 0° C. was added nicotinic acid chloride hydrochloride (3.56 g) in small portions during 5 minutes. The mixture was stirred for 30 minutes at 0° C. The reaction mixture was washed with water and brine, dried over anhydrous magnesium sulfate, and evaporated in vacuo. The residue was dissolved in isopropyl ether (20 ml) and allowed to stand at 5° C. overnight to give 4.46 g of N-(4-ethyl-6-methyl-2,4-heptadiene-1-yl)-3-pyridinecarboxamide.

mp: 81°–83° C.

IR (Nujol): 3250, 1630, 1550, 1375, 1350

NMR (DMSO-d$_6$, δ): 0.9–1.1 (9H, m), 2.19 (2H, q, J=8 Hz), 2.5–2.7 (1H, m), 3.9–4.1 (2H, m), 5.21 (1H, d, J=10 Hz), 5.5–5.8 (1H, m), 6.04 (1H, d, J=16 Hz), 7.4–7.6 (1H, m), 8.10–8.30 (1H, m), 8.70–8.80 (1H, m), 8.84 (1H, t, J=5 Hz), 9.0–9.1 (1H, m)

PREPARATION 26

To a solution of triethylamine (2.22 g) and 4-ethyl-6-methyl-2,4-heptadiene-1-ylamine (3.07 g) in dichloromethane (50 ml) at 0° C. was added dropwise acetic anhydride (4.08 g). After one hour, the reaction mixture was washed with water and brine, dried over anhydrous magnesium sulfate, and evaporated in vacuo. The residue was chromatographed on silica gel (10% methanol-chloroform) to give 1-acetylamino-4-ethyl-6-methyl-2,4-heptadiene (3.86 g) as an oil.

IR (Neat): 3300, 1650, 1545 cm$^{-1}$

NMR (DMSO-d$_6$, δ): 0.8–1.1 (9H, m), 1.82 (3H, s), 2.17 (2H, q, J=7 Hz), 2.5–2.7 (1H, m), 3.6–3.8 (2H, m), 5.18 (1H, d, J=10 Hz), 5.4–5.6 (1H, m), 5.94 (1H, d, J=16 Hz), 7.95 (1H, br s)

PREPARATION 27

To a mixture of diethyl 2-aminoethylphosphonate (8.1 g), triethylamine (9.1 g) and dichloromethane (100 ml) at 5° C. was added nicotinic acid chloride hydrochloride (10.4 g) in small portions over a period of 15 minutes. After being stirred for additional 1.5 hours, the reaction mixture was washed with brine, dried over anhydrous magnesium sulfate, and evaporated in vacuo. The residue was chromatographed on silica gel (10% methanol in chloroform) to give 11.2 g of N-(2-diethoxyphosphoryl-ethyl)-3-pyridinecarboxamide as an oil.

IR (Neat): 3280, 1650, 1590, 1540 cm$^{-1}$

NMR (CDCl$_3$, δ): 1.34 (6H, t, J=7.1 Hz), 2.0–2.3 (2H, m), 3.7–3.9 (2H, m), 4.0–4.3 (4H, m), 7.37 (1H, dd, J=4.8, 7.9 Hz), 7.69 (1H, br s), 8.1–8.21 (1H, m), 8.7–8.8 (1H, m), 9.08 (1H, d, J=2.0 Hz)

PREPARATION 28

To a solution of N-(2-diethoxyphosphorylethyl)-3-pyridinecarboxamide (5.73 g) in tetrahydrofuran (40 ml) at −70° C. was added dropwise a solution of lithium diisopropylamide (39 ml, 1.55M solution in tetrahydrofuran/hexane) over a period of 20 minutes. The solution was stirred for additional 10 minutes under a nitrogen atmosphere. The solution was treated with a solution of 2-methyl-2-pentanal (2.55 g) in tetrahydrofuran (10 ml) at −70° C. and then allowed to warm slowly to room temperature over 2 hours. After stirring 2 hours, the reaction mixture was diluted with brine, extracted with ethyl acetate, dried over anhydrous magnesium sulfate and evaporated in vacuo. The residue was chromatographed on silica gel (5% methanol in chloroform) to give N-(2-diethoxyphosphoryl-3-hydroxy-4-methyl-4-hepten-1-yl)-3-pyridinecarboxamide as an oil.

IR (Neat): 3300, 1650, 1540, 1220 cm$^{-1}$

NMR (CDCl$_3$, δ): 0.9–1.1 (3H, m), 1.2–2.5 (6H, m), 1.62 (2H, s), 1.68 (1H, s), 2.0–2.2 (2H, m), 2.3–2.6 (1H, m), 3.4–4.2 (3H, m), 4.0–4.4 (4H, m), 5.49 (⅓H, t, J=7.1 Hz), 5.63 (⅔H, t, J=7.1 Hz), 7.3–7.6 (2H, m), 8.0–8.2 (1H, m), 8.6–8.8 (1H, m), 9.0–9.1 (1H, m)

PREPARATION 29

N-(2-Diethoxyphosphoryl-3-hydroxy-4-methyl-4-hexen-1-yl)-3-pyridinecarboxamide was prepared in a similar manner to that of Preparation 28 as an oil.

IR (Neat): 3250, 1630, 1590, 1520, 1355 cm$^{-1}$

NMR (CDCl$_3$, δ): 1.2–1.5 (6H, m), 1.6–1.7 (6H, m), 2.3–2.6 (1H, m), 2.4–4.6 (8H, m), 5.5–5.8 (1H, m), 7.3–7.5 (2H, m), 8.1–8.2 (1H, m), 8.72 (1H, d, J=4.8 Hz), 9.01 (1H, s)

PREPARATION 30

N-(2-Diethoxyphosphoryl-3-hydroxy-4-isopropyl-4-hexen-1-yl)-3-pyridinecarboxamide was prepared in a similar manner to that of Preparation 28 as an oil.

IR (Neat) : 3300, 1650, 1540 cm$^{-1}$ (CDCl$_3$, δ): 0.9–1.2 (6H, m), 1.2–1.5 (6H, m), 1.72 (3H, d, J=6.8 Hz), 2.3–2.8 (2H, m), 3.5–5.3 (7H, m), 5.4–5.9 (1H, m), 7.2–7.4 (2H, m), 8.1–8.3 (1H, m), 8.7 (1H, br s), 9.0 (1H, br s)

PREPARATION 31

N-[3-(1-Cyclohexen-1-yl)-2-diethoxyphosphoryl-3-hydroxypropyl] -3-pyridinecarboxamide was prepared in a similar manner to that of Preparation 28 as an oil.

IR (Neat) : 3300, 1650, 1530 cm$^{-1}$

NMR (CDCl$_3$, δ): 1.2–1.3 (6H, m), 1.4–1.8 (4H, m), 1.9–2.2 (4H, m), 2.3–2.4 (1H, m), 3.4–4.5 (7H, m), 5.7–5.9 (1H, m), 7.38 (1H, dd, J=5.8, 7.9 Hz), 8.0–8.2 (1H, m), 8.7–8.8 (1H, m), 9.0–9.1 (1H, m)

PREPARATION 32

N-[2-Diethoxyphosphoryl-3-(5,6-dihydro-2H-pyran-3-yl)-3-hydroxypropyl]-3-pyridinecarboxamide was prepared in a similar manner to that of Preparation 28 as an oil.

IR (Neat): 3250, 1650, 1590, 1540

NMR (CDCl$_3$, δ): 1.2–1.4 (6H, m), 2.0–2.4 (3H, m), 3.6–3.9 (2H, m), 4.0–4.6 (9H, m), 5.9–6.0 (1H, m), 7.3–7.8 (2H, m), 8.1–8.2 (1H, m), 8.72 (1H, dd, J=1.4, 4.8 Hz), 9.0–9.1 (1H, m)

PREPARATION 33

A mixture of diethyl 2-aminoethylphosphonate (12.5 g), isonicotinic acid (10.2 g), 1-hydroxybenzotriazole (11.2 g), 1-ethyl-3-(3-dimethylaminopropyl)carbodiimide hydrochloride (15.83 g) and dichloromethane (190 ml) was stirred at room temperature for 15 hours. The reaction mixture was washed with aqueous sodium bicarbonate and brine, dried over anhydrous magnesium sulfate, and evaporated in vacuo. The residue was chromatographed on silica gel (5% methanol-chloroform) to give 7.94 g of N-(2-diethoxyphosphorylethyl)-4-pyridinecarboxamide as an oil.

IR (Neat) : 3270, 1655, 1590, 1540 cm$^{-1}$

NMR (DMSO-d$_6$, δ): 1.23 (6H, t, J=7.0 Hz), 2.0–2.2 (2H, m), 3.4–3.6 (2H, m), 3.9–4.1 (4H, m), 7.74 (2H, dd, J=1.6, 4.5 Hz), 8.74 (2H, dd, J=1.6, 4.5 Hz), 8.91 (1H, t, J=5.4 Hz)

PREPARATION 34

N-(2-Diethoxyphosphoryl-3-hydroxy-6-methoxy-4-methyl- 4-hexen-1-yl)-4-pyridinecarboxamide was prepared in a similar manner to that of Preparation 28 as an oil.

IR (Neat): 3300, 1600, 1550 cm$^{-1}$

NMR (CDCl$_3$, δ): 1.2–1.5 (6H, m), 1.6–1.9 (3H, m), 2.3–2.6 (1H, m), 3.34 (3H, d, J=3.72 Hz), 3.7–4.4 (8H, m), 4.5–4.9 (1H, m), 5.5–6.0 (1H, m), 7.40 (1H, br s), 7.6–7.7 (2H, m), 8.7–8.8 (2H, m)

PREPARATION 35

To a solution of diethyl 2-aminoethylphosphonate (10.5 g), triethylamine (7.0 g) in dichloromethane (200 ml) at 0° C. was added dropwise acetic anhydride (7.1 g). After 20 hours at room temperature, the reaction mixture was diluted with brine, made basic with 5% aqueous potassium carbonate, and extracted twice with dichloromethane. The extract was dried over anhydrous magnesium sulfate and evaporated in vacuo. The residue was chromatographed on silica gel (5% methanol in chloroform) to give (12.1 g) of diethyl 2-acetylaminoethylphosphonate as an oil.

IR (Neat) : 3450, 3250, 1655, 1550 cm$^{-1}$

NMR (CDCl$_3$, δ): 1.34 (6H, t, J=7.1 Hz ), 1.9–2.1 (2H, m), 2.0 (3H, s), 3.4–3.7 (2H, m), 4.0–4.2 (4H, m), 6.5 (1H, br s)

PREPARATION 36

Diethyl 1-acetylamino-3-hydroxy-4-methyl-4 -heptenyl-2-phosphonate was prepared in a similar manner to that of Preparation 28 as an oil.

IR (Neat): 3250, 1660, 1645 cm$^{-1}$

NMR (CDCl$_3$, δ): 0.99 (3H, t, J=7.5 Hz), 1.3–1.5 (6H, m), 1.61 (2H, s), 1.65 (1H, s), 1.95 (1H, s), 1.98 (2H, s), 2.0–2.4 (3H, m), 3.1–3.8 (2H, m), 4.0–4.4 (6H, m), 5.4–5.6 (1H, m), 6.3 (⅓H, br s), 6.5 (⅔H, br s)

PREPARATION 37

A solution of N-(2-diethoxyphosphoryl 3-hydroxy-4-methyl-4-hepten-1-yl)-3-pyridinecarboxamide (4.23 g) and 1,8-diazabicyclo[5.4.0]undec-7-ene (2.0 g) in xylene (64 ml) was refluxed for 30 minutes under a nitrogen atmosphere. After cooling, the reaction mixture was treated with water, extracted with ethyl acetate, washed with brine, dried over anhydrous magnesium sulfate, and evaporated in vacuo. The residue was chromatographed on silica gel (5% methanol in chloroform) to give 1.92 g of an oil, which was a mixture of (2E,4E)- and (2Z,4E)-N-( 4-methyl-2,4-heptadien-1-yl)-3-pyridinecarboxamide. This oil was used in the next reaction without further purification.

IR (Neat) : 3300, 1660, 1640, 1590, 1540 cm$^{-1}$

NMR (CDCl$_3$, δ): 0.9–1.1 (3H, m), 1.72 (⅗H, s), 1.77 (⅗H, s), 2.0–2.2 (2H, m), 4.1–4.4 (2H, m), 5.3–5.7 (2H, m), 5.91 (½H, d, J=11.6 Hz), 6.25 (½H, d, J=15.6 Hz), 6.56 (1H, br s), 7.37 (1H, dd, J=4.9, 7.8 Hz), 8.1–8.2 (1H, m), 8.70 (1H, dd, J=1.5, 4.8 Hz), 8.9–9.1 (1H, m)

PREPARATION 38

N-(4-Methyl-2,4-hexadien-1-yl)-3-pyridinecarboxamide was prepared in a similar manner to that of Preparation 37 as an oil.

IR (Neat): 3250, 1630, 1590, 1520,, 1355 cm$^{-1}$

NMR (CDCl$_3$, δ): 1.6–1.9 (6H, m), 4.0–4.2 (2H, m), 5.5–6.6 (3H, m), 7.3–7.5 (1H, m), 8.1–8.3 (1H, m), 8.5–8.8 (2H, m), 9.0–9.1 (1H, m)

PREPARATION 39

N-(4-Isopropyl-2,4-hexadien-1-yl)-3-pyridinecarboxamide was prepared in a similar manner to that of Preparation 37 as an oil.

IR (Neat): 3270, 1640, 1540 cm$^{-1}$

NMR (CDCl$_3$, δ): 0.9–1.1 (6H, m), 1.6–1.8 (3H, m), 2.8–3.0 (1H, m), 4.1–4.3(2H, m), 5.2–6.5 (4H, m), 7.3–7.5 (1H, m), 8.0–8.2 (1H, m), 8.71 (1H, dd, J=1.4, 4.9 Hz), 8.9–9.1 (1H, m)

PREPARATION 40

N-[3-(1-Cyclohexen-1-yl)-2-propen-1-yl]-3-pyridinecarboxamide was prepared in a similar manner to that of Preparation 37 as an oil.

IR (Neat) : 3250, 1640, 1590, 1540 cm$^{-1}$

NMR (CDCl₃, δ): 1.5–1.8 (4H, m), 2.0–2.3 (4H, 4.1–4.4 (2H, m), 5.3–6.5 (4H, m), 7.3–7.5 (1H, m), 8.1–8.3 (1H, m), 8.72 (1H, dd, J=1.7, 4.9 Hz), 8.98 (1H, s)

PREPARATION 41

N-[3-(5,6-Dihydro-2H-pyran-3-yl)-2-propen-1-yl]-3-pyridinecarboxamide was prepared in a similar manner to that of Preparation 37 as an oil.

IR (Neat): 3300, 1640, 1590, 1540 cm⁻¹

NMR (CDCl₃, δ): 2.26 (2H, br s), 3.7–3.9 (2H, m), 4.1–4.4 (4H, m), 5.4–6.2 (3H, m), 6.6 (1H, br s), 7.39 (1H, dd, J=4.8, 7.9 Hz), 8.1–8.2 (1H, m), 8.71 (1H, d, J=7.9 Hz), 8.99 (1H, s)

PREPARATION 42

N-(6-Methoxy-4-methyl-2,4-hexadien-1-yl)-4-pyridinecarboxamide was prepared in a similar manner to that of Preparation 37 as an oil.

IR (Neat): 3300, 1650, 1600, 1540 cm⁻¹

NMR (CDCl₃, δ): 1.7–1.9 (3H, m), 3.3–3.4 (3H, m), 3.8–4.4 (4H, m), 5.4–6.4 (3H, m), 6.8 (1H, br s), 7.6–7.7 (2H, m), 8.6–8.8 (2H, m)

PREPARATION 43

1-Acetylamino-4-methyl-2,4-heptadiene was prepared in a similar manner to that of Preparation 37 as an oil.

IR (Neat): 3350, 1650, 1625 cm⁻¹

NMR (CDCl₃, δ): 0.9–1.1 (3H, m), 1.71 (³⁄₂H, s), 1.72 (³⁄₂H, s), 1.99 (3H, s), 1.9–2.2 (2H, m), 3.9–4.2 (2H, m), 5.2–6.3 (4H, m)

PREPARATION 44

To a 28 wt % solution of sodium methoxide in methanol (25.7 g) at 10° C. were added dropwise diethyl phosphonoacetic acid ethyl ester (25.3 g) and (E)-2-ethyl-2-pentenal (11.5 g) successively under a nitrogen atmosphere. The reaction mixture was stirred at room temperature for 3 hours, poured into chilled water and extracted with ethyl acetate. The extract was washed with brine, dried over anhydrous magnesium sulfate, and evaporated in vacuo. The residue was chromatographed on silica gel (dichloromethane) to give 13.4 g of methyl (E,E)-4-ethyl-2,4-heptadienoate as an oil.

IR (Neat): 3950, 1720, 1625 cm⁻¹

NMR (CDCl₃, δ): 0.9–1.1 (6H, m), 2.1–2.4 (4H, m), 3.75 (3H, s), 5.7–6.0 (2H, m), 7.23 (1H, dd, J=15.7 Hz)

PREPARATION 45

To a suspension of lithium aluminum hydride (2.38 g) in ethyl ether (160 ml) was added a solution of methyl (E,E)-4-ethyl-2,4-heptadienoate (13.2 g) in ethyl ether (100 ml) while keeping the temperature below 30° C. When addition was completed, the mixture was allowed to stir at room temperature for one hour. To this resultant mixture at 10° C. were added dropwise ethyl acetate (50 ml) and a saturated aqueous solution of potassium sodium tartrate (50 ml). The separated organic layer was washed with brine, dried over anhydrous magnesium sulfate, and evaporated to give (E,E)-4-ethyl-2,4-heptadien-1-ol (10.1 g) as an oil. This oil was used in the next reaction without further purification.

IR (Neat) : 3250, 2950 cm⁻¹

NMR (CDCl₃, δ): 0.9–1.1 (6H, m), 2.0–2.3 (4H, m), 4.18 (2H, d, J=6.1 Hz), 5.53 (1H, t, J=7.4 Hz), 5.6–5.8.(1H, m), 6.14 (1H, d, J=15.8 Hz)

PREPARATION 46

To a solution of (E,E)-4-ethyl-2,4-heptadien-1-ol (10.1 g) in pyridine (29 g) at 0° C. was added dropwise acetic anhydride (22.2 g). After two hours at room temperature, the reaction mixture was evaporated in vacuo. The residue was diluted with ethyl acetate, washed with 0.5N hydrochloric acid and brine, dried over anhydrous magnesium sulfate, and evaporated in vacuo. The residue was chromatographed on silica gel (5% ethyl acetate in hexane) to give (E,E)-1-acetoxy-4-ethyl-2,4-heptadiene (9.75 g) as an oil.

IR (Neat) : 1740 cm⁻¹

NMR (CDCl₃, δ): 0.9–1.1 (6H, m), 2.07 (3H, s), 2.1–2.4 (4H, m), 4.61 (2H, d, J=7.1 Hz), 5.4–5.8 (2H, m), 6.18 (1H, d, J=15.7 Hz)

PREPARATION 47

A mixture of (E,E)-1-acetoxy-4-ethyl-2,4-heptadiene (9.6 g), potassium phthalimide (9.9 g), tetrakis(triphenyl phosphine)palladium(0) (1.0 g), and N,N-dimethylformamide (85 ml) was stirred at 100° C. for 6 hours under a nitrogen atmosphere. After cooling, the precipitate was filtered and washed with N,N-dimethylformamide. The filtrate was evaporated in vacuo. The residue was diluted with dichloromethane, washed with water and brine, dried over anhydrous magnesium sulfate, and evaporated in vacuo. The residue was chromatographed on silica gel (5% ethyl acetate in toluene) to give a mixture of N-[(2E,4E)- and (2Z,4E)-4-ethyl-2,4-heptadien-1-yl]phthalimide (10.1 g). This product was used in the next reaction without further purification.

IR (Nujol): 3450, 1720 cm⁻¹

NMR (DMSO-d₆, δ): 0.8–1.1 (6H, m), 1.9–2.3 (4H, m), 4.2–4.4 (2H, m), 5.2–5.8 (2H, m), 6.06 (²⁄₃H, d, J=15.9 Hz), 6.52 (¹⁄₃H, d, J=15.8 Hz), 7.8–8.0 (4H, m)

PREPARATION 48

A mixture of N-(4-ethyl-2,4-heptadien-1-yl)-phthalimide (9.6 g), hydrazine monohydrate (4.5 g), and ethanol (900 ml) was refluxed for 90 minutes under a nitrogen atmosphere. The reaction mixture was evaporated in vacuo. The residue was dissolved in 10% aqueous potassium carbonate solution and extracted with ethyl acetate. The organic extract was washed with brine, dried over anhydrous magnesium sulfate, and evaporated to give 5 g of an oil, which was a mixture of (2E,4E)- and (2Z,4E)-4-ethyl-2,4-heptadienylamine. This oil was used in the next reaction without further purification.

IR (Neat): 3300, 1620 cm⁻¹

NMR (CDCl₃, δ): 0.9–1.1 (6H, m), 2.0–2.3 (4H, m), 3.5–3.7 (2H, m), 4.98 (2H, s), 5.3–5.9 (2H, m), 6.16 (²⁄₃H, 15.7 Hz), 6.60 (¹⁄₃H, 15.7 Hz)

PREPARATION 49

To a solution of triethylamine (3.24 g) and 4-ethyl-2,4-heptadienylamine (2.2 g) in dichloromethane (50 ml) at 0° C. was added dropwise acetic anhydride (3.27 g). After one hour, the reaction mixture was washed with water and brine, dried over anhydrous magnesium sulfate, and evaporated in vacuo. The residue was chromatographed on silica gel (5% methanol-chloroform) to give 2.9 g of an oil, which was a mixture of (2E,4E)- and (2Z,4E)-1-acetylamino- 4-ethyl-2, 4-heptadiene. This oil was used in the next reaction without further purification.

IR (Neat): 3240, 1650, 1545 cm$^{-1}$

NMR (DMSO-d$_6$, δ): 0.8–1.1 (6H, m), 1.82 (3H, s), 2.0–2.3 (4H, m), 3.6–3.9 (2H, m), 5.2–5.5 (2H, m), 5.98 (⅔H, 15.8 Hz), 6.42 (⅓H, 15.8 Hz), 8.0 (1H, br s)

PREPARATION 50

To a solution of triethylamine (4.05 g) and 4-ethyl-2,4-heptadienylamine (2.2 g) in dichloromethane (40 ml) at 0° C. was added nicotinic acid chloride hydrochloride (3.13 g) in small portions during 5 minutes. The mixture was stirred for 30 minutes at 0° C. The reaction mixture was washed with water and brine, dried over anhydrous magnesium sulfate, and evaporated in vacuo. The residue was chromatographed on silica gel (5% methanol-chloroform) to give a mixture of N-[(2E,4E)- and (2Z,4E)-4-ethyl-2,4-heptadien-1-yl)-3-pyridinecarboxamide.

mp: 61°–63° C.

IR (Neat): 3250, 1650, 1635, 1590, 1540 cm$^{-1}$

NMR (DMSO-d$_6$, δ): 0.9–1.1 (6H, m), 1.9–2.3 (4H, m), 3.9–4.1 (2H, m), 5.3–5.8 (2H, m), 6.06 (⅔H, d, J=15.8 Hz), 6.41 (⅓H, d, J=15.8 Hz), 7.4–7.6 (1H, m), 8.1–8.3 (1H, m), 8.70 (1H, dd, J=1.6, 4.4 Hz), 8.85 (1H, t, J=5.9 Hz), 9.0–9.1 (1H, m)

PREPARATION 51

To a solution of 4-ethyl-2,4-hexadien-1-ylamine (0.2 g) in dichloromethane (2 ml) was added dropwise trimethylsilyl isocyanate (0.25 ml) at room temperature. After 8 hours, trimethylsilyl isocyanate (0.25 ml) was added to the solution. After 2 days, the reaction mixture was washed with water, dried over anhydrous magnesium sulfate and evaporated in vacuo. The residue was chromatographed on silica gel (2% methanol-chloroform) to give N-[(2E,4E)- and (2Z,4E)-4-ethyl-2,4-hexadien-1-yl]urea (0.08 g) which crystallized on standing. This product was used in the next reaction without further purification.

IR (Nujol): 3400, 3325, 1645, 1595, 1550 cm$^{-1}$

NMR (DMSO-d$_6$, δ): 0.9–1.0 (3H, m), 1.68 (3H, d, J=7 Hz), 2.1–2.2 (2H, m), 3.6–3.7 (2H, m), 5.3–6.5 (6H, m)

PREPARATION 52

To a mixture of 4-ethyl-2,4-hexadien-1-ylamine (4.85 g), triethylamine (4.54 ml) and dichloromethane (50 ml) at 0° C. was added 3,4-pyridinedicarboxylic anhydride (4.82 g). The reaction mixture was stirred at 0° C. for 4 hours and then allowed to come to room temperature. After 14 hours, the reaction mixture was evaporated in vacuo. The oily residue obtained was chromatographed on silica gel (10% methanol-chloroform: 5.8N ammonia in ethanol, 100:4) to give 3-{N-[(2E,4E)- and (2Z,4E)-4-ethyl-2,4-hexadien-1-yl]carbamoyl}pyridine-2-carboxylic acid (10.38 g) as an oil.

IR (Neat): 3225, 2450, 1730, 1620, 1570 cm$^{-1}$

NMR (DMSO-d$_6$, δ): 0.9–1.1 (3H, m), 1.69 (3H, m), 2.1–2.2 (2H, m), 3.9–4.0 (2H, m), 5.3–5.8 (2H, m), 6.11 (0.7H, d, J=16 Hz), 6.56 (0.3H, d, J=16 Hz), 7.39 (0.3H, d, J=5 Hz), 7.48 (0.7H, d, J=5 Hz), 8.55 (1H, m), 8.77 (0.3H, s), 8.84 (0.7H, s), 10.00 (1H, m)

PREPARATION 53

To a solution 3-{N-[(2E,4E)- and (2Z,4E)-4-ethyl-2,4-hexadien-1-yl]carbamoyl}pyridine-2-carboxylic acid (9.8 g) and N-methylmorpholine (3.61 g) in dichloromethane (60 ml) at 0° C. was added dropwise a solution of chloroformic acid isobutyl ester (4.88 g) in dichloromethane (40 ml). After 10 minutes, ethanolic 5.6N ammonia solution (12.8 ml) was added dropwise to the solution and the mixture was stirred for 30 minutes. The reaction mixture was washed twice with brine, dried over anhydrous magnesium sulfate, and evaporated in vacuo. The residue was chromatographed on silica gel (4% methanol-chloroform) to give N-[(2E,4E)- and (2Z,4E)-4-ethyl-2,4-hexadien-1-yl]-3-carbamoyl-4-pyridinecarboxamide (2.95 g) as an oil.

IR (Nujol): 3250, 1650, 1615, 1585, 1550 cm$^{-1}$

NMR (DMSO-d$_6$, δ): 0.9–1.1 (3H, m), 1.68 (3H, d, J=7 Hz), 2.1–2.3(2H, m), 3.8–4.0 (2H, m), 5.3–5.8 (2H, m), 6.14 (0.8H, d, J=16 Hz), 6.57 (0.2H, d, J=16 Hz), 7.44 (1H, dd, J=5, 8 Hz), 7.59 (1H, br d, J=10 Hz), 8.00 (1H, br s), 8.6–7.3 (3H, m)

PREPARATION 54

To a solution of 4-ethyl-2,4-hexadien-1-ylamine (1.5 g) in dichloromethane (15 ml) containing triethylamine (5.0 ml) at 0° C. was added isonicotinoyl chloride hydrochloride (3.41 g) in small portions during 15 minutes. After 1 hour, the reaction mixture was diluted with water. The separated organic phase was washed with water and brine, dried over anhydrous magnesium sulfate, and evaporated in vacuo. The residue was chromatographed on silica gel (2% methanol-chloroform) to give a mixture of N-[(2E,4E)- and (2Z,4E)-4-ethyl-2,4-hexadien-1-yl]-4-pyridinecarboxamide (2.0 g) as an oil.

IR (Neat): 3250, 1640, 1595, 1540 cm$^{-1}$

NMR (DMSO-d$_6$, δ): 0.9–1.1 (3H, m), 1.71 (3H, d, J=7 Hz), 2.0–2.3 (2H, m), 4.1–4.2 (2H, m), 5.4–5.8 (2H, m), 6.11 (0.7H, d, J=16 Hz), 6.58 (0.3H, d, J=16 Hz), 7.00 (1H, br s), 7.6–7.7 (2H, m), 8.69 (2H, d, J=5 Hz)

PREPARATION 55

A solution of 2-methyl-3-pyridinecarboxylic acid (1.66 g), 1-ethyl-3-(3-dimethylaminopropyl)carbodiimide hydrochloride (2.12 g), and N-hydroxybenzotriazole (1.63 g) in dichloromethane (25 ml) was stirred at 0° C. for 15 minutes. A solution of 4-ethyl-2,4-hexadien-1-ylamine (1.26 g) in dichloromethane (6.3 ml) was added dropwise to the solution over a period of 10 minutes. The mixture was stirred at 0° C. for 30 minutes and then at room temperature for 3 hours. The reaction mixture was diluted with aqueous sodium hydrogen carbonate. The organic phase separated was washed with water and brine, dried over anhydrous magnesium sulfate, and evaporated in vacuo. The residue was chromatographed on silica gel (4% methanol-chloroform) to give N-[(2E,4E)- and (2Z,4E)-4 -ethyl-2,4-hexadien-1-yl]-2-methyl-3-pyridinecarboxamide 2.38 g) as an oil.

NMR (DMSO-d$_6$, δ): 0.9–1.1 (3H, m), 1.72 (3H, d, J=7 Hz), 2.1–2.3 (2H, m), 2.61 (3H, s), 4.0–4.1 (2H, m), 5.4–5.8 (2H, m), 6.12 (0.8H, d, J=16 Hz), 6.40 (1H, br s), 6.58 (0.2H, d, J=16 Hz), 7.10 (1H, dd, J=5, 8 Hz), 7.6–7.7 (1H, m), 8.46 (1H, dd, J=2, 5 Hz)

PREPARATION 56

N-[(2E, 4E)- and (2Z, 4E)-4-Ethyl-2,4-hexadien-1-yl]-2-methylthio-3-pyridincarboxamide was prepared in a similar manner to that of Preparation 55 as an oil.

(DMSO-d$_6$, δ): 0.9–1.0 (3H, m), 1.6–1.7 (3H, m), 2.1–2.3 (2H, m), 2.43 (3H, s), 3.9–4.0 (2H, m), 5.4–5.8 (2H, m), 6.10 (⅔H, d, J=16 Hz), 6.56 (⅓H, d, J=16 Hz), 7.1–7.2 (1H, m), 7.7–7.8 (1H, m), 8.5–8.6 (1H, m), 8.64 (1H, br s)

PREPARATION 57

N-[(2E,4E)- and (2Z,4E)-4-Ethyl-2,4-hexadien-1-yl]-2-chloro-3-pyridinecarboxamide was prepared in a similar manner to that of Preparation 55 as an oil.

IR (Neat) : 3250, 1650, 1580, 1540 cm$^{-1}$ (DMSO-d$_6$, δ): 1.0–1.1 (3H, m), 1.7–1.8 (3H, m), 2.2–2.3 (2H, m), 4.1–4.2 (2H, m), 5.4–5.8 (2H, m), 6.16 (0.6H, d, J=16 Hz), 6.62 (0.4H, d, J=16 Hz), 6.75 (1H, br s), 7.3–7.4 (1H, m), 8.0–8.1 (1H, m), 8.4–8.6 (1H, m)

PREPARATION 58

N-[(2E,4E)- and (2Z,4E)-4-Ethyl-2,4-hexadien-1-yl]-2-hydroxy-3-pyridinecarboxamide was prepared in a similar manner to that of Preparation 55 as an oil.

NMR (DMSO-d$_6$, δ): 0.9–1.1 (3H, m), 1.67 (3H, d, J=7 Hz), 2.1–2.2 (2H, m), 4.0–4.1 (2H, m), 5.3–5.8 (2H, m), 6.08 (0.7H, d, J=16 Hz), 6.49 (1H, t, J=6 Hz), 6.55 (0.3H, d, J=16 Hz), 7.02 (1H, dd, J=2, 6 Hz), 8.3–8.4 (1H, m), 9.8–9.9 (1H, m), 12.52 (1H, br s)

PREPARATION 59

To a mixture of 3-quinolinecarboxylic acid (3.32 g), 1-ethyl-3-(3-dimethylaminopropyl)carbodiimide hydrochloride (3.37 g), N-hydroxybenzotriazole (2.6 g) and dichloromethane (50 ml) at 0° C. was added triethylamine (2.3 ml). After 15 minutes, a solution of 4-ethyl-2,4-hexadien-1-ylamine (2.0 g) in dichloromethane (10 ml) was added dropwise to the solution over a period of 10 minutes. The mixture was stirred at 0° C. for 30 minutes and then at room temperature overnight. The reaction mixture was diluted with aqueous sodium hydrogen carbonate. The separated organic phase was washed with water and brine, dried over anhydrous magnesium sulfate, and evaporated in vacuo. The residue was chromatographed on silica gel (1% methanol-chloroform) to give N-[(2E,4E)- and (2Z,4E)-4-ethyl-2,4-hexadien-1-yl]-3-quinolinecarboxamide (3.18 g) as an oil.

PREPARATION 60

N-[(2E,4E)- and (2Z,4E)-4-Ethyl-2,4-hexadien-1-yl]-6-methyl-3-pyridinecarboxamide was prepared in a similar manner to that of Preparation 59 as an oil.

IR (CHCl$_3$): 3300, 1640, 1600, 1540 cm$^{-1}$

NMR (DMSO-d$_6$, δ): 0.8–1.1 (3H, m), 1.68 (3H, d, J=7 Hz), 2.1–2.3 (2H, m), 2.52 (3H, s), 3.9–4.1 (2H, m), 5.3–5.8 (2H, m), 6.08 (⅔H, d, J=16 Hz), 6.54 (⅓H, d, J=16 Hz), 7.35 (1H, d, J=8 Hz), 8.11 (1H, dd, J=2, 8 Hz), 8.78 (1H, br t, J=6 Hz), 8.92 (1H, d, J=2 Hz)

PREPARATION 61

N-[(2E,4E)- and (2Z,2E)-4-Ethyl-2,4-hexadien-1-yl]-2-pyrazinecarboxamide was prepared in a similar manner to that of Preparation 59 as an oil.

IR (CHCl$_3$): 1670, 1580, 1525 cm$^{-1}$

NMR (DMSO-d$_6$, δ): 0.9–1.0 (3H, m), 1.67 (3H, d, J=7 Hz), 2.1–2.2 (2H, m), 4.0–4.1 (2H, m), 5.3–5.5 (1H, m), 5.6–5.8 (1H, m), 6.08 (0.7H, d, J=16 Hz), 6.54 (0.3H, d, J=16 Hz), 8.7–8.8 (1H, m), 8.89 (1H, d, J=2 Hz), 9.11 (1H, br t, J=6 Hz), 9.23 (1H, d, J=2 Hz)

PREPARATION 62

To a mixture of 4-ethyl-2,4-hexadien-1-ylamine (3.0 g), pyridine (5.8 ml) and dichloromethane (35 ml) at 0° C. was added dropwise methanesulfonyl chloride (6.58 g). The solution was stirred at 0° C. for 3 hours and then allowed to come to room temperature. After 14 hours, the reaction mixture was washed with water, dried over anhydrous magnesium sulfate, and evaporated in vacuo. The residual oil was dissolved in ethyl acetate. The ethyl acetate solution was washed with aqueous sodium hydrogen carbonate and water successively, dried over anhydrous magnesium sulfate, and evaporated in vacuo. The residue was chromatographed on silica gel (chloroform) to give N-[(2E,4E)- and (2Z,4E)-4-ethyl-2,4-hexadien-1-yl]methanesulfonamide as an oil. This product was used in the next reaction without further purification.

PREPARATION 63

N-[(2E,4E)- and (2Z,4E)-4-Ethyl-2,4-hexadien-1-yl]propionamide was prepared in a similar manner to that of Preparation 54.

PREPARATION 64

To a solution of triethylamine (8.1 g) and 4-ethyl-2,4-hexadienylamine (2.5 g) in dichloromethane (80 ml) at 5° C. was added dropwise a solution of 3-pyridinesulfonyl chloride hydrochloride (6.4 g) in dichloromethane (30 ml). After one hour, the reaction mixture was washed with water, aqueous sodium bicarbonate and brine. The organic layer was dried over anhydrous magnesium sulfate, and evaporated in vacuo. The residue was chromatographed on silica gel (3% methanol in chloroform) to give 2.7 g of an oil, which was a mixture of (2E,4E)- and (2Z,4E)-N-(4-ethyl-2,4-hexadien-1-yl)-3-pyridinesulfonamide. This oil was used in the next reaction without further purification.

IR (Neat): 3300, 1570, 1330 cm$^{-1}$

NMR (CDCl$_3$, δ): 0.8–1.0 (3H, m), 1.66 (3H, d, J=7.1 Hz), 2.0–2.2 (2H, m), 3.6–3.8 (2H, m), 5.0–5.6 (3H, m), 5.99 (¾H, d, J=15.7 Hz), 6.44 (¼H, d, J=15.7 Hz), 7.4–7.5 (1H, m), 8.1–8.2 (1H, m), 8.7–8.8 (1H, m), 9.08 (1H, d, J=1.6 Hz)

PREPARATION 65

To a solution of oxamic acid (8.9 g) and N-hydroxybenzotriazole (13.51 g) in N,N-dimethylformamide (90 ml) at 0° C. were added 1-ethyl-3-(3dimethylaminopropyl)carbodiimide hydrochloride (17.57 g) and 4-ethyl-2,4-hexadien-1-ylamine (10.44 g) successively. After stirring at the same temperature for 1 hour, the reaction mixture was diluted with water. The precipitate formed was filtered, washed with water and suspended in aqueous sodium hydrogen carbonate (100 ml). After 10 minutes of stirring, the precipitate was collected, washed with water, and dried to give N-[(2E,4E)- and (2Z,4E)-4-ethyl-2,4-hexadien-1-yl]oxamate.

IR (Nujol): 3400, 3300, 1645, 1525 cm$^{-1}$

NMR (DMSO-d$_6$, δ): 0.9–1.0 (3H, m), 1.67 (3H, d, J=7 Hz), 2.1–2.2 (2H, m), 3.7–3.9 (2H, m), 5.4–5.6 (2H, m), 5.99 (0.8H, d, J=16 Hz), 6.44 (0.2H, d, J=16 Hz), 7.77 (1H, br s), 8.05 (1H, br s), 8.82 (1H, br s)

PREPARATION 66

N-[(2E,4E)- and (2Z,4E)-4-Ethyl-2,4-hexadien-1-yl]-4-pyrimidinecarboxamide was prepared in a similar manner to that of Preparation 59 as an oil.

IR (CHCl$_3$): 3400, 1680, 1580, 1550, 1520 cm$^{-1}$

NMR (DMSO-d$_6$, δ): 0.9–1.0 (3H, m), 1.67 (3H, d, J=7 Hz), 2.0–2.2 (2H, m), 3.9–4.1 (2H, m), 5.3–5.5 (1H, m), 5.6–5.8 (1H, m), 6.06 (0.75H, d, J=16 Hz), 6.53 (0.25H, d, J=16 Hz), 8.03 (1H, dd, J=1, 5 Hz), 9.08 (1H, d, J=5 Hz), 9.20 (1H, br t, J=6 Hz), 9.34 (1H, d, J=1 Hz)

PREPARATION 67

N-[(2E,4E)- and (2Z,4E)-4-Ethyl-2,4-hexadien-1-yl]-3-pyridylacetamide was prepared in a similar manner to that of Preparation 59 as an oil.

IR (Neat): 3275, 1645, 1545, 1425, 1330 cm$^{-1}$

NMR (DMSO-d$_6$, δ): 0.9–1.0 (3H, m), 1.5–1.7 (3H, m), 2.1–2.2 (2H, m), 3.49 (2H, d, J=2 Hz), 3.7–3.8 (2H, m), 5.3–5.7 (2H, m), 5.99 (0.7H, d, J=16 Hz), 6.42 (0.3H, d, J=16 Hz), 7.32 (1H, dd, J=5, 8 Hz ), 7.6–7.7 (1H, m), 8.3–8.4 (1H, m), 8.44 (1H, dd, J=2, 5 Hz), 8.49 (1H, d, J=2 Hz)

PREPARATION 68

N-[(2E,4E)- and (2Z,4E)-4-Ethyl-2,4-hexadien-1-yl]-2,4-dimethylthiazole-5-carboxamide was prepared in a similar manner to that of Preparation 59 as an oil.

IR (Nujol): 3275, 1620, 1540, 1510 cm$^{-1}$

NMR (DMSO-d$_6$, δ): 0.9–1.0 (3H, m), 1.67 (3H, d, J=7 Hz), 2.1–2.3 (2H, m), 2.51 (3H, s), 2.61 (3H, s), 3.8–4.0 (2H, m) 5.3–5.8 (2H, m), 6.04 (0.8H, d, J=16 Hz), 6.49 (0.2H, d, J=16 Hz), 8.2–8.3 (1H, m)

PREPARATION 69

N-[(2E, 4E)- and (2Z, 4E)-4-Ethyl-2,4-hexadien-1-yl]-3,5-dimethylisoxazole-4-carboxamide was prepared in a similar manner to that of Preparation 54.

IR (Nujol): 3300, 1635, 1600, 1525 cm$^{-1}$

NMR (DMSO-d$_6$, δ): 0.9–1.0 (3H, m), 1.68 (3H, d, J=7 Hz), 2.1–2.3 (2H, m), 2.28 (3H, s), 2.49 (3H, s), 3.9–4.0 (2H, m), 5.4–5.8 (2H, m), 6.06 (0.8H, d, J=16 Hz), 6.50 (0.2H, d, J=16 Hz), 8.16 (1H, br t, J=6 Hz)

PREPARATION 70

N-[(2E, 4E)- and (2Z, 4E)-4-Ethyl-2,4-hexadien-1-yl]-5-methyl-4-imidazolecarboxamide was prepared in a similar manner to that of Preparation 54 as an oil.

IR (Neat): 3100, 1620, 1590, 1515, 1425, 1300 cm$^{-1}$

NMR (DMSO-d$_6$, δ): 0.9–1.0 (3H, m), 1.67 (3H, d, J=7 Hz), 2.1–2.2 (2H, m), 2.43 (3H, s), 3.8–3.9 (2H, m), 5.3–5.8 (2H, m), 6.01 (0.6H, d, J=16 Hz), 6.47 (0.4H, d, J=16 Hz), 7.54 (1H, s), 7.8–8.0 (1H, m), 12.23 (1H, br s)

PREPARATION 71

To a solution of (E,E)-4-ethyl-2,4-hexadien-1-ol (1.15 g), triphenylphosphine (3.59 g) and 5-mercaptotetrazole-1-acetamide (1.45 g) in tetrahydrofuran (15 ml) at 0° C. was added a solution of diethyl azodicarboxylate (2.40 g) in tetrahydrofuran (10 ml). The mixture was stirred at room temperature for 1 day. The reaction mixture was diluted with brine and extracted twice with ethyl acetate. The organic phase was dried over anhydrous magnesium sulfate and evaporated in vacuo. The residue was chromatographed on silica gel (6% methanol-chloroform) to give 5-[(2E,4E)- and (2Z,4E)-4-ethyl-2,4-hexadien-1-yl]thiotetrazole-1-acetamide (1.72 g) as an oil.

NMR (DMSO-d$_6$, δ): 0.8–1.1 (3H, m), 1.5–1.7 (3H, m), 2.14 (2H, q, J=7 Hz), 3.95 (2H, d, J=7 Hz), 5.04 (2H, s), 5.4–5.7 (2H, m), 6.13 (0.8H, d, J=15 Hz), 6.58 (0.2H, d, J=15 Hz), 7.53 (1H, s), 7.86 (1H, s)

PREPARATION 72

A mixture of 6-aminopyridine-3-carboxylic acid (4.24 g), N-hydroxybenzotriazole (5.13 g), 1-ethyl-3-(3-dimethylaminopropyl)carbodiimide hydrochloride (6.44 g) in N,N-dimethylformamide (100 ml) was stirred at 0° C. for 10 minutes. A solution of 4-ethyl-2,4-hexadien-1-ylamine (4.24 g) in N,N-dimethylformamide (50 ml) was added dropwise to the mixture over a period of 10 minutes and 4-dimethylaminopyridine (4.0 g) was added to the mixture. The mixture was stirred at 0° C. for 2 hours and then at room temperature overnight. The reaction mixture was diluted with aqueous sodium hydrogen carbonate solution and extracted three times with ethyl acetate. The extract was washed with aqueous sodium hydrogen carbonate solution and brine, dried over anhydrous magnesium sulfate, and evaporated in vacuo. The residue was chromatographed on silica gel (4% methanol-chloroform) to give N-(4-ethyl-2,4-hexadien-1-yl)-6-amino-3-pyridinecarboxamide (5.7 g).

mp: 79°–81° C. (ethyl acetate)

IR (Nujol): 3300, 1630, 1540 cm$^{-1}$

NMR (DMSO-d$_6$, δ): 0.94 (3H, t, J=7.6 Hz), 1.67 (3H, d, J=7.0 Hz), 2.0–2.3 (2H, m), 3.8–4.0 (2H, m), 5.3–5.8 (2H, m), 5.93 (1H, d, J=15.8 Hz), 4.6–6.6 (3H, m), 7.81 (1H, dd, J=2.4 Hz, 8.7 Hz), 8.32 (1H, t, J=5.3 Hz), 8.46 (1H, d, J=2.4 Hz)

PREPARATION 73

A solution of N-(4-ethyl-2,4-hexadien-1-yl)-6-amino-3-pyridinecarboxamide (3.0 g) and methanesulfonyl chloride (1.54 g) in pyridine (25 ml) was stirred at 50° C. for 3 hours. The reaction mixture was evaporated in vacuo and the residue was dissolved in ethyl acetate. The solution was washed with 0.5N hydrochloric acid and brine, dried over anhydrous magnesium sulfate, and evaporated in vacuo. The residue was chromatographed on silica gel (3% methanol-chloroform) to give N-(4-ethyl-2,4-hexadien-1-yl)-6-methansulfonamido-3-pyridinecarboxamide.

mp: 174°–176° C.

IR (Nujol): 3340, 1665, 1635, 1530, 1115 cm$^{-1}$

NMR (DMSO-d$_6$, δ): 0.94 (3H, t, J=7.5 Hz), 1.67 (3H, d, J=7.0 Hz), 2.0–2.5 (2H, m), 3.30 (3H, s), 3.9–4.1 (2H, m), 5.3–5.8 (2H, m), 6.06 (1H, d, J=15.8 Hz), 7.03 (1H, d, J=8.7 Hz), 8.15 (1H, dd, J=1.8 Hz, 8.7 Hz), 8.7–8.8 (2H, m), 11.2 (1H, br s)

PREPARATION 74

A solution of 4-hydroxy-7-methyl-1,8-naphthyridine-3-carboxylic acid (3.06 g), 1-ethyl-3-(3-dimethylaminopropyl)carbodiimide hydrochloride (3.17 g), and N-hydroxybenzotriazole (2.53 g) in N,N-dimethylformamide (45 ml) was stirred at 0° C. for 15 minutes. (2E,4E)- and (2Z,4E)-4-Methyl-2,4-heptadien-1-ylamine (2.35 g) was added to the solution. The solution was stirred at 0° C. for 2 hours and then at room temperature overnight. The reaction mixture was diluted with water. The resulting precipitate was filtered and washed with water to give N-[(2E,4E)- and (2Z,4E)-4-methyl-2,4-heptadien-1-yl]-4-hydroxy-7-methyl-1,8-naphthyridine-3-carboxamide (3.5 g).

mp: >250° C.

NMR (DMSO-$d_6$, δ): 0.94 (3H, t, J=7.4 Hz), 1.69 (¾H, s), 1.76 (¼H, s), 2.0–2.2 (2H, m), 2.62 (3H, s), 3.9–4.1 (2H, m), 5.3–5.8 (2H, m), 6.21 (¾H, d, J=15.6 Hz), 6.65 (¼H, d, J=15.6 Hz), 7.42 (1H, d, J=8.2 Hz), 8.49 (1H, d, J=8.2 Hz), 8.64 (1H, d, J=5.4 Hz), 9.89 (1H, t, J=5.5 Hz), 13.0 (1H, br s)

PREPARATION 75

A solution of imidazole-4-carboxylic acid (1.68 g), 1-ethyl-3-(3-dimethylaminopropyl)carbodiimide hydrochloride (3.16 g), and N-hydroxybenzotriazole (2.52 g) in N,N-dimethylformamide (25 ml) was stirred at 0° C. for 15 minutes. (2E,4E)- and (2Z,4E)-4-methyl-2,4-heptadien-1-ylamine (2.69 g) was added to the solution. The solution was stirred at 0° C. for 2 hours and then at room temperature overnight. The mixture was evaporated in vacuo and the residue was dissolved in ethyl acetate. The solution was washed with aqueous sodium hydrogen carbonate solution, water, and brine, dried over anhydrous magnesium sulfate, and evaporated in vacuo. The residue was chromatographed on silica gel (4% methanol-chloroform) to give N-[(2E,4E)- and (2Z,4E)-4-methyl-2,4-heptadien-1-yl]-4-imidazolecarboxamide (2.24 g) as an oil.

IR (Neat): 3200, 1640, 1570, 1500 cm$^{-1}$

NMR (DMSO-$d_6$, δ): 0.92 (3H, t, J=7.5 Hz), 1.67 (¾H, s), 1.74 (¼H, s), 2.0–2.3 (2H, m), 3.8–4.0 (2H, m), 5.2–5.8 (2H, m), 6.12 (¾H, d, J=15.6 Hz), 6.55 (¼H, d, J=15.6 Hz), 7.61 (1H, s), 7.71 (1H, s), 8.0 (1H, br s), 12.5 (1H, br s)

PREPARATION 76

A solution of 3-pyridylacetic acid hydrochloride (2.6 g), triethylamine (1.52 g), 1-ethyl-3-(3-dimethylaminopropyl)carbodiimide hydrochloride (3.16 g) and N-hydroxybenzotriazole (2.52 g) in N,N-dimethylformamide (40 ml) was stirred at 0° C. for 15 minutes. (2E,4E)- and (2Z,4E)-4-Methyl-2,4-heptadien-1-ylamine (2.69 g) was added to the solution. The solution was stirred at 0° C. for 2 hours and then at room temperature overnight. The reaction mixture was evaporated in vacuo and the residue was diluted with ethyl acetate and washed with aqueous sodium hydrogen carbonate solution. The organic layer was washed with water and brine, dried over anhydrous magnesium sulfate, and evaporated in vacuo. The residue was chromatographed on silica gel (4% methanol-chloroform) to give N-[(2E,4E)- and (2Z,4E)-4-methyl-2,4-heptadien-1-yl]-3-pyridylacetamide (3.19 g) as an oil.

IR (Neat): 3270, 1635, 1540 cm$^{-1}$

NMR (DMSO-$d_6$, δ): 0.93 (3H, t, J=7.4 Hz), 1.65 (¾H, s), 1.72 (¼H, s), 1.9–2.2 (2H, m), 3.47 (2H, s), 3.6–3.9 (2H, m), 5.2–5.7 (2H, m), 6.07 (¾H, d, J=15.5 Hz), 6.46 (¼H, d, J=15.5 Hz), 7.32 (1H, dd, J=4.7 Hz, 5.4 Hz), 7.4–7.5 (1H, m), 8.3 (1H, br s), 8.4–8.5 (2H, m)

PREPARATION 77

A mixture of 6-aminopyridine-3-carboxylic acid (8.36 g), N-hydroxybenzotriazole (10.2 g), 1-ethyl-3-(3-dimethylaminopropyl)carbodiimide hydrochloride (12.8 g) and 4-dimethylaminopyridine (8.12 g) in N,N-dimethylformamide (300 ml) was stirred at 0° C. for 15 minutes. (2E,4E)- and (2Z,4E)-4-methyl-2,4-heptadien-1-ylamine (7.7 g) was added to the mixture. The solution was stirred at 0° C. for 2 hours and then at room temperature overnight. The mixture was evaporated in vacuo and the residue was diluted with water. The resulting precipitate was filtered and washed with water to give N-[(2E,4E)- and (2Z-4E)-4-methyl-2,4-heptadien-1-yl]-6-amino-3-pyridinecarboxamide (13.5 g).

mp: 112°–115° C.

IR (Nujol): 3420, 3300, 1635, 1620, 1495 cm$^{-1}$

NMR (DMSO-$d_6$, δ): 0.93 (3H, t, J=7.5 Hz), 1.68 ($^{33}/_{12}$H, s), 1.75 ($^{3}/_{12}$H, s), 2.0–2.2 (2H, m), 3.90 (2H, t, J=5.3 Hz), 5.3–5.7 (2H, m), 6.14 ($^{11}/_{12}$H, d, J=15.6 Hz), 6.42 (1H, d, J=8.7 Hz), 6.46 (2H, s), 6.55 ($^{1}/_{12}$H, d, J=15.6 Hz), 7.82 (1H, dd, J=2.4 Hz, 8.7 Hz), 8.31 (1H, t, J=5.3 Hz), 8.46 (1H, d, J=2.4 Hz)

PREPARATION 78

To a 28 wt % solution of sodium methoxide in methanol (226 g) at 20° C. was added dropwise diethyl phosphonoacetic acid ethyl ester (239.8 g). The solution was stirred at the same temperature for 30 minutes under a nitrogen atmosphere. A solution of (E)-2-methyl-2-pentenal (100 g) in tetrahydrofuran (200 ml) was added dropwise at 20° C. during 20 minutes and the solution was stirred for 1 hour. The reaction mixture was poured into chilled water and extracted twice with ethyl acetate. The extract was washed with brine, dried over anhydrous magnesium sulfate, and evaporated in vacuo to give methyl (E,E)-4-methyl-2,4-heptadienoate (169.2 g) as an oil. This oil was used in the next reaction without further purification.

IR (Neat): 1715, 1620, 1310 cm$^{-1}$

NMR (CDCl$_3$, δ): 1.03 (3H, t, J=7.5 Hz), 1.77 (3H, s), 2.1–2.3 (2H, m), 3.75 (3H, s), 5.78 (1H, d, J=15.7 Hz), 5.89 (1H, t, J=7.4 Hz), 7.32 (1H, d, J=15.7 Hz)

PREPARATION 79

(E,E)-4-Methyl-2,4-heptadien-1-ol was prepared in a similar manner to that of Preparation 45 as an oil.

IR (Neat): 3300, 1640, 1450, 960 cm$^{-1}$

NMR (CDCl$_3$, δ): 0.99 (3H, t, J=7.5 Hz), 1.74 (3H, s), 2.0–2.3 (2H, m), 4.19 (2H, d, J=6.2 Hz), 5.50 (1H, t, J=7.2 Hz), 5.6–5.8 (1H, m), 6.20 (1H, d, J=15.7 Hz)

PREPARATION 80

To a solution of (E,E)-4-methyl-2,4-heptadien-1-ol (106 g) in pyridine (333 g) at 0° C. was added dropwise acetic anhydride (258 g). After two hours at room temperature, the reaction mixture was evaporated in vacuo. The residue was diluted with ethyl acetate, washed with 0.5N-hydrochloric acid and brine, dried over anhydrous magnesium sulfate, and evaporated in vacuo. The residue was distilled to give (E,E)-1-acetoxy-4-methyl-2,4-heptadiene (117.65 g) as an oil.

bp: 75°–88° C./0.1–0.2 mmHg

IR (Neat): 1735, 1645, 1440, 1375, 1230 cm$^{-1}$

NMR (CDCl$_3$, δ): 0.99 (3H, t, J=7.5 Hz), 1.74 (3H, s), 2.0–2.2 (2H, m), 2.07 (3H, s), 4.51 (2H, d, J=6.7 Hz), 5.4–5.7 (2H, m), 6.30 (1H, d, J=15.5 Hz)

PREPARATION 81

N-[(2E,4E)- and (2Z,4E)-4-Methyl-2,4-heptadien-1-yl]phthalimide was prepared in a similar manner to that of Preparation 47.

mp: 64°–66° C.

IR (Nujol): 1765, 1710, 1425, 1390 cm$^{-1}$

NMR (DMSO-d$_6$, δ): 0.92 (3H, t, J=7.5 Hz), 1.64 (2⅝H, s), 1.73 (⅜H, s), 2.0–2.2 (2H, m), 4.24 (2H, d, J=5.8 Hz), 5.3–5.7 (2H, m), 6.18 (⅞H, d, J=15.7 Hz), 6.62 (⅛H, d, J=15.7 Hz), 7.8–8.0 (4H, m)

PREPARATION 82

(2E, 4E)- and (2Z, 4E)-4-Methyl-2,4-heptadienylamine was prepared in a similar manner to that of Preparation 48.

IR (Neat): 3350, 1630, 1580 cm$^{-1}$

NMR (CDCl$_3$, δ): 0.98 (3H, t, J=7.5 Hz), 1.45 (2H, s), 1.73 (1⅞H, s), 1.81 (⅛H, s), 2.0–2.3 (2H, m), 3.3–3.4 (2H, m), 5.2–5.9 (2H, m), 6.15 (⅝H, d, J=15.5 Hz), 6.54 (⅛H, d, J=15.5 Hz)

PREPARATION 83

A solution of 2,5-dimethyl-4-imidazolecarboxylic acid (1.4 g), 1-ethyl-3-(3-dimethylaminopropyl)carbodiimide hydrochloride (1.93 g), and N-hydroxybenzotriazole (1.49 g) in N,N-dimethylformamide (14 ml) was stirred at 0° C. for 15 minutes. A solution of (2E,4E)- and (2Z,4E)-4-methyl-2,4-heptadien-1-ylamine (1.79 g) in N,N-dimethylformamide (6 ml) was added dropwise to the solution over a period of 10 minutes. The mixture was stirred at 0° C. for 30 minutes and then at room temperature for 24 hours. The reaction mixture was diluted with water and extracted twice with ethyl acetate. The organic phase was washed with brine, dried over anhydrous magnesium sulfate, and evaporated in vacuo. The residue was chromatographed on silica gel (3% methanol-chloroform) to give N-[(2E,4E)- and (2Z,4E)-4-methyl-2,4-heptadien-1-yl]- 2,5-dimethyl-4-imidazolecarboxamide (1.6 g) as an oil.

IR (Neat): 3400, 3200, 1670, 1550, 1510, 1300 cm$^{-1}$

NMR (DMSO-d$_6$, δ): 0.93 (3H, t, J=7 Hz), 1.66 (3H, s), 2.0–2.2 (2H, m), 2.23 (3H, s), 2.39 (3H, s), 3.85 (2H, t, J=6 Hz), 5.3–5.7 (2H, m), 6.11 (⅔H, d, J=15 Hz), 6.53 (⅓H, d, J=15 Hz), 7.72 (1H, br t, J=6 Hz), 11.91 (1H, br s)

PREPARATION 84

N-[(2E,4E)- and (2Z,4E)-4-Methyl-2,4-heptadien-1-yl]-8-oxo-7H-pyrido[2,3-d]pyridazin-5-acetamide was prepared in a similar manner to that of Preparation 74.

mp 253°–256° C.

IR (Nujol): 3280, 1690, 1640, 1550, 1335 cm$^{-1}$

NMR (DMSO-d$_6$, δ): 0.95 (3H, t, J=7.4 Hz), 1.66 (2⅛H, s), 1.73 (⅜H, s), 2.0–2.2 (2H, m), 3.74 (2H, br s), 3.89 (2H, s), 5.3–5.6 (2H, m), 6.10 (⅞H, d, J=15.6 Hz), 6.42 (⅛H, d, J=15.6 Hz), 7.85 (1H, dd, J=3.0 Hz, 7.9 Hz), 8.18 (1H, br s), 8.59 (1H, d, J=7.9 Hz), 9.12 (1H, d, J=3.0 Hz)

PREPARATION 85

N-[(2E, 4E)- and (2Z,4E)-4-Methyl-2,4-heptadien-1-yl]-2-oxoindoline-5-carboxamide was prepared in a similar manner to that of Preparation 74.

mp: 163°–167° C.

IR (Nujol): 3280, 1730, 1670, 1630, 1530 cm$^{-1}$

NMR (DMSO-d$_6$, δ): 0.93 (3H, t, J=7.5 Hz), 1.68 (2¼H, s), 1.75 (¾H, s), 2.0–2.2 (2H, m), 2.53 (2H, s), 3.9–4.0 (2H, m), 5.2–5.8 (2H, m), 6.15 (¾H, 1H, d, J=15.6 Hz), 6.57 (¼H, d, J=15.6 Hz), 6.85 (1H, d, J=8.6 Hz), 7.75 (1H, s), 7.76 (1H, d, J=8.6 Hz), 8.48 (1H, t, J=5.4 Hz), 10.62 (1H, s)

PREPARATION 86

N-[(2E,4E)- and (2Z,4E)-4-Methyl-2,4-heptadien-1-yl]-6-oxo-1,4,5,6-tetrahydropyridazine-3-carboxamide was prepared in a similar manner to that of Preparation 74.

mp: 104°–106° C.

IR (Nujol): 3400, 3100, 1680, 1660, 1625, 1510 cm$^{-1}$

NMR (DMSO-d$_6$, δ): 0.90 (3H, t, J=7.5 Hz), 1.66 (¾H, s), 1.72 (¾H, s), 1.9–2.2 (2H, m), 2.38 (2H, t, J=8.8 Hz), 2.73 (2H, t, J=8.8 Hz), 3.7–3.9 (2H, m), 5.2–5.7 (2H, m), 6.09 (¾H, d, J=15.6 Hz), 6.52 (¼H, d, J=15.6 Hz), 8.2–8.4 (1H, m), 11.09 (1H, s)

PREPARATION 87

N-[(2E,4E)- and (2Z,4E)-4-Methyl-2,4-heptadien-1-yl]-1H-1,2,4-triazole-3-carboxamide was prepared in a similar manner to that of Preparation 74.

mp: 150°–152° C.

IR (Nujol): 3300, 1645, 1565 cm$^{-1}$

NMR (DMSO-d$_6$, δ): 0.93 (3H, t, J=7.5 Hz), 1.67 (¾H, s), 1.83 (¾H, s), 2.0–2.2 (2H, m), 3.93 (2H, br s), 5.2–5.8 (2H, m), 6.15 (¾H, d, J=15.6 Hz), 6.57 (¼H, d, J=15.6 Hz), 8.5 (1H, br s), 8.8 (1H, br s), 14.7 (1H, br s)

PREPARATION 88

N-(4-Methyl-2,4-heptadien-1-yl) -2-Amino-4-methyl-5-pyrimidinecarboxamide was prepared in a similar manner to that of Preparation 72.

mp: 159°–160° C. (N,N-dimethylformamide-water)

IR (Nujol): 3280, 1680, 1630, 1600, 1540 cm$^{-1}$

NMR (DMSO-d$_6$, δ): 0.94 (3H, t, J=7.4 Hz), 1.68 (3H, s), 2.0–2.2 (2H, m), 2.37 (3H, s), 3.8–3.9 (2H, m), 5.4–5.7 (2H, m), 6.16 (1H, d, J=15.8 Hz), 6.90 (2H, s), 8.2–8.4 (2H, m)

PREPARATION 89

N-[(2E,4E)- and (2Z,4E)-4-Ethyl-2,4-hexadien-1-yl]-2-methoxy-3-pyridinecarboxamide was prepared in a similar manner to that of Preparation 75.

IR (Neat): 3400, 1650, 1585, 1520, 1420 cm$^{-1}$

NMR (CDCl$_3$, δ): 0.9–1.1 (3H, m), 1.6–1.8 (3H, m), 2.1–2.3 (2H, m), 4.09 (3H, s), 4.1–4.3 (2H, m), 5.4–5.9 (2H, m), 6.15 (⅘H, d, J=15.8 Hz), 6.60 (⅕H, d, J=15.8 Hz), 7.0–7.1 (1H, m), 8.0 (1H, br s), 8.26 (1H, dd, J=2.0 Hz, 4.9 Hz), 8.5–8.6 (1H, m)

PREPARATION 90

N-[(2E,4 E)- and (2Z, 4E) -4-Methyl-2,4-heptadien-1-yl]-3-amino-4-pyrazolecarboxamide was prepared in a similar manner to that of Preparation 75.

mp: 137°–140° C. (ethyl acetate)

IR (Nujol): 3200, 1625, 1560, 1530 cm$^{-1}$

NMR (DMSO-d$_6$, δ): 0.93 (3H, t, J=7.4 Hz), 1.68 (¼H, s), 1.74 (¾H, s), 2.0–2.3 (2H, m), 3.8–3.9 (2H, m), 5.2–5.8 (2H, m), 5.7 (2H, br s), 6.13 (¾H, d, J=15.6 Hz), 6.58 (¼H, d, J=15.6 Hz), 7.6–8.0 (3H, m)

PREPARATION 91

N-[(2E, 4E)- and (2Z,4E)-4-Methyl-2,4-heptadien-1-yl]-2-fluoro-3-pyridinecarboxamide was prepared in a similar manner to that of Preparation 75.

IR (Neat) : 3260, 1650, 1600, 1520, 1425 cm$^{-1}$

NMR (DMSO-d$_6$, δ): 0.94 (3H, t, J=7.5 Hz), 1.76 (12/5H, s), 1.81 (3/5H, s), 2.0–2.2 (2H, m), 3.9–4.1 (2H, m), 5.3–5.8 (2H, m), 6.20 (4/5H, d, J=15.7 Hz), 6.62 (1/5H, d, J=15.7 Hz), 7.4–7.5 (1H, m), 8.1–8.2 (1H, m), 8.3–8.4 (1H, m), 8.67 (1H, br s)

PREPARATION 92

N-[(2E, 4E)- and (2Z,4E)-4-Methyl-2,4-heptadien-1-yl]-3-methyl-5-pyrazolecarboxamide was prepared in a similar manner to that of Preparation 75.

IR (Neat) : 3200, 1640, 1550 cm$^{-1}$

NMR (DMSO-d$_6$, δ): 0.9–1.0 (3H, m), 1.66 (¾H, s), 1.74 (¾H, s), 2.0–2.3 (2H, m), 3.8–3.9 (2H, m), 5.3–5.7 (2H, m), 6.11 (¾H, d, J=15.6 Hz), 6.37 (1H, br s), 6.54 (¼H, d, J=15.6 Hz), 8.14 (1H, br s), 12.88 (1H, s)

PREPARATION 93

N-[(2E,4E)- and (2Z,4E)-4-Methyl-2,4-heptadien-1-yl]-3-amino-2-pyrazinecarboxamide was prepared in a similar manner to that of Preparation 75.

IR (Neat): 3400, 3300, 1650, 1600, 1510, 1430 cm$^{-1}$

NMR (CDCl$_3$, δ): 0.98 (3H, t, J=7.6 Hz), 1.73 (¾H, s), 1.80 (¾H, s), 2.0–2.3 (2H, m), 4.0–4.2 (2H, m), 5.3–5.8 (2H, m), 6.26 (¾H, d, J=15.7 Hz), 6.66 (¼H, d, J=15.7 Hz), 7.78 (1H, d, J=2.4 Hz), 7.9 (1H, br s), 8.17 (1H, d, J=2.4 Hz)

PREPARATION 94

N-[(2E,4E)- and (2Z,4E)-4-Methyl-2,4-heptadien-1-yl]-2-ethyl-4-imidazolecarboxamide was prepared in a similar manner to that of Preparation 75.

IR (Neat): 3200, 1640, 1630, 1580, 1530 cm$^{-1}$

NMR (DMSO-d$_6$, δ): 0.92 (3H, t, J=7.4 Hz), 1.21 (3H, t, J=7.6 Hz), 1.66 (¾H, s), 1.74 (¾H, s), 2.0–2.2 (2H, m), 2.63 (2H, q, J=7.6 Hz), 3.8–3.9 (2H, m), 5.3–5.7 (2H, m), 6.10 (¾H, d, J=15.6 Hz), 6.54 (¼H, d, J=15.6 Hz), 7.47 (1H, d, J=1.9 Hz), 7.8–7.9 (1H, m), 12.1 (1H, br s)

PREPARATION 95

N-[(2E,4E)- and N-(2Z,4E)-4-Ethyl-2,4-heptadien-1-yl]-5-methyl-4-imidazolecarboxamide was prepared in a similar manner to that of Preparation 54 as an oil.

IR (Neat) : 3400, 3150, 1650, 1590 cm$^{-1}$

NMR (DMSO-d$_6$, δ): 0.93 (3H, t, J=7.5 Hz), 1.66 (¾H, s), 1.74 (¾H, s), 2.0–2.2 (2H, m), 2.43 (3H, s), 3.8–4.0 (2H, m), 5.2–5.7 (2H, m), 6.11 (¾H, d, J=15.6 Hz), 6.53 (¼H, d, J=15.6 Hz), 7.53 (1H, s), 7.8–7.9 (1H, m), 12.2 (1H, br s)

PREPARATION 96

To a 28 wt % solution of sodium methoxide in methanol (112.6 g) at 10° C. were added dropwise diethyl phosphonoacetic acid ethyl ester (110.75 g) and (E)-2-methyl-2-hexenal (50.36 g) successively under a nitrogen atmosphere. The reaction mixture was stirred at room temperature for 4 hours, poured into chilled water and extracted with dichloromethane. The extract was washed with brine, dried over anhydrous magnesium sulfate, and evaporated to give 74.88 g of crude methyl (E,E)-4-methyl-2,4-octadienoate as an oil. This oil was used in the next reaction without further purification.

IR (Neat): 3450, 2900, 1720, 1620, 1430, 1300 cm$^{-1}$

NMR (CDCl$_3$, δ): 0.93 (3H, t, J=7 Hz), 1.4–1.5 (2H, m), 1.77 (3H, s), 1.91 (2H, q, J=7 Hz), 3.75 (3H, s), 5.79 (1H, d, J=16 Hz), 5.91 (1H, t, J=7 Hz), 7.33 (1H, d, J=16 Hz)

PREPARATION 97

(E,E)-4-Methyl-2,4-octadien-1-ol was prepared in a similar manner to that of Preparation 45.

PREPARATION 98

(E,E)-1-Acetoxy-4-methyl-2,4-octadiene was prepared in a similar manner to that of Preparation 80.

IR (Neat) : 3450, 1740, 1645 cm$^{-1}$

NMR (CDCl$_3$, δ): 0.91 (3H, t, J=7 Hz), 1.3–1.4 (2H, m), 1.74 (3H, s), 2.06 (3H, s), 2.1–2.2 (2H, m), 4.61 (2H, d, J=7 Hz), 5.5–5.7 (2H, m), 6.31 (1H, d, J=15 Hz)

PREPARATION 99

N-[(2E,4E)- and (2Z, 4E)-4-Methyl-2,4-octadien-1-yl]-phthalimide was prepared in a similar manner to that of Preparation 47.

IR (Nujol) : 3450, 1720, 1320 cm$^{-1}$

NMR (CDCl$_3$ , δ): 0.89 (3H, t, J=7 Hz), 1.3–1.5 (2H, m), 1.67 (2H, s), 1.76 (1H, s), 2.0–2.2 (2H, m), 4.35 (2H, t, J=7 Hz), 5.3–5.8 (2H, m), 6.32 (⅔H, d, J=15 Hz), 6.73 (⅓H, d, J=15 Hz), 7.7–7.9 (4H, m)

PREPARATION 100

(2E,4E)- and (2Z,4E)-4-Methyl-2,4-octadienylamine was prepared in a similar manner to that of Preparation 48.

IR (Neat) : 3350, 1600 cm$^{-1}$

NMR (CDCl$_3$, δ): 0.91 (3H, t, J=7 Hz), 1.2–1.5 (4H, m), 1.74 (3H, s), 2.10 (2H, q, J=7 Hz), 3.35 (2H, d, J=6 Hz), 5.45 (1H, t, J=7 Hz), 5.6–5.7 (1H, m), 6.16 (1H, d, J=16 Hz)

PREPARATION 101

N-(4-Methyl-2,4-octadien-1-yl)-3-pyridinecarboxamide was prepared in a similar manner to that of Preparation 50.

IR (Neat): 3300, 1640, 1590, 1540, 1410, 1300 cm$^{-1}$

NMR (DMSO-d$_6$, δ): 0.87 (3H, t, J=7 Hz), 1.3–1.4 (2H, m), 1.70 (3H, s), 2.08 (2H, q, J=7 Hz), 4.00 (2H, t, J=6 Hz), 5.47 (1H, t, J=7 Hz), 5.5–5.7 (1H, m), 6.22 (1H, d, J=16 Hz), 7.4–7.5 (1H, m), 8.2–8.3 (1H, m), 8.71 (1H, dd, J=2 Hz, 5 Hz), 8.87 (1H, br t, J=7 Hz), 9.06 (1H, dd, J=1 Hz, 2 Hz)

PREPARATION 102

N-[(2E,4E)- and (2Z,4E)-4-Methyl-2,4-octadien-1-yl]-3-pyridylacetamide was prepared in a similar manner to that of Preparation 59.

IR (Neat): 3250, 1645, 1540, 1425, 1325 cm$^{-1}$

NMR (DMSO-d$_6$, δ): 0.8–1.0 (3H, m), 1.2–1.4 (2H, m), 1.66 (2H, s), 1.74 (1H, s), 2.0–2.1 (2H, m), 3.47 (2H, s), 3.7–3.8 (2H, m), 5.2–5.7 (2H, m), 6.09 (⅔H, d, J=16 Hz), 6.48 (⅓H, d, J=16 Hz), 7.32 (1H, dd, J=5 Hz, 8 Hz), 7.6–7.7 (1H, m), 8.31 (1H, br t, J=5 Hz), 8.4–8.5 (2H, m)

EXAMPLE 1

To a mixture of 4-ethyl-2,4-hexadien-1-yl 3-pyridinecarboxylate (2.84 g), sodium nitrite (5.08 g), water (30 ml), and methanol (80 ml) at 15° C. was added dropwise 6N hydrochloric acid (9.8 ml) during 15 minutes. After being stirred for 1 hour 20 minutes, the reaction mixture was diluted with water and extracted with dichloromethane. The organic layer was washed with water and brine, dried over anhydrous magnesiumsulfate, and evaporated in vacuo. The residue was chromatographed on silica gel (1.5% methanol in chloroform). The first eluted fraction contains one isomer (i.e. isomer A) of 4-ethyl-2-hydroxyimino-5-nitro-3-hexen-1-yl 3-pyridinecarboxylate (0.17 g) as an oil.

IR (Neat): 3170, 1730, 1650, 1550 cm$^{-1}$

NMR (CDCl$_3$, δ): 1.07 (3H, t, J=7 Hz), 1.60 (3H, d, J=7 Hz), 2.43 (2H, m), 5.10 (1H, q, J=7 Hz), 5.31 (2H, s), 6.12 (1H, s), 7.46 (1H, dd, J=5, 8 Hz), 8.33 (1H, br d, J=8 Hz), 8.81 (1H, dd, J=2, 5 Hz), 9.25 (1H, br s)

The second eluted fraction contains the other isomer (i.e. isomer B) of 4-ethyl-2-hydroxyimino-5-nitro-3-hexen- 1-yl 3-pyridinecarboxylate (1.77 g) as an oil.

IR (Neat): 3180, 1725, 1595, 1550 cm$^{-1}$

NMR (CDCl$_3$, δ): 1.06 (3H, t, J=8 Hz), 1.73 (3H, d, J=7 Hz), 2.24 (2H, q, J=8 Hz), 5.05 (2H, s), 5.16 (1H, q, J=7 Hz), 6.13 (1H, s), 7.44 (1H, dd, J=5, 8 Hz), 8.32 (1H, br d, J=8 Hz), 8.78 (1H, dd, J=2, 5 Hz), 9.20 (1H, br s)

EXAMPLE 2

4-Ethyl-2-hydroxyimino-5-nitro-3-hexen-1-yl carbamate was prepared in a similar manner to that of Example 1.

Isomer A: Oil

IR (Neat): 3300, 1720, 1600, 1550 cm$^{-1}$

NMR (CDCl$_3$, δ): 1.05 (3H, t, J=8 Hz), 1.69 (3H, d, J=7 Hz), 2.42 (2H, m), 4.97 (2H, br s), 5.01 (2H, s), 5.13 (1H, q, J=7 Hz), 6.04 (1H, s)

Isomer B:

mp: 69°–72° C. (ethyl acetate-hexane)

IR (Neat): 3300, 1720, 1600, 1550 cm$^{-1}$

NMR (DMSO-d$_6$, δ): 0.97 (3H, t, J=8 Hz), 1.58 (3H, d, J=7 Hz), 2.12 (2H, q, J=8 Hz), 4.58 (2H, s), 5.40 (1H, q, J=7 Hz), 6.07 (1H, s), 6.58 (2H, br s), 11.31 (1H, s)

EXAMPLE 3

4-Ethyl-2-hydroxyimino-5-nitro-3-hexen-1-yl ethylcarbamate was prepared in a similar manner to that of Example 1.

Isomer A: Oil

IR (Neat): 3350, 1710, 1550 cm$^{-1}$

NMR (CDCl$_3$, δ): 1.05 (3H, t, J=8 Hz), 1.15 (3H, t, J=7Hz), 1.68 (3H, d, J=7 Hz), 2.40 (2H, m), 3.22 (2H, m), 4.78 (1H, m), 5.00 (2H, s), 5.12 (1H, q, J=7 Hz), 6.02 (1H ,s)

Isomer B: Oil

IR (Neat) : 3300, 1710, 1550 cm$^{-1}$

NMR (CDCl$_3$, δ): 1.06 (3H, t, J=8 Hz), 1.13 (3H, t, J=7 Hz), 1.72 (3H, d, J=7 Hz), 2.20 (2H, q, J=8 Hz), 3.22 (2H, m), 4.74 (2H, s), 4.86 (1H, m), 5.17 (1H, q, J=7 Hz), 6.05 (1H, s)

EXAMPLE 4

N-(4-Ethyl-2-hydroxyimino-5-nitro-3-hexen-1-yl)phthalimide was prepared in a similar manner to that of Example 1.

Isomer A: Oil

IR (Neat): 3400, 1770, 1710, 1610, 1550 cm$^{-1}$

NMR (CDCl$_3$, δ): 1.00 (3H, t, J=8 Hz), 1.50 (3H, d, J=7 Hz), 2.30 (2H, m), 4.74 (2H, s), 4.95 (1H, q, J=7 Hz), 5.86 (1H, s), 7.75 (2H, m), 7.88 (2H, m)

Isomer B: Oil

IR (Neat): 3400, 1770, 1730, 1710, 1690, 1610, 1550 cm$^{-1}$

NMR (CDCl$_3$, δ): 1.01 (3H, t, J=8 Hz), 1.67 (3H, d, J=7 Hz), 2.20 (2H, m), 4.48 (2H, s), 5.10 (1H, q, J=7 Hz), 5.95 (1H, s), 7.73 (2H, m), 7.85 (2H, m)

EXAMPLE 5

1-Acetylamino-4-ethyl-2-hydroxyimino-5-nitro-3-hexene was prepared in a similar manner to that of Example 1.

Isomer A:

mp 124°–125° C. (dichloromethane)

IR (Nujol): 3350, 1625, 1545 cm$^{-1}$

NMR (CDCl$_3$, δ): 1.04 (3H, t, J=8 Hz), 1.68 (3H, d, J=7 Hz), 2.02 (3H, s), 2.39 (2H, m), 4.23 (2H, d, J=6 Hz), 5.11 (1H, q, J=7 Hz), 6.00 (1H, br s), 6.04 (1H, s)

Isomer B: Oil

IR (Neat) : 3250, 1640, 1545 cm$^{-1}$

NMR (CDCl$_3$, δ): 1.05 (3H, t, J=8 Hz), 1.73 (3H, d, J=7 Hz), 2.02 (3H, s), 2.17 (2H, 2, q, J=8 Hz), 4.09 (2H, d, J=6 Hz), 5.16 (1H, q, J=7 Hz), 6.05 (1H, s), 6.37 (1H, m)

EXAMPLE 6

To a mixture of crude N-(4-ethyl-2,4-hexadien-1-yl)-3-pyridinecarboxamide (2.14 g), sodium nitrite (3.85 g), water (30 ml), and methanol (60 ml) at 15° C. was added dropwise 6N hydrochloric acid (7.4 ml) during 20 minutes. After 50 minutes, the reaction mixture was diluted with water and extracted three times with dichloromethane. The extracts combined were cooled at 0° C. to give a precipitate which was designated as isomer A. After evaporation of the filtrate, the residue was dissolved in 10 ml of dichloromethane and allowed to stand at −10° C. overnight to give a precipitate which was designated as isomer B. Isomer A with high Rf value on thin layer chromatography (10% methanol-chloroform) and isomer B with low Rf value are configurational isomers at the hydroxyimino group of the desired N-(4-ethyl-3-hydroxyimino-5-nitro-3-hexane-yl)-3-pyridinecarboxamide. Recrystallization of isomer A from methanol-dichloromethane-hexane gave N-(4-ethyl-3-hydroxyimino-5-nitro-3-hexen-1-yl)-3-pyridinecarboxamide (304 mg).

mp: 155°–158° C.

IR (Nujol): 3280, 1640, 1600, 1550 cm$^{-1}$

NMR (DMSO-d$_6$, δ): 0.98 (3H, t, J=7 Hz), 1.46 (3H, d, J=7 Hz), 2.29 (2H, m), 4.25 (2H, d, J=6 Hz), 5.30 (1H, q, J=7 Hz), 6.01 (1H, s), 7.52 (1H, dd, J=5, 8 Hz), 8.16 (1H, br d, J=8 Hz), 8.71 (1H, dd, J=2, 5 Hz), 8.98 (2H, br s), 11.41 (1H, s)

Recrystallization of isomer B from aqueous methanol gave N-(4-ethyl-3-hydroxyimino-5-nitro-3-hexen-1-yl)-3-pyridinecarboxamide (366 mg).

mp: 138°–140° C.

IR (Nujol): 3360, 1640, 1595, 1550 cm$^{-1}$

NMR (DMSO-d$_6$, δ): 0.94 (3H, t, j=7 Hz), 1.55 (3H, d, J=7 Hz), 2.09 (2H, m), 4.13 (2H, d, J=6 Hz), 5.36 (1H, q, J=7 Hz), 6.00 (1H, s), 7.52 (1H, dd, J=5, 8 Hz), 8.16 (1H, br d, J=8 Hz), 8.70 (1H, dd, J=2, 5 Hz), 8.90–8.99 (2H, m), 11.01 (1H, s)

EXAMPLE 7

N,N-Dimethyl-N'-(4-ethyl-2-hydroxyimino-5-nitro-3-hexen-1-yl)sulfamide was prepared in a similar manner to that of Example 1.

Isomer A: Oil

IR (Neat) : 3300, 1630, 1550 cm$^{-1}$

NMR (CDCl$_3$, δ): 1.05 (3H, t, J=8 Hz), 1.70 (3H, d, J=7 Hz), 2.36 (2H, m), 2.76 (6H, s), 3.95 (2H, d, J=6 Hz), 5.16 (1H, q, J=7 Hz), 5.25 (1H, br s), 6.08 (1H, s)

Isomer B: Oil

IR (Neat) : 3300, 1630, 1550 cm$^{-1}$

NMR (CDCl$_3$, δ): 1.07 (3H, t, J=8 Hz), 1.73 (3H, d, J=7 Hz), 2.21 (2H, q, J=8 Hz), 2.80 (6H, s), 3.88 (2H, d, J=6 Hz), 5.17 (1H, q, J=7 Hz), 5.36 (1H, br s), 6.06 (1H, s)

EXAMPLE 8

N-Cyano-N'-(4-ethyl-2-hydroxyimino-5-nitro-3-hexen-1-yl)-3-pyridinecarboximidamide was prepared in a similar manner to that of Example 1.

Isomer A: Oil

IR (Neat): 3200, 2180, 1730, 1580, 1545 cm$^{-1}$

NMR (DMSO-d$_6$, δ): 1.01 (3H, t, J=8 Hz), 1.57 (3H, d, J=7 Hz), 2.33 (2H, m), 4.33 (2H, d, J=6 Hz), 5.45 (1H, q, J=7 Hz), 6.02 (1H, s), 7.64 (1H, m), 8.03 (1H, m), 8.78 (2H, m), 9.62 (1H, br t, J=6 Hz), 11.56 (1H, s)

Isomer B: Oil

IR (Neat): 3230, 2180, 1585, 1550 cm$^{-1}$

NMR (DMSO-d$_6$, δ): 0.96 (3H, t, J=8 Hz), 1.60 (3H, d, J=7 Hz), 2.12 (2H, m), 4.22 (2H, d, J=6 Hz), 5.43 (1H, q, J=7 Hz), 6.03 (1H, s), 7.62 (1H, m), 7.98 (1H, m), 8.77 (2H, m), 9.60 (1H, br t, J=6 Hz), 11.19 (1H, s)

EXAMPLE 9

6-(4-Ethyl-2-hydroxyimino-5-nitro-3-hexen-1-yl)-thiopurine was prepared in a similar manner to that of Example 1.

mp: 162°–165° C.

IR (Nujol): 1595, 1580, 1550, 1370 cm$^{-1}$

NMR (DMSO-d$_6$, δ): 0.94 (3H, t, J=8 Hz), 1.48 (3H, d, J=7 Hz), 2.0–2.5 (2H, m), 4.32 (2H, s), 5.30 (1H, q, J=7 Hz), 6.20 (1H, s), 8.47 (1H, s), 8.72 (1H, s), 11.72 (1H, s)

EXAMPLE 10

1-Phenyl-5-(4-ethyl-2-hydroxyimino-5-nitro-3-hexen-1-yl)thiotetrazole was prepared in a similar manner to that of Example 1.

Isomer A: Oil

IR (Neat): 3200, 2950, 1595, 1550, 1500, 1355 cm$^{-1}$

NMR (CDCl$_3$, δ): 0.99 (3H, t, J=8 Hz), 1.69 (3H, d, J=7 Hz), 2.1–2.5 (2H, m), 4.35 (2H, s), 5.10 (1H, q, J=7 Hz), 6.21 (1H, s), 7.56 (5H, s)

Isomer B:

mp: 66°–69° C.

IR (Nujol): 3300, 1590, 1550, 1495, 1380 cm$^{-1}$

NMR (DMSO-d$_6$): 0.92 (3H, t, J=8 Hz), 1.54 (3H, d, J=7 Hz), 2.07 (2H, q, J=8 Hz), 4.30 (2H, s), 5.37 (1H, q, J=7 Hz), 6.04 (1H, s), 7.16 (5H, s), 11.38 (1H, s)

EXAMPLE 11

1-Methyl-2-(4-ethyl-2-hydroxyimino-5-nitro-3-hexen-1-yl)thioimidazole was prepared in a similar manner to that of Example 1.

mp: 91°–93° C.

IR (Nujol): 3080, 1545, 1405, 1375, 1350 cm$^{-1}$

NMR (DMSO-d$_6$, δ): 0.95 (3H, t, J=7 Hz), 1.52 (3H, d, J=7 Hz), 2.1–2.5 (2H, m), 3.56 (3H, s), 3.85 (2H, s), 5.29 (1H, q, J=7 Hz), 5.91 (1H, s), 6.74 (1H, d, J=1 Hz), 7.23 (1H, d, J=1 Hz), 11.57 (1H, s)

EXAMPLE 12

1-Methyl-5-(4-ethyl-2-hydroxyimino-5-nitro-3-hexen-1-yl)thiotetrazole was prepared in a similar manner to that of Example 1.

Isomer A:

mp: 83°–84° C.

IR (Nujol): 3450, 1555, 1375 cm$^{-1}$

NMR (DMSO-d$_6$): 0.94 (3H, t, J=7 Hz), 1.5.5 (3H, d, J=7 Hz), 2.1–2.4 (2H, m), 3.93 (3H, s), 4.14 (2H, s), 5.33 (1H, q, J=7 Hz), 6.09 (1H, s), 11.78 (1H, s)

Isomer B:

mp: 83°–84° C.

IR (Nujol): 3250, 1550, 1370 cm$^{-1}$

NMR (DMSO-d$_6$, δ): 0.95 (3H, t, J=8 Hz), 1.57 (3H, d, J=7 Hz), 2.11 (2H, q, J=8 Hz), 3.94 (3H, s), 4.20 (2H, s), 5.39 (1H, q, J=7 Hz), 6.06 (1H, s), 11.35 (1H, s)

EXAMPLE 13

5-Methyl-2-(4-ethyl-2-hydroxyimino-5-nitro-3-hexen-1-yl)thio-1,3,4-thiadiazole was prepared in a similar manner to that of Example 1.

Isomer A:

mp: 75°–76° C.

IR (Nujol) : 3150, 1550, 1375 cm$^{-1}$

NMR (CDCl$_3$, δ): 1.00 (3H, t, J=8 Hz), 1.62 (3H, d, J=7 Hz), 2.1–2.6 (2H, m), 2.74 (3H, s), 4.29 (2H, s), 5.0–5.2 (1H, m), 6.15 (1H, s)

Isomer B:

mp: 108°–109° C.

IR (Nujol): 3230, 1545, 1385, 1375 cm$^{-1}$

NMR (CDCl$_3$, δ): 0.9–1.1 (3H, m), 1.6–1.7 (3H, m), 2.1–2.6 (2H, m), 2.74 (3H, s), 4.36 (2H, s), 5.0–5.2 (1H, m), 6.14 (1H, s)

EXAMPLE 14

2-(4-Ethyl-2-hydroxyimino-5-nitro-3-hexen-1-yl)thiobenzothiazole was prepared in a similar manner to that of Example 1.

Isomer A: Oil

IR (Neat): 3200, 1650, 1550, 1425, 1380, 1350, 1000 cm$^{-1}$

NMR (CDCl$_3$, δ): 0.9–1.1 (3H, m), 1.5–1.7 (3H, m), 2.1–2.6 (2H, m), 4.35 (2H, s), 5.0–5.2 (1H, m), 6.25 (1H, s), 7.3–7.5 (2H, m), 7.76 (1H, d, J=8 Hz), 7.89 (1H, d, J=8 Hz)

Isomer B:

mp: 102°–103° C.

IR (Nujol): 1540, 1415, 1375, 1005 cm$^{-1}$

NMR (DMSO-d$_6$, δ): 0.96 (3H, t, J=7 Hz), 1.52 (3H, d, J=7 Hz), 2.12 (2H, q, J=7 Hz), 4.32 (2H, s), 5.39 (1H, q, J=7 Hz), 6.08 (1H, s), 7.3–7.6 (2H, m), 7.85 (1H, d, J=7 Hz), 8.02 (1H, d, J=7 Hz), 11.34 (1H, s)

EXAMPLE 15

2-(4-Ethyl-2-hydroxyimino-5-nitro-3-hexen-1-yl)thiopyrimidine was prepared in a similar manner to that of Example 1.

Oil

IR (Neat): 3150, 1550, 1380 cm$^{-1}$

NMR (CDCl$_3$, δ): 0.9–1.2 (3H, m), 1.5–1.7 (3H, m), 2.0–2.6 (2H, m), 4.18 (2H, s), 4.9–5.2 (1H, m), 6.18 (1H, s), 7.01 (1H, t, J=5 Hz), 8.55 (2H, d, J=5 Hz)

EXAMPLE 16

N-(4-Ethyl-2-hydroxyimino-6-methyl-5-nitro-3-hepten 1-yl)-3-pyridinecarboxamide was prepared in a similar manner to that of Example 1.

Isomer A:

mp: 157°–158° C.

IR (Nujol): 3250, 1645, 1560, 1540, 1375 cm$^{-1}$

NMR (DMSO-d$_6$, δ): 0.66 (3H, d, J=7 Hz), 0.84 (3H, d, J=7 Hz), 0.98 (3H, t, J=7Hz), 2.1–2.4 (3H, m), 4.1–4.5 (2H, m), 4.80 (1H, d, J=11 Hz), 6.17 (1H, s), 7.52 (1H, dd, J=5 Hz, 8 Hz), 8.1–8.2 (1H, m), 8.71 (1H, dd, J=2 Hz, 5 Hz), 8.90–9.10 (2H, m)

Isomer B:

mp: 141°–142° C.

IR (Nujol): 3380, 1645, 1555, 1373 cm$^{-1}$

NMR (DMSO-d$_6$, δ): 0.80 (3H, d, J=7 Hz), 0.9–1.1 (6H, m), 2.13 (2H, q, J=8 Hz), 2.3–2.5 (1H, m), 4.0–4.3 (2H, m), 4.86 (1H, d, J=11 Hz), 6.14 (1H, s), 7.4–7.6 (1H, m), 8.1–8.21 (1H, m), 8.69 (1H, dd, J=2 Hz, 5 Hz), 8.94 (1H, t, J=6 Hz), 8.98 (1H, d, J=1 Hz)

EXAMPLE 17

1-Acetylamino-4-ethyl-2-hydroxyimino-6-methyl-5-nitro-3-heptene was prepared in a similar manner to that of Example 1.

Isomer A: Oil

IR (Neat): 3250, 1650, 1550, 1365 cm$^{-1}$

NMR (DMSO-d$_6$, δ): 0.7–1.1 (9H, m), 1.81 (3H, s), 2.20–2.40 (3H, m), 3.9–4.1 (2H, m), 4.83 (1H, d, J=11 Hz), 6.09 (1H, s), 8.12 (1H, t, J=6 Hz), 11.30 (1H, s)

Isomer B: Oil

IR (Neat): 3250, 1650, 1545, 1370 cm$^{-1}$

NMR (DMSO-d$_6$, δ): 0.8–1.0 (9H, m), 1.77 (3H, s), 2.09 (2H, q, J=8 Hz), 2.30–2.50 (1H, m), 3.8–4.0 (2H, m), 4.86 (1H, d, J=11 Hz), 6.09 (1H, s), 8.07 (1H, t, J=6 Hz), 10.94 (1H, s)

EXAMPLE 18

To a mixture of crude N-(4-methyl-2,4-heptadien-1-yl)-3-pyridinecarboxamide (2.2 g), sodium nitrite (3.95 g), water (10 ml) and methanol (30 ml) at 15° C. was added dropwise 6N hydrochloric acid (7.6 ml) during 20 minutes. After 50 minutes, the reaction mixture was diluted with water and extracted three times with chloroform. The extracts combined were washed with brine, dried over anhydrous magnesium sulfate, and evaporated in vacuo. The residue was chromatographed on silica gel (3% methanol in chloroform). The first eluted compound was designated as isomer A and second eluted one was isomer B. Isomer A with high Rf value on thin layer chromatography (8% methanol in chloroform) and isomer B with low Rf value are configurational isomers at the hydroxyimino group of the desired N-(2-hydroxyimino-4-methyl-5-nitro-3-hepten-1-yl)- 3-pyridinecarboxamide. Crystallization of isomer A from toluene - ethyl acetate gave one isomer of N-(2-hydroxyimino-4-methyl-5-nitro-3-hepten-1-yl)-3-pyridinecarboxamide (267.5 mg).

mp: 136°–137° C.

IR (Nujol): 3300, 1635, 1545, 1460, 1370 cm$^{-1}$

NMR (DMSO-d$_6$, δ): 0.75 (3H, t, J=7.6 Hz), 1.83 (3H, s), 1.7–2.2 (2H, m), 4.1–4.4 (2H, m), 5.10 (1H, t, J=7.6 Hz), 6.08 (1H, s), 7.52 (1H, dd, J=4.8, 7.9 Hz), 8.17 (1H, d, J=7.9 Hz), 8.72 (1H, d, J=4.1 Hz), 8.9–9.1 (2H, m), 11.50 (1H, s)

Crystallization of isomer B from ethyl acetate - ethyl ether gave the other isomer of N-(2-hydroxyimino-4-methyl-5-nitro-3-hepten-1-yl)-3-pyridinecarboxamide (170 mg).

mp: 105°–108° C.

IR (Nujol): 3360, 1645, 1590, 1535, 1375 cm$^{-1}$

NMR (DMSO-d$_6$, δ): 0.79 (3H, t, J=8.8 Hz), 1.65 (3H, s), 1.7–2.2 (2H, m), 4.0–4.3 (2H, m), 5.17 (1H, t, J=7.5 Hz, 6.10 (1H, s), 7.50 (1H, dd, J=4.8, 7.9 Hz), 8.16 (1H, d, J=8.0 Hz), 8.70 (1H, d, J=3.9 Hz), 8.9–9.1 (2H, m), 11.04 (1H, s)

EXAMPLE 19

N-(2-Hydroxyimino-4-methyl-5-nitro-3-hexen-1-yl)-3-pyridinecarboxamide was prepared in a similar manner to that of Example 18.

Isomer A:

mp: 137°–139° C. (methanol - ethyl acetate)

IR (Nujol): 3300, 1635, 1540, 1350 cm$^{-1}$

NMR (DMSO-d$_6$, δ): 1.48 (3H, d, J=6.7 Hz), 1.84 (3H, s), 4.27 (2H, d, J=5.7 Hz), 5.33 (1H, q, J=6.7 Hz), 6.07 (1H, s), 7.52 (1H, dd, J=4.8, 7.6 Hz), 8.18 (1H, d, J=7.6 Hz), 8.72 (1H, d, J=4.9 Hz), 9.0–9.1 (2H, m), 11.44 (1H, s)

Isomer B:

mp: 108°–111° C. (ethyl acetate - diethyl ether)

IR (Nujol): 3270, 1635, 1545, 1350 cm$^{-1}$

NMR (DMSO-d$_6$, δ): 1.52 (3H, d, J=6.8 Hz), 1.65 (3H, d, J=0.9 Hz), 4.14 (2H, d, J=5.8 Hz), 5.37 (1H, q, J=6.8 Hz), 6.09 (1H, s), 7.50 (1H, dd, J=4.8, 7.9 Hz), 8.0–8.1 (1H, m), 8.70 (1H, dd, J=1.5, 4.8 Hz), 8.92 (1H, t, J=5.8 Hz), 8.97 (1H, d, J=1.5 Hz), 11.03 (1H, s)

EXAMPLE 20

N-(2-Hydroxyimino-4-isopropyl-5-nitro-3-hexen-1yl)-3-pyridinecarboxamide was prepared in a similar manner to that of Example 18.

mp: 132°–135° C. (ethyl acetate - diethyl ether)

IR (Neat): 3300, 1635, 1550, 1370 cm$^{-1}$

NMR (DMSO-d$_6$, δ): 0.92 (3H, d, J=6.9 Hz), 1.04 (3H, d, J=6.9 Hz), 1.39 (3H, d, J=6.7 Hz), 3.3–3.5 (1H, m), 4.0–4.4 (2H, m), 5.32 (1H, q, J=6.7 Hz), 5.98 (1H, s), 7.51 (1H, dd, J=4.8, 7.9 Hz), 8.1–8.2 (1H, m), 8.71 (1H, d, J=3.4 Hz), 8.9–9.0 (2H, m), 11.34 (1H, s)

EXAMPLE 21

N-[2-Hydroxyimino-3-(2-nitrocyclohexylidene)propyl]-3-pyridinecarboxamide was prepared in a similar manner to that of Example 18.

mp: 149°–151° C. (ethyl acetate - diethyl ether)

IR (Nujol): 3300, 1640, 1550, 1530, 1370 cm$^{-1}$

NMR (DMSO-d$_6$, δ): 1.2–2.4 (7H, m), 2.7–2.9 (1H, m), 4.24 (2H, d, J=6.0 Hz), 5.27 (1H, t, J=4.3 Hz), 5.84 (1H, s), 7.51 (1H, dd, J=4.8, 7.9 Hz), 8.1–8.2 (1H, m), 8.9–9.1 (2H, m), 11.36 (1H, s)

EXAMPLE 22

N-(2-Hydroxyimino-6-methoxy-4-methyl-5-nitro-3-hexen-1-yl)-4-pyridinecarboxamide was prepared in a similar manner to that of Example 18.

mp: 154°–156° C. (dec.) (ethyl acetate)

IR (Nujol): 3300, 1640, 1540, 1370 cm$^{-1}$

NMR (DMSO-d$_6$, δ): 1.88 (3H, d, J=1.2 Hz), 3.35 (3H, s), 3.5–4.0 (2H, m), 4.24 (2H, d, J=5.9 Hz), 5.3–5.5 (1H, m), 6.09 (1H, s), 7.7–7.8 (2H, m), 8.7–8.8 (2H, m), 9.06 (1H, t, J=5.9 Hz), 11.49 (1H, s)

EXAMPLE 23

1-Acetylamino-2-hydroxyimino-4-methyl-5-nitro-3-heptene was prepared in a similar manner to that of Example 18 as an oil.

Isomer A:

IR (Neat): 3200, 1650, 1560, 1360 cm$^{-1}$

NMR (DMSO-d$_6$, δ): 0.84 (3H, t, J=7.4 Hz), 1.81 (3H, s), 1.82 (3H, s), 1.8–2.2 (2H, m), 3.99 (2H, d, J=6.0 Hz), 5.12 (1H, t, J=7.5 Hz), 6.00 (1H, s), 8.11 (1H, t, J=6.0 Hz), 11.33 (1H, s)

Isomer B:

Oil

IR (Neat): 3200, 1640, 1540, 1365 cm$^{-1}$

NMR (DMSO-d$_6$, δ): 0.85 (3H, t, J=7.4Hz), 1.62 (3H, d, J=0.9 Hz), 1.78 (3H, s), 1.8–2.2 (2H, m), 3.8–4.0 (2H, m), 5.16 (1H, t, J=7.5 Hz), 6.04 (1H, s), 8.05 (1H, t, J=5.6 Hz), 10.98 (1H, s)

EXAMPLE 24

1-Acetylamino-4-ethyl-2-hydroxyimino-5-nitro-3-heptene was prepared in a similar manner to that of Example 18 as an oil.

NMR (DMSO-d$_6$, δ): 0.87 (3H, t, J=7.3 Hz), 0.97 (3H, t, J=7.4 Hz), 1.82 (3H, s), 1.8–2.4 (4H, m), 3.99 (2H, d, J=6.1 Hz), 5.11 (1H, t, J=6.8 Hz), 5.87 (1H, s), 8.11 (1H, t, J=6.1 Hz), 11.30 (1H, s)

EXAMPLE 25

N-(4-Ethyl-2-hydroxyimino-5-nitro-3-hepten-1-yl)-3-pyridinecarboxamide was prepared in a similar manner to that of Example 18.

Isomer A:

mp: 131°–133° C. (dec.) (methanol - water)

IR (Nujol): 3270, 1635, 1545, 1370 cm$^{-1}$

NMR (DMSO-d$_6$, δ): 0.73 (3H, t, J=7.3 Hz), 0.98 (3H, t, J=7.4 Hz), 1.6–2.1 (2H, m), 2.2–2.5 (2H, m), 4.27 (2H, d, J=6.0 Hz), 5.08 (1H, t, J=7.2 Hz), 6.07 (1H, s), 7.5–7.6 (1H, m), 8.1–8.3 (1H, m), 8.72 (1H, dd, J=1.6, 4.8 Hz), 8.9–9.1 (2H, m), 11.42 (1H, s)

Isomer B:

mp: 116°–118° C. (methanol - isopropyl ether)

IR (Nujol): 3260, 1645, 1550, 1375 cm$^{-1}$

NMR (DMSO-d$_6$, δ): 0.83 (3H, t, J=7.3 Hz), 0.94 (3H, t, J=7.6 Hz), 1.7–2.2 (4H, m), 4.14 (2H, d, J=5.8 Hz), 5.14 (1H, t, J=7.3 Hz), 6.05 (1H, s), 7.51 (1H, dd, J=4.8, 7.9 Hz), 8.1–8.3 (1H, m), 8.70 (1H, dd, J=1.6, 4.8 Hz), 8.9–9.1 (2H, m), 11.02 (1H, s)

EXAMPLE 26

A mixture of N-(4-ethyl-2-hydroxyimino-5-nitro-3-hexen-1-yl)-3-pyridinecarboxamide (306 mg), 3-chloroperbenzoic acid (323 mg), chloroform (15 ml) and acetone (40 ml) was stirred at room temperature for 10 hours. The resulting precipitates were collected and washed with acetone to give N-(4-ethyl-2-hydroxyimino-5-nitro-3-hexen-1-yl)-3-pyridinecarboxamide 1-oxide.

mp: 174° C. (dec.)

IR (Nujol): 1645, 1540, 1360 cm$^{-1}$

NMR (DMSO-d$_6$, δ): 0.94 (3H, t, J=7.4 Hz), 1.49 (3H, d, J=6.7 Hz), 2.1–2.5 (2H, m), 4.22 (2H, d, J=5.9 Hz), 5.32 (1H, q, J=6.7 Hz), 5.98 (1H, s), 7.4–7.8 (2H, m), 8.3–8.4 (1H, m), 8.54 (1H, s), 9.07 (1H, d, J=5.9 Hz), 11.43 (1H, s)

EXAMPLE 27

N-(4-Ethyl-2-hydroxyimino-5-nitro-3-hexen-1-yl)urea was prepared in a similar manner to that of Example 18 as an oil.

IR (Neat): 3250, 1645, 1540 cm$^{-1}$

NMR (DMSO-d$_6$, δ): 0.97 (3H, t, J=7 Hz), 1.58 (3H, d, J=7 Hz), 2.2–2.5 (2H, m), 3.91 (2H, d, J=6 Hz), 5.3–5.4 (1H, m), 5.60 (2H, br s), 6.03 (1H, s), 6.18 (1H, br t, J=6 Hz), 11.27 (1H, s)

EXAMPLE 28

3-[N-(4-Ethyl-2-hydroxyimino-5-nitro-3-hexen-1-yl)carbamoyl]-4-pyridinecarboxamide was prepared in a similar manner to that of Example 18.

mp: 122°–123° C. (chloroform)

IR (Nujol): 3400, 1670, 1640, 1530 cm$^{-1}$

NMR (DMSO-d$_6$, δ): 0.97 (3H, t, J=7 Hz), 1.59 (3H, d, J=7 Hz), 2.2–2.4 (2H, m), 4.18 (2H, d, J=6 Hz), 5.44 (1H, q, J=7 Hz), 6.21 (1H, s), 7.39 (1H, d, J=5 Hz), 7.57 (1H, s), 8.06 (1H, s), 8.7–8.8 (2H, m), 8.83 (1H, br t, J=6 Hz), 11.41 (1H, s)

EXAMPLE 29

N-(4-Ethyl-2-hydroxyimino-5-nitro-3-hexen-1-yl)-4-pyridinecarboxamide was prepared in a similar manner to that of Example 18.

mp: 145°–148° C. (methanol - chloroform)

IR (Nujol) : 3225, 1640, 1540 cm$^{-1}$

NMR (DMSO-d$_6$, δ): 0.94 (3H, t, J=7 Hz), 1.47 (3H, d, J=7 Hz), 2.2–2.4 (2H, m), 4.25 (2H, d, J=6 Hz), 5.30 (1H, q, J=7 Hz), 5.99 (1H, s), 7.73 (2H, dd, J=2, 5 Hz), 8.74 (2H, dd, J=2, 5 Hz), 9.07 (1H, br t, J=6 Hz), 11.43 (1H, s)

EXAMPLE 30

N-(4-Ethyl-2-hydroxyimino-5-nitro-3-hexen-1-yl)-2-methyl-3-pyridinecarboxamide was prepared in a similar manner to that of Example 18.

Isomer A:

mp: 128°–129° C. (ethyl acetate)

IR (Nujol): 3300, 1645, 1580, 1545 cm$^{-1}$

NMR (DMSO-d$_6$, δ): 1.00 (3H, t, J=7 Hz), 1.56 (3H, d, J=7 Hz), 2.3–2.5 (2H, m), 2.51 (3H, s), 4.22 (2H, d, J=6 Hz), 5.36 (1H, q, J=7 Hz), 6.04 (1H, s), 7.29 (1H, dd, J=5, 8 Hz), 7.70 (1H, dd, J=2, 8 Hz), 8.51 (1H, dd, J=2, 5 Hz), 8.73 (1H, br t, J=6 Hz), 11.41 (1H, s)

Isomer B:

mp: 128°–129° C. (ethyl acetate)

IR (Nujol): 3250, 1635, 1575, 1540 cm$^{-1}$

NMR (DMSO-d$_6$, δ): 0.98 (3H, t, J=7 Hz), 1.59 (3H, d, J=7 Hz), 2.0–2.2 (2H, m), 2.50 (3H, s), 4.06 (2H, d, J=6 Hz), 5.40 (1H, q, J=7 Hz), 6.03 (1H, s), 7.27 (1H, dd, J=5, 8 Hz), 7.66 (1H, dd, J=2, 8 Hz), 8.49 (1H, dd, J=2, 5 Hz), 8.66 (1H, br t, J=6 Hz), 11.03 (1H, s)

EXAMPLE 31

N-(4-Ethyl-2-hydroxyimino-5-nitro-3-hexen-1-yl)-2-methylthio-3-pyridinecarboxamide was prepared in a similar manner to that of Example 18.

Isomer A:

mp: 161°–163° C. (ethyl acetate)

IR (Nujol): 3250, 1710, 1640, 1540 cm$^{-1}$

NMR (DMSO-d$_6$, δ): 0.98 (3H, t, J=7 Hz), 1.55 (3H, d, J=7 Hz), 2.2–2.6 (2H, m), 2.43 (3H, s), 4.20 (2H, d, J=6 Hz), 5.33 (1H, q, J=7 Hz), 6.06 (1H, s), 7.20 (1H, dd, J=5, 8 Hz), 7.65 (1H, dd, J=2, 8 Hz), 8.55 (1H, dd, J=2, 5 Hz), 8.78 (1H, br t, J=6 Hz), 11.41 (1H, s)

Isomer B:

mp: 132°–133° C. (methanol)

IR (Nujol): 3250, 1640, 1540 cm$^{-1}$

NMR (DMSO-d$_6$, δ): 0.96 (3H, t, J=7 Hz), 1.58 (3H, d, J=7 Hz), 2.1–2.2 (2H, m), 2.41 (3H, s), 4.07 (2H, d, J=6 Hz), 5.38 (1H, q, J=7 Hz), 6.02 (1H, s), 7.18 (1H, dd, J=5, 8 Hz), 7.73 (1H, dd, J=2, 8 Hz), 8.53 (1H, dd, J=2, 5 Hz), 8.72 (1H, br t, J=6 Hz), 11.02 (1H, s)

EXAMPLE 32

N-(4-Ethyl-2-hydroxyimino-5-nitro-3-hexen-1-yl)-2-chloro-3-pyridinecarboxamide was prepared in a similar manner to that of Example 18.

mp: 131°–136° C. (methanol - diethyl ether)

IR (Nujol): 3300, 1655, 1580, 1540 cm$^{-1}$

NMR (DMSO-d$_6$, δ): 0.99 (3H, t, J=7 Hz), 1.59 (3H, d, J=7 Hz), 2.2–2.4 (2H, m), 2.43 (2H, d, J=6 Hz), 5.36 (1H, q, J=7 Hz), 6.08 (1H, s), 7.52 (1H, dd, J=5, 8 Hz), 7.86 (1H, dd, J=2, 8 Hz), 8.49 (1H, dd, J=2, 5 Hz), 8.91 (1H, br t, J=6 Hz), 11.45 (1H, s)

EXAMPLE 33

N-(4-Ethyl-2-hydroxyimino-5-nitro-3-hexen-1-yl)-2-hydroxy-3-pyridinecarboxamide was prepared in a similar manner to that of Example 18.

Isomer A:

mp: 92°–95° C. (ethyl acetate)

IR (Nujol): 1670, 1590, 1540 cm$^{-1}$

NMR (DMSO-d$_6$, δ): 0.96 (3H, t, J=7 Hz), 1.51 (3H, d, J=7 Hz), 2.2–2.4 (2H, m), 4.25 (2H, d, J=6 Hz), 5.30 (1H, q, J=7 Hz), 6.01 (1H, s), 6.47 (1H, t, J=6 Hz), 7.71 (1H, br s), 8.32 (1H, dd, J=2, 6 Hz), 9.99 (1H, t, J=6 Hz), 11.42 (1H, s), 12.51 (1H, br s)

Isomer B:

mp: 159°–160° C. (ethyl acetate)

IR (Nujol): 1670, 1590, 1540 cm$^{-1}$

NMR (DMSO-d$_6$, δ): 0.95 (3H, t, J=7 Hz), 1.58 (3H, d, J=7 Hz), 2.1–2.2 (2H, m), 4.16 (2H, d, J=6 Hz), 5.38 (1H, q, J=7 Hz), 6.06 (1H, s), 6.47 (1H, t, J=7 Hz), 7.71 (1H, s), 8.33 (1H, dd, J=2, 7 Hz), 10.02 (1H, br t, J=6 Hz), 11.08 (1H, s), 12.50 (1H, br s)

EXAMPLE 34

N-(4-Ethyl-2-hydroxyimino-5-nitro-3-hexen-1-yl)-3-quinolinecarboxamide was prepared in a similar manner to that of Example 18.

mp: 168°–170° C. (methanol - ethyl acetate)

IR (Nujol): 3250, 1630, 1550 cm$^{-1}$

NMR (DMSO-d$_6$, δ): 0.99 (3H, t, J=7 Hz), 1.47 (3H, d, J=7 Hz), 2.2–2.5 (2H, m), 4.32 (2H, d, J=6 Hz), 5.31 (1H, q, J=7 Hz), 6.07 (1H, s), 7.71 (1H, br t, J=8 Hz), 7.8–7.9 (1H, m), 8.10 (2H, d, J=8 Hz), 8.81 (1H, d, J=2 Hz), 9.15 (1H, br t, J=6 Hz), 9.27 (1H, d, J=2 Hz), 11.44 (1H, s)

EXAMPLE 35

N-(4-Ethyl-2-hydroxyimino-5-nitro-3-hexen-1-yl)-6-methyl-3-pyridinecarboxamide was prepared in a similar manner to that of Example 18.

mp: 150°–151° C. (chloroform)

IR (Nujol): 3250, 1630, 1545, 1490 cm$^{-1}$

NMR (DMSO-d$_6$, δ): 0.97 (3H, t, J=7 Hz), 1.46 (3H, d, J=7 Hz), 2.2–2.4 (2H, m), 2.52 (3H, s), 4.23 (2H, d, J=6 Hz), 5.29 (1H, q, J=7 Hz), 5.99 (1H, s), 7.36 (1H, d, J=8 Hz), 8.05 (1H, dd, J=2, 8 Hz), 8.8–8.9 (2H, m), 11.40 (1H, s)

EXAMPLE 36

N-(4-Ethyl-2-hydroxyimino-5-nitro-3-hexen-1-yl)-2-pyrazinecarboxamide was prepared in a similar manner to that of Example 18.

mp: 120°–121° C. (ethyl acetate)

IR (Nujol): 3250, 1665, 1550, 1530 cm$^{-1}$

NMR (DMSO-d$_6$, δ): 0.94 (3H, t, J=7 Hz), 1.55 (3H, d, J=7 Hz), 2.0–2.2 (2H, m), 4.15 (2H, d, J=6 Hz), 5.35 (1H, q, J=7 Hz), 6.02 (1H, s), 8.7–8.8 (1H, m), 8.88

(1H, d, J=2 Hz), 9.05 (1H, br t, J=6 Hz), 9.18 (1H, d, J=2 Hz), 11.04 (1H, s)

EXAMPLE 37

N-(4-Ethyl-2-hydroxyimino-5-nitro-3-hexen-1-yl)methanesulfonamide was prepared in a similar manner to that of Example 18 as an oil.

IR (Neat) : 3250, 1545, 1350, 1310 cm$^{-1}$

NMR (DMSO-d$_6$, δ): 1.01 (3H, t, J=7 Hz), 1.62 (3H, d, J=7 Hz), 2.2–2.5 (2H, m), 2.88 (3H, s), 3.95 (2H, d, J=6 Hz), 5.36 (1H, q, J=7 Hz), 6.17 (1H, s), 7.37 (1H, br t, J=6 Hz), 11.52 (1H, s)

EXAMPLE 38

N-(4-Ethyl-2-hydroxyimino-5-nitro-3-hexen-1-yl)propionamide was prepared in a similar manner to that of Example 18.

Isomer A:

Oil

IR (Neat) : 3225, 1635, 1530 cm$^{-1}$

NMR (DMSO-d$_6$, δ): 0.9–1.1 (6H, m), 1.56 (3H, d, J=7 Hz), 2.0–2.5 (4H, m), 4.01 (2H, d, J=6 Hz), 5.32 (1H, q, J=7 Hz), 5.92 (1H, s), 8.04 (1H, br t, J=6 Hz), 11.30 (1H, s)

Isomer B:

Oil

IR (Neat): 3250, 1640, 1540, 1350 cm$^{-1}$

NMR (DMSO-d$_6$, δ): 0.9–1.1 (6H, m), 1.58 (3H, d, J=7 Hz), 2.0–2.2 (4H, m), 3.88 (2H, d, J=6 Hz), 5.36 (1H, q, J=7 Hz), 5.94 (1H, s), 7.96 (1H, br t, J=6 Hz), 10.93 (1H, s)

EXAMPLE 39

N-(4-Ethyl-2-hydroxyimino-5-nitro-3-hexen-1-yl)-3-pyridinesulfonamide was prepared in a similar manner to that of Example 18 as an oil.

Isomer A:

IR (Neat): 3250, 1540, 1370, 1320 cm$^{-1}$

NMR (DMSO-d$_6$, δ): 0.90 (3H, t, J=7.5 Hz), 1.58 (3H, d, J=6.8 Hz), 2.0–2.3 (2H, m), 3.78 (2H, d, J=6.4 Hz), 5.30 (1H, q, J=6.8 Hz), 6.04 (1H, s), 7.62 (1H, dd, J=4.9, 8.1 Hz), 8.1–8.2 (1H, m), 8.3–8.4 (1H, m), 8.93 (1H, s), 11.53 (1H, s)

Isomer B:

IR (Neat): 3250, 1650, 1540, 1370 cm$^{-1}$

NMR (DMSO-d$_6$, δ): 0.93 (3H, t, J=7.6 Hz), 1.57 (3H, d, J=6.8 Hz), 2.04 (2H, q, J=7.6 Hz), 3.68 (2H, d, J=5.9 Hz), 5.35 (1H, q, J=6.8 Hz), 5.87 (1H, s), 7.64 (1H, dd, J=4.9, 5.3 Hz), 8.1–8.3 (2H, m), 8.95 (1H, s), 11.14 (1H, s)

EXAMPLE 40

N-(4-Ethyl-2-hydroxyimino-5-nitro-3-hexen-1-yl)oxmate was prepared in a similar manner to that of Example 18.

Isomer A:

mp: 114°–115° C. (ethyl acetate - diethyl ether)

IR (Nujol): 3300, 1660, 1540 cm$^{-1}$

NMR (DMSO-d$_6$, δ): 0.96 (3H, t, J=7 Hz), 1.53 (3H, d, J=7 Hz), 2.2–2.4 (2H, m), 4.03 (2H, d, J=6 Hz), 5.31 (1H, q, J=7 Hz), 5.92 (1H, s), 7.79 (1H, s), 8.06 (1H, br t, J=6 Hz), 11.39 (1H, s)

Isomer B:

mp: 95°–97° C. (ethyl acetate - diethyl ether)

IR (Nujol): 3325, 1665, 1550 cm$^{-1}$

NMR (DMSO-d$_6$, δ): 0.94 (3H, t, J=7 Hz), 1.57 (3H, d, J=7 Hz), 2.0–2.1 (2H, m), 3.94 (2H, d, J=6 Hz), 5.36 (1H, q, J=7 Hz), 5.95 (1H, s), 7.77 (1H, br s), 8.06 (1H, s), 8.78 (1H, br t, J=6 Hz), 11.01 (1H, s)

EXAMPLE 41

N-(4-Ethyl-2-hydroxyimino-5-nitro-3-hexen-1-yl)-4-pyrimidinecarboxamide was prepared in a similar manner to that of Example 18.

Isomer A:

mp: 150°–152° C. (ethyl acetate - diethyl ether)

IR (Nujol): 3625, 1670, 1580, 1540, 1520 cm$^{-1}$

NMR (DMSO-d$_6$, δ): 0.96 (3H, t, J=7 Hz), 1.42 (3H, d, J=7 Hz), 2.2–2.4 (2H, m), 4.26 (2H, d, J=6 Hz), 5.25 (1H, q, J=7 Hz), 5.97 (1H, s), 8.01 (1H, dd, J=1, 5 Hz), 9.08 (1H, d, J=5 Hz), 9.3–9.4 (2H, m), 11.42 (1H, s)

Isomer B:

mp: 118°–120° C. (ethyl acetate - diethyl ether)

IR (Nujol): 1675, 1550, 1510 cm$^{-1}$

NMR (DMSO-d$_6$, δ): 0.94 (3H, t, J=7 Hz), 1.55 (3H, d, J=7 Hz), 2.0–2.1 (2H, m), 4.15 (2H, d, J=6 Hz), 5.36 (1H, q, J=7 Hz), 6.01 (1H, s), 8.02 (1H, dd, J=1, 5 Hz), 9.08 (1H, d, J=5 Hz), 9.16 (1H, br t, J=6 Hz), 9.33 (1H, d, J=1 Hz), 11.05 (1H, s)

EXAMPLE 42

N-(4-Ethyl-2-hydroxyimino-5-nitro-3-hexen-1-yl)-3-pyridylacetamide was prepared in a similar manner to that of Example 18.

mp: 123°–125° C. (ethyl acetate)

IR (Nujol): 3250, 1640, 1540 cm$^{-1}$

NMR (DMSO-d$_6$, δ): 0.93 (3H, t, J=7 Hz), 1.47 (3H, d, J=7 Hz), 2.1–2.4 (2H, m), 3.48 (2H, s), 4.03 (2H, d, J=6 Hz), 5.23 (1H, q, J=7 Hz), 5.88 (1H, s), 7.33 (1H, dd, J=5, 8 Hz), 7.6–7.7 (1H, m), 8.4–8.5 (3H, m), 11.37 (1H, s)

EXAMPLE 43

N-(4-Ethyl-2-hydroxyimino-5-nitro-3-hexen-1-yl)-2,4-dimethylthiazole-5-carboxamide was prepared in a similar manner to that of Example 18.

mp: 158°–159° C. (ethyl acetate)

IR (Nujol) : 1635, 1545 cm$^{-1}$

NMR (DMSO-d$_6$, δ): 0.98 (3H, t, J=7 Hz), 1.50 (3H, d, J=7 Hz), 2.2–2.4 (2H, m), 2.49 (3H, s), 2.62 (3H, s), 4.16 (2H, d, J=6 Hz), 5.30 (1H, q, J=7 Hz), 5.97 (1H, s), 8.34 (1H, br t, J=6 Hz), 11.37 (1H, s)

EXAMPLE 44

To a mixture of N-[(2E,4E)- and (2Z,4E)-4-ethyl-2,4-hexadien-1-yl]-3,5-dimethylisoxazole-4-carboxamide (3.3 g), sodium nitrite (5.5 g), water (44 ml), and dioxane (88 ml) at 15°–20° C. was added dropwise 6N hydrochloric acid (13.3 ml) during 15 minutes. After being stirred for 20 minutes, the reaction mixture was neutralized with aqueous sodium hydrogen carbonate solution. Dichloromethane and sodium chloride were added to the reaction mixture. The separated organic phase was washed with brine, dried over anhydrous magnesium sulfate, and evaporated in vacuo. The residue was chromatographed on silica gel (4% methanol-chloroform) to give N-(4-ethyl-2-hydroxyimino-5-nitro-3-hexen-1-yl)-3,5-dimethylisoxazole-4-carboxamide.

mp: 100°–103° C. (isopropyl ether)

IR (Nujol): 3250, 1645, 1600, 1540 cm$^{-1}$

NMR (DMSO-d$_6$, δ): 0.99 (3H, t, J=7 Hz), 1.53 (3H, d, J=7 Hz), 2.3–2.5 (2H, m), 2.31 (1H, s), 2.41 (1H, s), 4.18 (2H, d, J=6 Hz), 5.34 (1H, q, J=7 Hz), 5.99 (1H, s), 8.21 (1H, br t, J=6 Hz), 11.40 (1H, s)

EXAMPLE 45

N-(4-Ethyl-2-hydroxyimino-5-nitro-3-hexen-1-yl)-5-methy-4-imidazolecarboxamide was prepared in a similar manner to that of Example 18.

Isomer A:

mp: 125°–127° C. (ethyl acetate - diethyl ether)

IR (Nujol): 3400, 3100, 1630, 1600, 1535 cm$^{-1}$

NMR (DMSO-d$_6$, δ): 0.96 (3H, t, J=7 Hz), 1.45 (3H, d, J=7 Hz), 2.2–2.4 (2H, m), 2.42 (3H, s), 4.15 (2H, dd, J=2, 6 Hz), 5.26 (1H, q, J=7 Hz), 6.02 (1H, s), 7.54 (1H, s), 8.03 (1H, br t, J=6 Hz), 11.33 (1H, s), 12.25 (1H, s)

Isomer B:

mp: 140°–141° C. (ethyl acetate)

IR (Nujol) : 3300, 1640, 1595, 1540 cm$^{-1}$

NMR (DMSO-d$_6$, δ): 0.95 (3H, t, J=7 Hz), 1.56 (3H, d, J=7 Hz), 2.0–2.1 (2H, m), 4.04 (2H, d, J=6 Hz), 5.36 (2H, q, J=7 Hz), 6.04 (1H, s), 7.52 (1H, s), 7.83 (1H, br t, J=6 Hz), 10.99 (1H, s), 12.24 (1H, br s)

EXAMPLE 46

5-(4-Ethyl-2-hydroxyimino-5-nitro-3-hexen-1-yl)-thiotetrazole- 1-acetamide was prepared in a similar manner to that of Example 18 as an oil.

Isomer A:

IR (Neat): 3300, 1700, 1610, 1550 cm$^{-1}$

NMR (DMSO-d$_6$, δ): 0.94 (3H, t, J=7 Hz), 1.56 (3H, d, J=7 Hz), 2.2–2.4 (2H, m), 4.14 (2H, s), 5.05 (2H, s), 5.33 (1H, q, J=7 Hz), 6.10 (1H, s), 7.55 (1H, br s), 7.88 (1H, br s), 11.82 (1H, s)

EXAMPLE 47

To a mixture of N-(4-methyl-2,4-heptadien-1-yl)-5-methylimidazole-4-carboxamide (19.1 g), sodium nitrite (33.9 g), water (130 ml) and methanol (400 ml) at 15° C. was added dropwise 6N hydrochloric acid (82 ml) during 20 minutes. After 30 minutes, the solution was concentrated in vacuo to remove the methanol and diluted with chloroform. The precipitate formed was filtered and washed with water. Recrystallization from methanol-water gave N-(2-hydroxyimino-4-methyl-5-nitro-3-hepten-1-yl)-5 -methylimidazole-4-carboxamide.

mp: 133°–136° C.

IR (Nujol): 3200, 1640, 1590, 1540, 1520, 1360 cm$^{-1}$

NMR (DMSO-d$_6$, δ): 0.72 (3H, t, J=7.4 Hz), 1.7–2.0 (2H, m), 1.82 (3H, s), 2.41 (3H, s), 4.0–4.3 (2H, m), 5.02 (1H, t, J=7.5 Hz), 6.06 (1H, s), 7.53 (1H, s), 8.00 (1H, t, J=6.3 Hz), 11.34 (1H, s), 12.2 (1H, br s)

EXAMPLE 48

N-(2-Hydroxyimino-4-methyl-5-nitro-3-hepten-1-yl)-3-methylpyrazole-5-carboxamide was prepared in a similar manner to that of Example 47.

mp: 188°–189° C. (methanol-water)

IR (Nujol): 3190, 3100, 1640, 1550, 1360 cm$^{-1}$

NMR (DMSO-d$_6$, δ): 0.80 (3H, t, J=7.4 Hz), 1.6–2.3 (2H, m), 1.63 (3H, s), 2.24 (3H, s), 4.06 (2H, d, J=5.8 Hz), 5.15 (1H, t, J=7.5 Hz), 6.09 (1H, s), 8.07 (1H, br s), 11.00 (1H, s), 12.94 (1H, s)

EXAMPLE 49

To a mixture of N-(4-methyl-2-4-heptadien-1-yl)-8 -oxo-7H-pyrido[2,3-d]pyridazin-5-acetamide (1.56 g), sodium nitrite (2.07 g), water (50 ml), methanol (45 ml), dioxane (50 ml) and tetrahydrofuran (50 ml) at 15° C. was added dropwise 6N hydrochloric acid (5 ml) during 20 minutes. After one hour, the solution was concentrated in vacuo to remove the organic solvents and extracted three times with ethyl acetate. The extracts combined were washed with brine, dried over anhydrous magnesium sulfate, and evaporated in vacuo. The residue was chromatographed on silica gel (5% methanol in ethyl acetate). The first eluted compound was designated as isomer A and second eluted one was isomer B. Isomer A with high Rf value on thin layer chromatography (5% methanol in ethyl acetate) and isomer B with lower Rf value are configurational isomers at the hydroxyimino group of the desired N-(2-hydroxyimino-4-methyl-5-nitro-3-hepten-1-yl)-8-oxo- 7H-pyrido[2,3-d]pyridazin-5-acetamide. Crystallization of isomer A from methanol-ethyl acetate gave one isomer of N-(2-hydroxyimino-4-methyl-5-nitro-3-hepten-1-yl)-8-oxo- 7H-pyrido[2,3-d]pyridazin-5-acetamide (125 mg).

mp: 143°–145° C.

IR (Nujol): 3300, 3170, 1660, 1540, 1340 cm$^{-1}$

NMR (DMSO-d$_6$, δ): 0.83 (3H, t, J=7.4 Hz), 1.6–2.3 (2H, m), 1.81 (3H, s), 3.90 (2H, s), 4.03 (2H, d, J=6.9 Hz), 5.04 (1H, t, J=7.5 Hz), 6.02 (1H, s), 7.85 (1H, dd, J=4.6 Hz, 8.1 Hz), 8.31 (1H, t, J=6.9 Hz), 8.60 (1H, dd, J=1.8 Hz, 8.1 Hz), 9.12 (1H, dd, J=1.8 Hz, 4.6 Hz), 11.37 (1H, s), 12.85 (1H, s)

Crystallization of isomer B from methanol-ethyl acetate gave the other isomer of N-(2-hydroxyimino-4 -methyl-5-nitro-3-hepten-1-yl)-8-oxo-7H-pyrido[2,3-d] -pyridazin-5-acetamide (150 mg).

mp: 169°–170° C.

IR (Nujol): 3300, 1685, 1630, 1540, 1360 cm$^{-1}$

NMR (DMSO-d$_6$, δ): 0.83 (3H, t, J=7.4 Hz), 1.61 (3H, s), 1.7–2.2 (2H, m), 3.85 (2H, s), 3.8–4.1 (2H, m), 5.14 (1H, t, J=7.4 Hz), 6.06 (1H, s), 7.84 (1H, dd, J=4.0 Hz, 8.0 Hz), 8.28 (1H, t, J=5.7 Hz), 8.59 (1H, dd, J=1.7 Hz, 8.0 Hz), 9.11 (1H, dd, J=1.7 Hz, 4.0 Hz), 11.00 (1H, s), 12.83 (1H, s)

EXAMPLE 50

To a mixture of N-(4-methyl-2,4-heptadien-1-yl)-6-amino-3-pyridinecarboxamide (13.3 g), sodium nitrite (21.2 g), water (51 ml), and methanol (160 ml) at 15° C. was added dropwise 6N hydrochloric acid (51.3 ml) during 30 minutes. After one hour, the methanol was removed under reduced pressure and the resulting precipitate was collected and washed with water. The precipitate was designated as isomer A. Recrystallization of isomer A from acetone-methanol gave N-(2-hydroxyimino-4-methyl-5 -nitro-3-hepten-1-yl)-6-amino-3-pyridinecarboxamide (2.68 g).

Isomer A:

mp: 190°–191° C. (acetone-methanol)

IR (Nujol): 3480, 3300, 1620, 1550, 1530, 1510, 1355 cm$^{-1}$

NMR (DMSO-d$_6$, δ): 0.72 (3H, t, J=7.4 Hz), 1.6–2.2 (2H, m), 1.86 (3H, s), 4.0–4.3 (2H, m), 5.05 (1H, t, J=7.4 Hz), 6.03 (1H, s), 6.42 (1H, d, J=8.7 Hz), 6.48 (2H, s), 7.78 (1H, dd, J=2.4 Hz, 8.7 Hz), 8.3–8.5 (2H, m), 11.36 (1H, s)

The filtrate was extracted three times with chloroform. The extracts combined were washed with brine, dried over magnesium sulfate, and evaporated in vacuo. The residue was chromatographed on silica gel (5% methanol in ethyl acetate). The second eluted fraction was evaporated in vacuo. The residue was designated as isomer B. The residue (2.4 g) and p-toluenesulfonic acid monohydrate (1.43 g) were dissolved in methanol (25 ml) and evaporated in vacuo. The residue was allowed to stand at 5° C. overnight. The solid formed was washed with 2-propanol and filtered to give the p-toluenesulfonic acid salt of isomer B [N-(2-hydroxyimino-4-methyl-5-nitro-3 -hepten-1-yl)-6-amino-3-pyridinecarboxamide].

mp: 169°–172° C.

IR (Nujol): 3280, 3140, 1670, 1665, 1655, 1620, 1545, 1370, 1120 cm$^{-1}$

NMR (DMSO-d$_6$, δ): 0.74 (3H, t, J=7.4 Hz), 1.7–2.2 (2H, m), 1.81 (3H, s), 2.30 (3H, s), 4.22 (1H, d, J=5.3 Hz), 5.07 (1H, t, J=7.5 Hz), 6.05 (1H, s), 7.03 (1H, d, J=9.3 Hz), 7.14 (2H, d, J=7.9 Hz), 7.52 (2H, d, J=7.9 Hz), 8.25 (1H, dd, J=2.0 Hz, 9.3 Hz), 8.41 (1H, d, J=2.0 Hz), 8.5 (2H, br s), 8.92 (1H, t, J=5.3 Hz), 11.44 (1H, s)

EXAMPLE 51

To a mixture of N-(4-ethyl-2,4-hexadien-1-yl)-6 -amino-3-pyridinecarboxamide (1.47 g), sodium nitrite (2.48 g), water (6 ml) and methanol (18 ml) at 15° C. was added dropwise 6N hydrochloric acid (4.8 ml) during 20 minutes. After 30 minutes the reaction mixture was diluted with chloroform (30 ml) and stirred for 10 minutes. The precipitate was filtered and washed with water. Recrystallization from methanol-water gave N-(4-ethyl-2-hydroxyimino-5-nitro-3-hexen-1-yl)-6 -amino-3-pyridinecarboxamide.

mp: 157°–161° C.

IR (Nujol): 3260, 1620, 1540, 1355 cm$^{-1}$

NMR (DMSO-d$_6$, δ): 0.97 (3H, t, J=7.4 Hz), 1.45 (3H, d, J=6.7 Hz), 2.2–2.5 (2H, m), 4.1–4.3 (2H, m), 5.28 (1H, q, J=6.7 Hz), 5.98 (1H, s), 6.43 (1H, d, J=8.7 Hz), 6.51 (2H, s), 7.78 (1H, dd, J=2.3 Hz, 8.7 Hz), 8.4–8.6 (2H, m), 11.33 (1H, m)

EXAMPLE 52

N-(2-Hydroxyimino-4-methyl-5-nitro-3-hepten-1-yl)-6 -oxo-1,4,5,6-tetrahydropyridazine-3-carboxamide was prepared in a similar manner to that of Example 18.

mp: 129°–130° C. (ethyl acetate)

IR (Nujol): 3380, 3250, 1690, 1670, 1650, 1630, 1550, 1380 cm$^{-1}$

NMR (DMSO-d$_6$, δ): 0.83 (3H, t, J=7.4 Hz), 1.61 (3H, s), 1.7–2.3 (2H, m), 2.37 (2H, t, J=8.2 Hz), 2.71 (2H, t, J=8.2 Hz), 4.00 (2H, d, J=5.9 Hz), 5.16 (1H, t, J=7.5 Hz), 6.05 (1H, s), 8.19 (1H, t, J=5.9 Hz), 11.00 (1H, s), 11.11 (1H, s)

EXAMPLE 53

N-(4-Ethyl-2-hydroxyimino-5-nitro-3-hexen-1-yl) -6 -methansulfonamido-3-pyridinecarboxamide was prepared in a similar manner to that of Example 18.

Isomer A:

mp: 131°–136° C. (ethyl acetate - methanol)

IR (Nujol): 3450, 1635, 1550, 1390, 1110 cm$^{-1}$

NMR (DMSO-d$_6$, δ): 0.97 (3H, t, J=7.5 Hz), 1.46 (3H, d, J=6.7 Hz), 2.2–2.5 (2H, m), 3.34 (3H, s), 4.22 (2H, d, J=5.9 Hz), 5.29 (1H, q, J=7.5 Hz), 5.99 (1H, s), 7.03 (1H, d, J=8.7 Hz), 8.11 (1H, dd, J=2.3 Hz, 8.7 Hz), 8.66 (1H, d, J=2.3 Hz), 8.80 (1H, t, J=5.9 Hz), 11.2 (1H, br s), 11.39 (1H, s)

Isomer B:

mp: 165°–167° C. (ethyl acetate)

IR (Nujol): 3450, 1650, 1540, 1370 cm$^{-1}$

NMR (DMSO-d$_6$, δ): 0.97 (3H, t, J=7.5 Hz), 1.46 (3H, d, J=6.7 Hz), 2.1–2.5 (2H, m), 3.33 (3H, s), 4.22 (2H, d, J=5.9 Hz), 5.29 (1H, q, J=7.5 Hz), 5.99 (1H, s), 7.03 (1H, d, J=8.7 Hz), 8.11 (1H, dd, J=1.9 Hz, 8.7 Hz), 8.66 (1H, d, J=1.9 Hz), 8.80 (1H, t, J=5.9 Hz), 11.17 (1H, br s), 11.38 (1H, s)

EXAMPLE 54

N-(2-Hydroxyimino-4-methyl-5-nitro-3-hepten-1-yl)-1H- 1,2,4-triazole-3-carboxamide was prepared in a similar manner to that of Example 18.

Isomer A:

mp: 131°–136° C. (ethyl acetate - diethyl ether)

IR (Nujol): 3350, 3100, 1650, 1540, 1360 cm$^{-1}$

NMR (DMSO-d$_6$, δ): 0.69 (3H, t, J=7.3 Hz), 1.81 (3H, s), 1.9–2.2 (2H, m), 4.1–4.3 (2H, m), 5.04 (1H, t, J=7.5 Hz), 6.05 (1H, s), 8.50 (1H, br s), 8.80 (1H, br s), 11.41 (1H, s)

Isomer B:

mp: 181°–182° C. (methanol - ethyl acetate)

IR (Nujol): 3200, 3150, 1650, 1565, 1550, 1370 cm$^{-1}$

NMR (DMSO-d$_6$, δ): 0.79 (3H, t, J=7.4 Hz), 1.64 (3H, s), 1.7–2.2 (2H, m), 4.10 (2H, d, J=6.0 Hz), 5.15 (1H, t, J=7.5 Hz), 6.09 (1H, s), 8.50 (1H, br s), 8.70 (1H, br s), 11.02 (1H, s), 14.6 (1H, br s)

EXAMPLE 55

N-(2-Hydroxyimino-4-methyl-5-nitro-3-hepten-1-yl)-4-imidazolecarboxamide was prepared in a similar manner to that of Example 18.

Isomer A:

mp: 157°–158° C. (ethyl acetate - diethyl ether)

IR (Nujol): 3250, 3070, 1630, 1580, 1550, 1505, 1370 cm$^{-1}$

NMR (DMSO-d$_6$, δ): 0.72 (3H, t, J=7.4 Hz), 1.7–2.2 (2H, m), 1.82 (3H, s), 4.1–4.3 (2H, m), 5.02 (1H, t, J=7.4 Hz), 6.06 (1H, s), 7.61 (1H, s), 7.72 (1H, s), 8.20 (1H, br s), 11.37 (1H, s), 12.52 (1H, br s)

Isomer B mp: 143°–144° C. (ethyl acetate - diethyl ether)

IR (Nujol): 3250, 3150, 1630, 1580, 1545, 1500, 1370 cm$^{-1}$

NMR (DMSO-d$_6$, δ): 0.80 (3H, t, J=7.4 Hz), 1.6–2.2 (2H, m), 1.64 (3H, s), 4.08 (2H, d, J=5.9 Hz), 5.16 (1H, t, J=7.5 Hz), 6.12 (1H, s), 7.16 (1H, s), 7.70 (1H, s), 7.95 (1H, t, J=5.9 Hz), 11.01 (1H, s), 12.5 (1H, br s)

EXAMPLE 56

N-(2-Hydroxyimino-4-methyl-5-nitro-3-hepten-1-yl)-3-pyridylacetamide was prepared in a similar manner to that of Example 18.
Isomer A
- mp: 140°–141° C. (ethyl acetate)
- IR (Nujol): 3250, 1640, 1540, 1365 cm$^{-1}$
- NMR (DMSO-d$_6$, δ): 0.80 (3H, t, J=7.4 Hz), 1.6–2.2 (2H, m), 1.82 (3H, s), 3.48 (2H, s), 4.03 (2H, d, J=6.1 Hz), 4.99 (1H, t, J=7.5 Hz), 5.93 (1H, s), 7.2–7.4 (1H, m), 7.6–7.7 (1H, m), 8.3–8.5 (3H, m), 11.39 (1H, s)

Isomer B
- mp: 138°–139° C. (ethyl acetate)
- IR (Nujol): 3280, 1650, 1540, 1360 cm$^{-1}$
- NMR (DMSO-d$_6$, δ): 0.81 (3H, t, J=7.4 Hz), 1.57 (3H, s), 1.6–2.2 (2H, m), 3.44 (2H, s), 3.9–4.0 (2H, m), 5.11 (1H, t, J=7.5 Hz), 6.02 (1H, s), 7.3–7.4 (1H, m), 7.6–7.7 (1H, m), 8.3–8.5 (3H, m), 11.01 (1H, s)

EXAMPLE 57

N-(2-Hydroxyimino-4-methyl-5-nitro-3-hepten-1-yl)-2-oxoindoline-5-carboxamide was prepared in a similar manner to that of Example 18.

Isomer A:
- mp: 111°–114° C. (ethyl acetate - diethyl ether)
- IR (Nujol): 3350, 3180, 1690, 1640, 1615, 1540, 1365 cm$^{-1}$
- NMR (DMSO-d$_6$, δ): 0.72 (3H, t, J=7.4 Hz), 1.6–2.2 (2H, m), 1.82 (3H, s), 3.53 (2H, m), 4.1–4.4 (2H, m), 5.04 (1H, t, J=7.5 Hz), 6.04 (1H, s), 6.85 (1H, d, J=8.7 Hz), 7.70 (1H, s), 7.72 (1H, d, J=8.7 Hz), 8.58 (1H, t, J=5.9 Hz), 10.63 (1H, s), 11.37 (1H, s)

Isomer B:
- mp: 111°–115° C. (ethyl acetate - diethyl ether)
- IR (Nujol): 3400, 3150, 1730, 1700, 1670, 1630, 1615, 1540, 1360 cm$^{-1}$
- NMR (DMSO-d$_6$, δ): 0.80 (3H, t, J=7.5 Hz), 1.63 (3H, s), 1.7–2.2 (2H, m), 3.52 (2H, s), 4.09 (2H, d, J=5.5 Hz), 5.15 (1H, t, J=7.5 Hz), 6.09 (1H, s), 6.83 (1H, d, J=8.6 Hz), 7.69 (1H, s), 7.70 (1H, d, J=8.6 Hz), 8.51 (1H, t, J=5.5 Hz), 10.61 (1H, s), 10.97 (1H, s)

EXAMPLE 58

N-(2-Hydroxyimino-4-methyl-5-nitro-3-hepten-1-yl)-2-fluoro-3-pyridinecarboxamide was prepared in a similar manner to that of Example 18.

Isomer A:
- mp: 91°–92° C. (diethyl ether - isopropyl ether)
- IR (Nujol): 3400, 3200, 1645, 1620, 1540, 1520, 1360 cm$^{-1}$
- NMR (DMSO-d$_6$, δ): 0.77 (3H, t, J=7.4 Hz), 1.7–2.2 (2H, m), 1.84 (3H, s), 4.23 (2H, d, J=6.0 Hz), 5.10 (1H, t, J=7.4 Hz), 6.09 (1H, s), 7.4–7.5 (1H, m), 8.1–8.3 (1H, m), 8.3–8.4 (1H, m), 8.77 (1H, t, J=6.0 Hz), 11.45 (1H, s)

Isomer B:
- mp: 112°–113° (ethyl acetate - diethyl ether)
- IR (Nujol): 3420, 1665, 1610, 1540, 1500, 1370 cm$^{-1}$
- NMR (DMSO-d$_6$, δ): 0.83 (3H, t, J=7.4 Hz), 1.65 (3H, s), 1.7–2.2 (2H, m), 4.0–4.2 (2H, m), 5.18 (1H, t, J=7.5 Hz), 6.09 (1H, s), 7.4–7.5 (1H, m), 8.0–8.2 (1H, m), 8.3–8.4 (1H, m), 8.72 (1H, br s), 11.06 (1H, s)

EXAMPLE 59

N-(4-Ethyl-2-hydroxyimino-5-nitro-3-hexen-1-yl)-2-methoxy-3-pyridinecarboxamide was prepared as an oil in a similar manner to that of Example 18.

Isomer A:
- IR (Neat): 3250, 1660, 1640, 1550, 1350 cm$^{-1}$
- NMR (CDCl$_3$, δ): 1.03 (3H, t, J=7.5 Hz), 1.67 (3H, d, J=7.7 Hz), 2.2–2.5 (2H, m), 4.14 (3H, s), 4.47 (2H, d, J=6.2 Hz), 5.09 (1H, s), 6.10 (1H, s), 7.06 (1H, dd, J=4.9 Hz, 7.6 Hz), 8.3–8.4 (1H, m), 8.43 (1H, t, J=6.2 Hz), 8.5–8.6 (1H, m), 8.9 (1H, br s)

Isomer B:
- IR (Neat): 3350, 1650, 1550, 1350 cm$^{-1}$
- NMR (CDCl$_3$, δ): 1.0–1.2 (3H, m), 1.6–1.8 (3H, m), 2.1–2.6 (2H, m), 4.11 (3H, s), 4.3–4.5 (2H, m), 5.0–5.3 (1H, m), 6.08 (1H, s), 7.0–7.1 (1H, m), 8.2–8.6 (3H, m)

EXAMPLE 60

N-(2-Hydroxyimino-4-methyl-5-nitro-3-hepten-1-yl)-4-hydroxy-7-methyl-1,8-naphthyridine-3-carboxamide was prepared in a similar manner to that of Example 18.

Isomer A:
- mp: 204°–205° C. (methanol - ethyl acetate)
- IR (Nujol): 3180, 1640, 1550, 1530, 1350 cm$^{-1}$
- NMR (DMSO-d$_6$, δ): 0.74 (3H, t, J=7.4 Hz), 1.7–2.2 (2H, m), 1.83 (3H, s), 2.63 (3H, s), 4.29 (2H, d, J=6.1 Hz), 5.09 (1H, t, J=7.4 Hz), 6.10 (1H, s), 7.43 (1H, d, J=8.2 Hz), 8.49 (1H, d, J=8.2 Hz), 8.61 (1H, s), 10.06 (1H, t, J=6.1 Hz), 11.46 (1H, s), 12.97 (1H, s)

Isomer B:
- mp: 196°–193° C. (methanol - ethyl acetate)
- IR (Nujol): 3230, 1640, 1550, 1520, 1355 cm$^{-1}$
- NMR (DMSO-d$_6$, δ): 0.81 (3H, t, J=7.4 Hz), 1.67 (3H, s), 1.7–2.2 (2H, m), 2.63 (3H, s), 4.21 (2H, d, J=5.5 Hz), 5.19 (1H, t, J=5.5 Hz), 6.18 (1H, s), 7.43 (1H, d, J=8.3 Hz), 8.48 (1H, d, J=8.3 Hz), 8.62 (1H, s), 10.09 (1H, t, J=5.5 Hz), 11.14 (1H, s), 12.98 (1H, br s)

EXAMPLE 61

N-(2-Hydroxyimino-4-methyl-5-nitro-3-hepten-1-yl)-2-ethyl-4-imidazolecarboxamide was prepared in a similar manner to that of Example 18.

Isomer A:
- mp: 75°–79° C. (ethyl acetate - diethyl ether)
- IR (Nujol): 3170, 1630, 1590, 1.540, 1360 cm$^{-1}$
- NMR (DMSO-d$_6$, δ): 0.73 (3H, t, J=7.4 Hz), 1.21 (3H, t, J=7.6 Hz), 1.7–2.2 (2H, m), 1.85 (3H, s), 2.64 (2H, q, J=7.4 Hz), 4.0–4.2 (2H, m), 5.03 (1H, t, J=7.4 Hz), 6.05 (1H, s), 7.48 (1H, s), 8.06 (1H, br s), 11.35 (1H, s), 12.2 (1H, br s)

Isomer B
- mp: 150°–152° C. (ethyl acetate - diethyl ether)
- IR (Nujol): 3150, 1630, 1580, 1545, 1370 cm$^{-1}$
- NMR (DMSO-d$_6$, δ): 0.81 (3H, t, J=7.3 Hz), 1.20 (3H, t, J=7.6 Hz), 1.64 (3H, s), 1.7–2.2 (2H, m), 2.62 (1H, q, J=7.6 Hz), 4.06 (2H, d, J=5.8 Hz), 5.17 (1H, t, J=7.5 Hz), 6.12 (1H, s), 7.47 (1H, s), 7.83 (1H, br s), 11.02 (1H, s), 12.14 (br s)

EXAMPLE 62

N-(2-Hydroxyimino-4-methyl-5-nitro-3-hepten-1-yl)-3-aminopyrazine-2-carboxamide was prepared as an oil in a similar manner to that of Example 18.

Isomer A: Oil
- IR (Neat): 3300, 1655, 1600, 1540, 1365 cm$^{-1}$

NMR (DMSO-d$_6$, δ): 0.68 (3H, t, J=7.3 Hz), 1.6–2.2 (2H, m), 1.80 (3H, s), 4.22 (2H, t, J=5.3 Hz), 5.04 (1H, t, J=7.4 Hz), 6.03 (1H, s), 7.5 (2H, br s), 7.83 (1H, s), 8.22 (1H, s), 8.98 (1H, t, J=5.3 Hz), 11.38 (1H, s)

Isomer B:

mp: 139°–1410° C. (ethyl acetate - chloroform)

IR (Nujol): 3380, 3320, 3220, 1645, 1590, 1550, 1530, 1370 cm$^{-1}$

NMR (DMSO-d$_6$, δ): 0.79 (3H, t, J=7.4 Hz), 1.64 (3H, s), 1.7–2.2 (2H, m), 4.11 (2H, d, J=5.9 Hz), 5.16 (1H, t, J=7.5 Hz), 6.10 (1H, s), 7.5 (2H, br s), 7.80 (1H, d, J=2.3 Hz), 8.21 (1H, d, J=2.3 Hz), 8.82 (1H, t, J=5.9 Hz), 11.03 (1H, s)

EXAMPLE 63

A solution of isomer A of N-(2-hydroxyimino-4-methyl-5-nitro-3-hepten-1-yl)-3-amino-2-pyrazinecarboxamide (475 mg) and p-toluenesulfonic acid monohydrate (280 mg) in methanol (20 ml) was evaporated in vacuo. The residue was allowed to stand at 5° C. overnight. The resulting solid was washed with 2-propanol and filtered to give the p-toluenesulfonic acid salt of isomer A {N-(2-hydroxyimino-4-methyl-5-nitro-3-hepten-1-yl)-3-amino-2-pyrazinecarboxamide}.

mp: 134°–135° C.

IR (Nujol): 3200, 1670, 1650, 1535, 1365, 1230, 1150 cm$^{-1}$

NMR (DMSO-d$_6$, δ): 0.68 (3H, t, J=7.4 Hz), 1.6–2.2 (2H, m), 1.80 (3H, s), 2.30 (3H, s), 4.1–4.3 (2H, m), 5.04 (1H, t, J=7.4 Hz), 6.03 (1H, s), 5.6–6.6 (4H, m), 7.13 (2H, d, J=7.9 Hz), 7.49 (2H, d, J=7.9 Hz), 7.84 (1H, d, J=2.4 Hz), 8.21 (1H, d, J=2.4 Hz), 9.00 (1H, t, J=6.2 Hz)

EXAMPLE 64

N-(2-Hydroxyimino-4-methyl-5-nitro-3-hepten-1-yl)-2,5-dimethylimidazole-4-carboxamide was prepared in a similar manner to that of Example 18.

Isomer A:

mp: 140°–141° C. (ethyl acetate - hexane)

IR (Nujol): 3150, 1630, 1545, 1310 cm$^{-1}$

NMR(DMSO-d$_6$, δ): 0.74 (3H, t, J=7 Hz), 1.81 (3H, s), 1.7–2.1 (2H, m), 2.22 (3H, s), 2.36 (3H, s), 4.0–4.1 (2H, m), 5.03 (1H, t, J=7 Hz), 6.05 (1H, s), 7.89 (1H, br t, J=6 Hz), 11.32 (1H, s), 11.91 (1H, br s)

Isomer B:

mp: 161°–162° C. (ethyl acetate - diethyl ether)

IR (Nujol): 3300, 1630, 1545, 1300 cm$^{-1}$

NMR (DMSO-d$_6$, δ): 0.82 (3H, t, J=7 Hz), 1.63 (3H, s), 1.7–2.2 (2H, m), 2.21 (3H, s), 2.36 (3H, s), 4.03 (2H, d, J=6 Hz), 5.17 (1H, t, J=7 Hz), 6.12 (1H, s), 7.71 (1H, br t, J=6 Hz), 11.01 (1H, s), 11.90 (1H, br s)

EXAMPLE 65

N-(2-Hydroxyimino-4-methyl-5-nitro-3-octen-1-yl)-3-pyridinecarboxamide was prepared in a similar manner to that of Example 18.

Isomer A:

mp: 128°–131° C. (ethyl acetate - diethyl ether)

IR (Nujol): 3250, 1635, 1540, 1310 cm$^{-1}$

NMR (DMSO-d$_6$, δ): 0.71 (3H, t, J=7 Hz), 1.0–1.2 (2H, m), 1.81 (3H, s), 1.7–2.0 (2H, m), 4.26 (2H, t, J=6 Hz), 5.15 (1H, t, J=7 Hz), 6.06 (1H, s), 7.5–7.6 (1H, m), 8.1–8.2 (1H, m), 8.72 (1H, dd, J=2 Hz, 5 Hz), 8.97 (1H, br t, J=6 Hz), 9.00 (1H, d, J=2 Hz), 11.42 (1H, s)

Isomer B:

mp: 114°–115° C. (ethyl acetate - diethyl ether)

IR (Nujol): 3250, 1640, 1545, 1300 cm$^{-1}$

NMR (DMSO-d$_6$, δ): 0.78 (3H, t, J=7 Hz), 1.1–1.2 (2H, m), 1.64 (3H, s), 1.7–1.8 (2H, m), 4.1–4.2 (2H, m), 5.22 (1H, t, J=7 Hz), 6.08 (1H, s), 7.50 (1H, dd, J=4 Hz, 8 Hz), 8.1–8.2 (1H, m), 8.70 (1H, dd, J=2 Hz, 5 Hz), 8.91 (1H, br t, J=6 Hz), 8.97 (1H, d, J=2 Hz), 11.01 (1H, s)

EXAMPLE 66

N-(2-Hydroxyimino-4-methyl-5-nitro-3-octen-1-yl)-3-pyridylacetamide was prepared in a similar manner to that of Example 18.

Isomer A:

mp 128°–129° C. (ethyl acetate - diethyl ether)

IR (Nujol): 3250, 1640, 1540 cm$^{-1}$

NMR (DMSO-d$_6$, δ): 0.89 (3H, t, J=7 Hz), 1.1–1.2 (2H, m), 1.7–1.8 (1H, m), 1.8 (3H, s), 1.9–2.1 (1H, m), 3.48 (2H, s), 4.02 (2H, d, J=6 Hz), 5.07 (1H, t, J=7 Hz), 5.95 (1H, s), 7.32 (1H, dd, J=5 Hz, 8 Hz), 7.6–7.7 (1H, m), 8.4–8.5 (3H, m), 11.39 (1H, s)

Isomer B:

mp 126°–127° C. (ethyl acetate -diethyl ether)

IR (Nujol): 3300, 1650, 1540, 1330 cm$^{-1}$

NMR (DMSO-d$_6$, δ): 0.89 (3H, t, J=7 Hz), 1.1–1.3 (2H, m), 1.58 (3H, s), 1.6–1.8 (1H, m), 1.9–2.1 (1H, m), 3.44 (2H, s), 3.92 (2H, t, J=6 Hz), 5.19 (1H, t, J=7 Hz), 6.04 (1H, s), 7.3–7.4 (1H, m), 7.6–7.7 (1H, m), 8.37 (1H, br t, J=6 Hz), 8.4–8.5 (2H, m), 11.01 (1H, s)

We claim:

1. A compound of the formula:

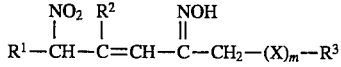

wherein R$^1$ and R$^2$ are each lower alkyl, X is —NH—, m is the integer 1 and R$^3$ is a group of the formula —(Y)$_n$—R$_4$, wherein Y is CO, n is the integer 1 and R$^4$ is pyridyl.

2. The compound of claim 1, wherein said compound is N-(4 -ethyl-2-hydroxyimino-6-methyl-5-nitro-3-hepten-1-Yl)-3-pyridine carboxamide.

* * * * *